(12) United States Patent
Han et al.

(10) Patent No.: US 11,906,491 B2
(45) Date of Patent: Feb. 20, 2024

(54) PEPTIDE MARKERS FOR AUTHENTICATING EJIAO AND RELATED GELATINS

(71) Applicant: Hong Kong Baptist University, Hong Kong (CN)

(72) Inventors: Quanbin Han, Hong Kong (CN); Wenjie Wu, Hong Kong (CN); Lifeng Li, Hong Kong (CN)

(73) Assignee: Hong Kong Baptist University, Hong Kong (CN)

( * ) Notice: Subject to any disclaimer, the term of this patent is extended or adjusted under 35 U.S.C. 154(b) by 103 days.

(21) Appl. No.: 17/443,963

(22) Filed: Jul. 29, 2021

(65) Prior Publication Data
US 2022/0042955 A1    Feb. 10, 2022

Related U.S. Application Data

(60) Provisional application No. 63/061,165, filed on Aug. 4, 2020.

(51) Int. Cl.
| | | |
|---|---|---|
| G01N 30/72 | (2006.01) | |
| G01N 30/88 | (2006.01) | |
| G01N 33/68 | (2006.01) | |
| G01N 30/02 | (2006.01) | |

(52) U.S. Cl.
CPC ............ *G01N 30/72* (2013.01); *G01N 30/88* (2013.01); *G01N 33/68* (2013.01); *G01N 2030/027* (2013.01); *G01N 2030/8831* (2013.01)

(58) Field of Classification Search
CPC ........ G01N 30/72; G01N 30/88; G01N 33/68; G01N 2030/027; G01N 2030/8831; G01N 33/6848
See application file for complete search history.

(56) References Cited

FOREIGN PATENT DOCUMENTS

| CN | 105837676 A | * | 8/2016 | ............. C07K 14/47 |
| CN | 105837676 A | | 8/2016 | |
| CN | 109280077 A | * | 1/2019 | ............. C07K 14/00 |
| CN | 109280077 A | | 1/2019 | |

OTHER PUBLICATIONS

Yang, H., et al., A novel strategy for the discrimination of gelatinous Chinese medicines based on enzymatic digestion followed by nano-flow liquid chromatography in tandem with orbitrap mass spectrum detection. Int J Nanomedicine, 2015. 10: p. 4947-55.
Committee., C.P., Chinese Pharmacopoeia. vol. 1. 2020, Beijing: Chinese Medical Science and Technology Press.
Li, Y., et al., Therapeutic effect of Colla corii asini on improving anemia and hemoglobin compositions in pregnant women with thalassemia. Int J Hematol, 2016. 104(5): p. 559-565.
(Continued)

*Primary Examiner* — Jill A Warden
*Assistant Examiner* — Michael Paul Shimek
(74) *Attorney, Agent, or Firm* — S&F/WEHRW

(57) ABSTRACT

Provided herein is a method for authenticating animal hide gelatins using peptide markers found animal hide gelatin hydrolysates. The method can be used to authenticate animal hide gelatins derived from donkey hide, horse hide, pig hide, and cattle hide.

13 Claims, 133 Drawing Sheets

Specification includes a Sequence Listing.

(56) References Cited

OTHER PUBLICATIONS

Li, X., et al., Species-specific identification of collagen components in Colla corii asini using a nano-liquid chromatography tandem mass spectrometry proteomics approach. Int J Nanomedicine, 2017. 12: p. 4443-4454.

Liu, R., et al., A strategy for identifying species-specific peptide biomarkers in deer-hide gelatin using untargeted and targeted mass spectrometry approaches. Anal Chim Acta, 2019. 1092: p. 32-41.

Stachniuk, A., et al., Liquid Chromatography-Mass Spectrometry Bottom-up Proteomic Methods in Animal Species Analysis of Processed Meat for Food Authentication and the Detection of Adulterations. Mass Spectrom Rev, 2021. 40 (1): p. 3-30.

Kumazawa, Y., et al., A novel LC-MS method using collagen marker peptides for species identification of glue applicable to samples with multiple animal origins. Heritage Science, 2018. 6(1).

Li, Y., et al., Simultaneous determination of heat stable peptides for eight animal and plant species in meat products using UPLC-MS/MS method. Food Chem, 2018. 245: p. 125-131.

Prandi, B., et al., Species specific marker peptides for meat authenticity assessment: A multispecies quantitative approach applied to Bolognese sauce. Food Control, 2019. 97: p. 15-24.

Van Vlierberghe, K., et al., Selection of universal peptide biomarkers for the detection of the allergen hazelnut in food trough a comprehensive, high resolution mass spectrometric (HRMS) based approach. Food Chem, 2020. 309: p. 125679.

Watson, A.D., et al., Meat Authentication via Multiple Reaction Monitoring Mass Spectrometry of Myoglobin Peptides. Anal Chem, 2015. 87(20): p. 10315-22.

Cheng, X.L., et al., Using the Doubly Charged Selected Ion Coupled with MS/MS Fragments Monitoring (DCSI-MS/MS) Mode for the Identification of Gelatin Species. J Anal Methods Chem, 2014. 2014: p. 764397.

Guo, S., et al., Marker peptide combination for source identification of gelatins obtained from Equidae hides by LC-MS/MS detection. Polymer Testing, 2020. 88.

Chen, X.L., Research on key Technologies for quality control of Colloids. 2014, Beijing University of Chinese Medicine.

Wang Fang, F.Y., Ye Mao, Cao Xiujun, Tong Xinzi, Peng Cheng, Guo Jinlin. , Screening and identification of E-jiao specific peptides based on bioinformatics and mass spectrometry. Chinese materia medica, 2019. 21(09): p. 1256-1261+1266.

Shi, F.H., B. J., Chi L. L., Li X., Xu L. H., Wei F., Cheng X. L., Gong L. P., Ma S. C . . . Discovery of donkey skin characteristic peptide and its application in the identification of donkey-hide gelatin. Chinese Journal of Pharmaceutical Analysis, 2017. 37(12): p. 2272-2278.

Sha, X.-M., et al., The identification of three mammalian gelatins by liquid chromatography-high resolution mass spectrometry. Lwt, 2018. 89: p. 74-86.

Cheng, X.L., et al., Identification of five gelatins by ultra performance liquid chromatography/time-of-flight mass spectrometry (UPLC/Q-TOF-MS) using principal component analysis. J Pharm Biomed Anal, 2012. 62: p. 191-5.

Committee., C.P., Chinese Pharmacopoeia. vol. 1. 2015, Beijing: Chinese Medical Science and Technology Press.

International Search Report and Written Opinion of PCT application No. PCT/CN2021/110107 issued from the International Search Authority dated Nov. 2, 2021.

Li et al.; Species-specific identification of collagen components in Colla corii asini using a nano-liquid chromatography tandem mass spectrometry proteomics approach; International Journal of Nanomedicine; Jun. 2017; vol. 12; pp. 4443-4454.

* cited by examiner

Table 1

| FIG. 1 No. | Donkey marker No. | m/z | RT (min) | Charge | Donkey | Horse | Cattle | Pig |
|---|---|---|---|---|---|---|---|---|
| 1 | / | 189.1288 | 5.31 | 1 | + | + | + | + |
| 2 | / | 228.6384 | 5.31 | 2 | + | + | + | + |
| 3 | / | 237.6447 | 5.31 | 2 | + | + | + | + |
| 4 | / | 233.1565 | 5.55 | 1 | + | + | + | + |
| 5 | / | 281.1566 | 5.59 | 1 | + | + | + | + |
| 6 | / | 260.2043 | 6.27 | 1 | + | + | + | + |
| 7 | / | 267.6266 | 6.27 | 2 | + | + | + | + |
| 8 | / | 288.2116 | 6.30 | | + | + | + | + |
| 9 | / | 290.1784 | 6.30 | | + | + | + | + |
| 10 | / | 276.1632 | 7.57 | 1 | + | + | + | + |
| 11 | / | 231.1771 | 7.77 | | + | + | + | + |
| 12 | / | 216.6198 | 8.26 | 2 | + | + | + | + |
| 13 | / | 223.1141 | 8.27 | 1 | + | + | + | + |
| 14 | / | 236.6544 | 9.34 | 2 | + | + | + | + |
| 15 | / | 272.1795 | 9.40 | 1 | + | + | + | + |
| 16 | / | 260.1678 | 9.58 | 1 | + | + | + | + |
| 17 | / | 277.1257 | 9.74 | 1 | + | + | + | + |
| 18 | / | 237.6260 | 10.08 | 2 | + | + | + | + |
| 19 | / | 242.1565 | 10.08 | 1 | + | + | + | + |

FIG. 10

| 20 | / | 249.6631 | 10.08 | 2 | + | + | + | + |
| 21 | / | 270.2001 | 10.08 | 1 | + | + | + | + |
| 22 | / | 274.1954 | 10.08 | 1 | + | + | + | + |
| 23 | / | 281.1213 | 10.08 | 1 | + | + | + | + |
| 24 | / | 295.1740 | 10.08 | 1 | + | + | + | + |
| 25 | / | 258.1766 | 10.10 | 2 | + | + | + | + |
| 26 | / | 231.1762 | 10.44 | 1 | + | + | + | + |
| 27 | / | 219.1404 | 10.98 | 1 | + | + | + | + |
| 28 | / | 295.1730 | 10.98 | 1 | + | + | + | + |
| 29 | / | 229.6280 | 12.09 | 2 | + | + | + | + |
| 30 | / | 272.6535 | 12.27 | 2 | + | + | + | + |
| 31 | / | 283.8095 | 12.27 | 2 | + | + | + | + |
| 32 | / | 292.6630 | 12.27 | 2 | + | + | + | + |
| 33 | / | 278.6662 | 12.50 | 2 | + | + | + | + |
| 34 | / | 297.6402 | 12.50 | 2 | + | + | + | + |
| 35 | / | 265.1621 | 13.32 | 1 | + | + | + | + |
| 36 | / | 245.1925 | 14.24 | 1 | + | + | + | + |
| 37 | / | 245.1925 | 15.38 | 1 | + | + | + | + |
| 38 | / | 243.1408 | 15.75 | 1 | + | + | + | + |
| 39 | / | 279.1418 | 17.53 | 1 | + | + | + | + |
| 40 | / | 279.1777 | 18.20 | 1 | + | + | + | + |

FIG. 10 (Continued)

| | | | | | | | | |
|---|---|---|---|---|---|---|---|---|
| 41 | / | 288.2009 | 20.49 | | + | + | + | + |
| 42 | / | 234.1024 | 22.27 | | + | + | + | + |
| | | | | | | | | |
| | | | | | | | | |
| 43 | / | 224.1352 | 31.00 | 1 | + | + | + | + |
| 44 | / | 250.1855 | 32.78 | 1 | + | + | + | + |
| 45 | / | 329.2007 | 5.31 | 1 | + | + | + | + |
| 46 | / | 345.2333 | 5.31 | 1 | + | + | + | + |
| 47 | / | 391.1910 | 5.31 | 1 | + | + | + | + |
| 48 | / | 321.1817 | 5.59 | 1 | + | + | + | + |
| 49 | / | 324.1811 | 5.59 | 2 | + | + | + | + |
| 50 | / | 372.6956 | 5.59 | 2 | + | + | + | + |
| 51 | / | 301.1832 | 6.30 | 2 | + | + | + | + |
| 52 | / | 303.6207 | 6.30 | 1 | + | + | + | + |
| 53 | / | 306.1739 | 6.30 | | + | + | + | + |
| 54 | / | 317.1910 | 6.30 | 3 | + | + | + | + |
| 55 | / | 323.1587 | 6.30 | | + | + | + | + |
| 56 | / | 323.4940 | 6.30 | | + | + | + | + |
| 57 | / | 329.1909 | 6.30 | 2 | + | + | + | + |
| 58 | / | 369.7033 | 6.30 | 2 | + | + | + | + |
| 59 | / | 373.2899 | 6.30 | 1 | + | + | + | + |

FIG. 10 (Continued)

| 60 | / | 388.2293 | 6.30 |   | + | + | + | + |
|---|---|---|---|---|---|---|---|---|
| 61 | / | 398.1658 | 6.30 |   | + | + | - | + |
| 62 | / | 347.2014 | 7.77 | 1 | + | + | + | + |
| 63 | / | 375.2342 | 7.77 | 1 | + | + | + | + |
| 64 | / | 325.6760 | 8.17 | 2 | + | + | - | - |
| 65 | / | 301.6758 | 8.27 | 2 | + | + | + | + |
| 66 | / | 320.1866 | 8.27 | 1 | + | + | + | - |
| 67 | / | 365.8721 | 8.27 |   | + | + | + | - |
| 68 | / | 385.2063 | 8.27 | 2 | + | + | + | + |
| 69 | / | 384.2149 | 8.64 | 2 | + | + | + | - |
| 70 | / | 395.6893 | 8.94 | 2 | + | + | + | + |
| 71 | / | 385.2661 | 9.40 | 1 | + | + | + | + |
| 72 | / | 393.2091 | 9.40 | 2 | + | + | + | + |
| 73 | / | 345.1529 | 9.63 | 1 | + | + | + | + |
| 74 | / | 350.1806 | 9.63 | 1 | + | + | + | + |
| 75 | / | 322.6805 | 10.06 | 2 | + | + | + | + |
| 76 | / | 302.1801 | 10.08 | 1 | + | + | + | + |
| 77 | / | 359.2392 | 10.08 | 1 | + | + | + | + |
| 78 | / | 385.2297 | 10.08 | 1 | + | + | + | + |
| 79 | / | 398.2194 | 10.08 |   | + | + | + | - |
| 80 | / | 372.2159 | 10.36 | 2 | + | + | + | + |

FIG. 10 (Continued)

| | | | | | | | | |
|---|---|---|---|---|---|---|---|---|
| 81 | / | 390.2222 | 10.60 | 2 | + | + | + | + |
| 82 | / | 339.1935 | 10.87 | 2 | + | + | + | + |
| 83 | / | 371.2385 | 10.98 | 1 | + | + | + | + |
| 84 | / | 379.7035 | 10.98 | 2 | + | + | + | + |
| 85 | / | 389.2488 | 11.01 | 1 | + | + | + | + |
| 86 | / | 393.2267 | 11.01 | 2 | + | + | + | - |
| 87 | / | 314.7013 | 11.46 | 2 | + | + | + | - |
| 88 | / | 347.7072 | 11.46 | 2 | + | + | + | + |
| 89 | / | 377.1953 | 11.46 | 1 | + | + | + | + |
| 90 | / | 305.6956 | 11.52 | 2 | + | + | + | + |
| 91 | / | 339.6729 | 11.52 | 2 | + | + | + | + |
| 92 | / | 314.6831 | 12.07 | 2 | + | + | + | + |
| 93 | / | 322.8205 | 12.27 | 3 | + | + | + | + |
| 94 | / | 327.8098 | 12.27 | 3 | + | + | + | + |
| 95 | / | 343.2051 | 12.27 | | + | + | + | + |
| 96 | / | 388.2296 | 12.27 | | + | + | + | + |
| 97 | / | 309.6738 | 12.35 | 2 | + | + | + | + |
| 98 | / | 374.7011 | 12.41 | 2 | + | + | + | + |
| 99 | / | 300.6175 | 12.78 | 2 | + | + | + | + |
| 100 | / | 320.2031 | 12.78 | 3 | + | + | + | + |
| 101 | / | 330.2011 | 12.78 | 2 | + | + | + | + |

FIG. 10 (Continued)

| | | | | | | | |
|---|---|---|---|---|---|---|---|
| 102 | / | 390.8836 | 12.91 | 3 | + | + | - | - |
| 103 | / | 392.2315 | 13.05 | 2 | + | + | + | + |
| 104 | / | 321.1797 | 13.31 | 2 | + | + | + | - |
| 105 | / | 369.2061 | 13.59 | 3 | + | + | + | + |
| 106 | / | 377.1926 | 13.59 | 1 | + | + | + | + |
| 107 | / | 381.8550 | 13.59 | 3 | + | + | + | + |
| 108 | / | 385.5505 | 13.59 | 3 | + | + | - | - |
| 109 | / | 386.8436 | 13.59 | 3 | + | + | + | + |
| 110 | / | 350.6348 | 14.08 | 2 | + | + | + | + |
| 111 | / | 359.6404 | 14.08 | 2 | + | + | + | + |
| 112 | / | 378.6137 | 14.08 | 2 | + | + | + | + |
| 113 | / | 398.2504 | 14.18 | 1 | + | + | + | + |
| 114 | / | 301.6768 | 14.24 | 2 | + | + | + | + |
| 115 | / | 332.2266 | 14.24 | 1 | + | + | + | + |
| 116 | / | 374.8536 | 14.46 | 3 | + | + | + | + |
| 117 | / | 379.8415 | 14.46 | 3 | + | + | + | + |
| 118 | / | 382.5030 | 14.46 | 3 | + | + | + | + |
| 119 | / | 396.2707 | 14.62 | 1 | + | + | + | + |
| 120 | / | 320.1733 | 14.88 | 1 | + | + | + | + |
| 121 | / | 353.4912 | 14.88 | 3 | + | + | + | + |
| 122 | / | 372.8516 | 14.88 | 3 | + | + | - | - |

FIG. 10 (Continued)

| | | | | | | | |
|---|---|---|---|---|---|---|---|
| 123 | / | 377.8407 | 14.88 | 3 | + | + | - | - |
| 124 | / | 329.2282 | 15.00 | 2 | + | + | + | + |
| 125 | / | 383.7419 | 15.00 | 2 | + | + | + | - |
| 126 | / | 398.2272 | 15.00 | 3 | + | + | + | + |
| 127 | / | 371.7236 | 16.41 | 2 | + | + | + | + |
| 128 | / | 312.8329 | 16.42 | 3 | + | + | + | + |
| 129 | / | 399.2711 | 17.34 | 1 | + | + | + | + |
| 130 | / | 366.2176 | 17.35 | 2 | + | + | + | + |
| 131 | / | 302.2166 | 18.21 | 1 | + | + | + | + |
| 132 | / | 391.2092 | 18.32 | 1 | + | + | + | + |
| 133 | / | 332.2273 | 18.89 | 1 | + | + | + | + |
| 134 | / | 374.2389 | 18.89 | 1 | + | + | + | + |
| 135 | / | 302.2159 | 19.22 | 1 | + | + | + | + |
| 136 | / | 316.2312 | 19.63 | 1 | + | + | + | + |
| 137 | / | 387.8462 | 19.63 | 3 | + | + | + | + |
| 138 | / | 330.1635 | 19.95 | 1 | + | + | + | + |
| 139 | / | 337.1392 | 20.13 | 2 | + | + | - | - |
| 140 | / | 392.9530 | 20.13 | 4 | + | + | - | - |
| 141 | / | 396.6962 | 20.13 | 4 | + | + | + | - |
| 142 | / | 344.2632 | 20.16 | 1 | + | + | + | + |
| 143 | / | 338.8360 | 21.02 | | + | + | - | - |

FIG. 10 (Continued)

| | | | | | | | |
|---|---|---|---|---|---|---|---|
| 144 | / | 335.1611 | 21.76 | 3 | + | + | + | + |
| 145 | / | 306.1484 | 23.08 | 2 | + | + | + | + |
| 146 | / | 393.7321 | 23.66 | 2 | + | + | - | - |
| 147 | / | 379.2181 | 24.94 | 2 | + | + | + | + |
| 148 | / | 422.2127 | 5.31 | 1 | + | + | + | + |
| 149 | / | 474.2799 | 5.31 | 1 | + | + | + | + |
| 150 | / | 459.2685 | 5.59 | 1 | + | + | + | + |
| 151 | / | 473.2346 | 5.59 | | + | + | + | - |
| 152 | / | 490.2600 | 5.59 | | + | + | + | + |
| 153 | / | 431.2478 | 6.30 | 1 | + | + | + | + |
| 154 | / | 443.2353 | 6.30 | 1 | + | + | + | + |
| 155 | / | 447.2105 | 6.30 | 1 | + | + | + | + |
| 156 | / | 462.2302 | 6.30 | 1 | + | + | + | + |
| 157 | / | 484.2314 | 6.30 | 2 | + | + | + | + |
| 158 | / | 445.2527 | 7.80 | 1 | + | + | + | + |
| 159 | / | 499.2625 | 7.80 | 1 | + | + | + | + |
| 160 | / | 432.2315 | 8.27 | 1 | + | + | + | + |
| 161 | / | 446.2717 | 8.27 | 1 | + | + | + | + |
| 162 | / | 426.7299 | 8.94 | 2 | + | + | + | + |
| 163 | / | 456.2434 | 8.94 | 2 | + | + | + | + |
| 164 | / | 400.2297 | 9.40 | 1 | + | + | + | + |

FIG. 10 (Continued)

| 165 | / | 404.2236 | 9.40 | 1 | + | + | + | + |
| 166 | / | 472.2992 | 9.40 | 1 | + | + | + | + |
| 167 | / | 405.2186 | 9.63 | 2 | + | + | + | + |
| 168 | / | 421.7331 | 9.63 | 2 | + | + | + | + |
| 169 | / | 498.7538 | 9.63 | 2 | + | + | + | + |
| 170 | / | 402.2567 | 10.08 | 1 | + | + | + | + |
| 171 | / | 444.2303 | 10.08 | 2 | + | + | + | + |
| 172 | / | 469.2535 | 10.08 | 2 | + | + | - | - |
| 173 | / | 474.2429 | 10.08 | 1 | + | + | + | + |
| 174 | / | 405.2085 | 10.36 | | + | + | - | - |
| 175 | / | 418.7339 | 10.36 | 2 | + | + | + | + |
| 176 | / | 448.2467 | 10.36 | 2 | + | + | + | + |
| 177 | / | 475.7502 | 10.57 | 2 | + | + | + | + |
| 178 | / | 434.7471 | 10.81 | 2 | + | + | + | + |
| 179 | / | 411.2322 | 10.98 | 1 | + | + | + | + |
| 180 | / | 427.7393 | 10.98 | 2 | + | + | - | - |
| 181 | / | 459.2678 | 10.98 | 1 | + | + | + | + |
| 182 | / | 427.7383 | 11.01 | 2 | + | + | - | - |
| 183 | / | 467.7517 | 11.01 | 2 | + | + | + | + |
| 184 | / | 461.2554 | 11.46 | 2 | + | + | - | - |
| 185 | / | 446.7472 | 11.52 | 2 | + | + | + | + |

FIG. 10 (Continued)

| 186 | / | 468.2369 | 11.52 | 1 | + | + | + | + |
| --- | --- | --- | --- | --- | --- | --- | --- | --- |
| 187 | / | 474.2428 | 11.52 | 1 | + | + | + | + |
| 188 | / | 458.2476 | 12.10 | 2 | + | + | + | + |
| 189 | / | 492.5855 | 12.10 | 3 | + | + | - | - |
| 190 | / | 406.2358 | 12.21 | 2 | + | + | + | + |
| 191 | / | 464.7522 | 12.26 | 2 | + | + | + | + |
| 192 | / | 414.2457 | 12.27 | 1 | + | + | + | + |
| 193 | / | 442.7441 | 12.27 | 2 | + | + | + | + |
| 194 | / | 453.2203 | 12.27 |   | + | + | + | + |
| 195 | / | 457.7509 | 12.27 | 2 | + | + | + | + |
| 196 | / | 459.1892 | 12.27 | 2 | + | + | + | + |
| 197 | / | 474.2679 | 12.27 | 2 | + | + | + | + |
| 198 | / | 474.2682 | 12.27 | 1 | + | + | + | + |
| 199 | / | 476.2476 | 12.35 | 2 | + | + | + | + |
| 200 | / | 421.2412 | 12.45 | 2 | + | + | + | + |
| 201 | / | 400.2298 | 12.78 | 2 | + | + | + | + |
| 202 | / | 430.2411 | 12.78 | 1 | + | + | + | + |
| 203 | / | 479.7979 | 12.78 | 2 | + | + | + | + |
| 204 | / | 471.7388 | 12.84 | 2 | + | + | + | + |
| 205 | / | 420.1979 | 13.01 | 1 | + | + | + | + |
| 206 | / | 469.2711 | 13.03 | 2 | + | + | - | - |

FIG. 10 (Continued)

| | | | | | | | |
|---|---|---|---|---|---|---|---|
| 207 | / | 456.2456 | 13.15 | 2 | + | + | + | + |
| 208 | / | 406.2352 | 13.25 | 2 | + | + | + | - |
| 209 | / | 472.2880 | 13.31 | 1 | + | + | + | + |
| 210 | / | 431.2253 | 13.59 | 2 | + | + | + | + |
| 211 | / | 447.2085 | 13.59 | 1 | + | + | + | + |
| 212 | / | 478.7565 | 13.59 | 2 | + | + | + | + |
| 213 | / | 454.7644 | 13.80 | 2 | + | + | + | + |
| 214 | / | 464.2263 | 13.90 | 1 | + | + | + | + |
| 215 | / | 413.2410 | 14.18 | 2 | + | + | + | + |
| 216 | / | 499.2998 | 14.24 | 1 | + | + | - | - |
| 217 | / | 414.2108 | 14.52 | 2 | + | + | - | - |
| 218 | / | 447.2542 | 14.60 | 1 | + | + | + | + |
| 219 | / | 486.3042 | 14.60 | 1 | + | + | + | + |
| 220 | / | 446.7659 | 14.62 | 2 | + | + | + | + |
| 221 | / | 486.3052 | 14.62 | 1 | + | + | + | + |
| 222 | / | 414.2413 | 14.88 | 3 | + | + | + | + |
| 223 | / | 457.2030 | 14.88 | 2 | + | + | + | + |
| 224 | / | 465.2464 | 14.88 | 1 | + | + | + | + |
| 225 | / | 403.2657 | 15.00 | 1 | + | + | + | + |
| 226 | / | 410.8747 | 15.00 | 3 | + | + | + | + |
| 227 | / | 415.8626 | 15.00 | 3 | + | + | + | + |

FIG. 10 (Continued)

| | | | | | | | |
|---|---|---|---|---|---|---|---|
| 228 | / | 421.2612 | 15.00 | 2 | + | + | + | + |
| 229 | / | 412.2540 | 15.75 | 2 | + | + | + | + |
| 230 | / | 407.2195 | 15.76 | 2 | + | + | + | + |
| 231 | / | 403.2657 | 16.04 | 1 | + | + | - | - |
| 232 | / | 412.2536 | 16.04 | 2 | + | + | + | + |
| 233 | / | 449.7704 | 16.48 | 2 | + | + | + | + |
| 234 | / | 478.2575 | 16.50 | 2 | + | + | - | + |
| 235 | / | 446.2722 | 16.69 | 1 | + | + | + | + |
| 236 | / | 434.2619 | 17.34 | 2 | + | + | + | + |
| 237 | / | 479.2622 | 17.50 | 1 | + | + | + | + |
| 238 | / | 418.2195 | 17.95 | 1 | + | + | + | + |
| 239 | / | 467.7294 | 17.95 | 2 | + | + | + | + |
| 240 | / | 473.2079 | 18.21 | 2 | + | + | + | + |
| 241 | / | 441.7730 | 18.54 | 2 | + | + | + | + |
| 242 | / | 460.4769 | 18.89 | 4 | + | + | - | - |
| 243 | / | 464.4752 | 18.89 | 4 | + | + | - | - |
| 244 | / | 472.5596 | 18.89 | 3 | + | + | + | + |
| 245 | / | 476.2273 | 18.89 | 1 | + | + | + | + |
| 246 | / | 462.2472 | 19.19 | 1 | + | + | + | + |
| 247 | / | 493.2424 | 19.19 | 1 | + | + | + | + |
| 248 | / | 455.2042 | 19.61 | 1 | + | + | + | + |

FIG. 10 (Continued)

| 249 | / | 404.4604 | 19.63 | 4 | + | + | + | + |
|---|---|---|---|---|---|---|---|---|
| 250 | / | 407.9573 | 19.63 | 4 | + | + | + | + |
| 251 | / | 411.6992 | 19.63 | 4 | + | + | + | + |
| 252 | / | 446.5774 | 19.63 | 3 | + | + | - | - |
| 253 | / | 459.2278 | 19.63 | 3 | + | + | + | + |
| 254 | / | 421.2432 | 20.13 | 2 | + | + | + | + |
| 255 | / | 441.2521 | 20.49 | 2 | + | + | + | + |
| 256 | / | 444.2936 | 20.49 | 1 | + | + | + | + |
| 257 | / | 430.2775 | 20.63 | 1 | + | + | + | + |
| 258 | / | 429.2826 | 21.01 | 1 | + | + | + | + |
| 259 | / | 499.7645 | 21.01 | 2 | + | + | + | + |
| 260 | / | 472.2893 | 21.02 | 1 | + | + | + | + |
| 261 | / | 488.7716 | 21.02 | 2 | + | + | - | - |
| 262 | / | 413.2866 | 21.76 | 1 | + | + | + | + |
| 263 | / | 480.2565 | 21.76 | 1 | + | + | + | + |
| 264 | / | 431.5276 | 21.95 | 3 | + | + | + | + |
| 265 | / | 459.2935 | 21.96 | 1 | + | + | + | + |
| 266 | / | 451.2280 | 22.27 | 1 | + | + | + | + |
| 267 | / | 429.2457 | 22.30 | 1 | + | + | + | + |
| 268 | / | 402.5164 | 22.63 | 3 | + | + | + | + |
| 269 | / | 415.2447 | 22.63 | 1 | + | + | + | + |

FIG. 10 (Continued)

| | | | | | | | |
|---|---|---|---|---|---|---|---|
| 270 | / | 480.7737 | 22.63 | 2 | + | + | - | - |
| 271 | / | 491.7648 | 22.63 | 2 | + | + | - | - |
| 272 | / | 456.2925 | 23.26 | 1 | + | + | + | + |
| 273 | / | 437.7673 | 31.77 | 2 | + | + | + | + |
| 274 | / | 526.2750 | 5.31 | 1 | + | + | + | + |
| 275 | / | 573.2644 | 5.31 | 1 | + | + | + | + |
| 276 | / | 578.2752 | 5.31 | 1 | + | + | + | + |
| 277 | / | 558.3128 | 5.59 | | + | + | + | + |
| 278 | / | 501.2429 | 6.30 | 1 | + | + | + | + |
| 279 | / | 534.2432 | 6.30 | 1 | + | + | + | + |
| 280 | / | 568.2868 | 6.30 | 1 | + | + | + | + |
| 281 | / | 584.3129 | 6.30 | | + | + | + | + |
| 282 | / | 515.3429 | 10.06 | 1 | + | + | + | + |
| 283 | / | 569.7932 | 10.06 | 2 | + | + | + | + |
| 284 | / | 581.3193 | 11.52 | 1 | + | + | + | + |
| 285 | / | 527.2957 | 12.10 | 1 | + | + | + | + |
| 286 | / | 570.3125 | 12.10 | 1 | + | + | + | + |
| 287 | / | 583.8135 | 12.10 | 2 | + | + | + | + |
| 288 | / | 596.3298 | 12.10 | 1 | + | + | + | + |
| 289 | / | 531.2907 | 12.27 | 1 | + | + | + | + |
| 290 | / | 571.2819 | 12.27 | 1 | + | + | + | + |

FIG. 10 (Continued)

| | | | | | | | |
|---|---|---|---|---|---|---|---|
| 291 | / | 578.3000 | 12.27 | 2 | + | + | + | + |
| 292 | / | 536.7798 | 12.35 | 2 | + | + | + | - |
| 293 | / | 544.2973 | 12.40 | 1 | + | + | + | + |
| 294 | / | 589.2899 | 12.40 | 3 | + | + | - | + |
| 295 | / | 504.7541 | 12.50 | 2 | + | + | + | - |
| 296 | / | 578.3056 | 12.53 | 1 | + | + | + | + |
| 297 | / | 556.3212 | 12.55 | 1 | + | + | + | + |
| 298 | / | 552.6142 | 12.58 | 3 | + | + | + | + |
| 299 | / | 538.2274 | 12.65 | 2 | + | + | + | + |
| 300 | / | 531.7855 | 12.78 | 2 | + | + | + | + |
| 301 | / | 562.2794 | 12.78 | 1 | + | + | + | + |
| 302 | / | 531.7965 | 13.21 | 2 | + | + | - | - |
| 303 | / | 556.6228 | 13.31 | 3 | + | + | - | - |
| 304 | / | 560.3174 | 13.31 | 1 | + | + | + | + |
| 305 | / | 553.7987 | 13.56 | 2 | + | + | + | + |
| 306 | / | 514.2510 | 13.59 | 2 | + | + | - | + |
| 307 | / | 553.3052 | 13.59 | 2 | + | + | + | + |
| 308 | / | 579.7647 | 13.59 | 2 | + | + | + | + |
| 309 | / | 564.2942 | 13.60 | 2 | + | + | + | + |
| 310 | / | 572.2779 | 13.60 | 2 | + | + | + | + |
| 311 | / | 577.8215 | 13.75 | 2 | + | + | - | - |

FIG. 10 (Continued)

| | | | | | | | |
|---|---|---|---|---|---|---|---|
| 312 | / | 599.8293 | 14.00 | 2 | + | + | - | - |
| 313 | / | 535.2696 | 14.08 | 1 | + | + | + | + |
| 314 | / | 587.1737 | 14.08 | 1 | + | + | + | + |
| 315 | / | 550.7959 | 14.24 | 2 | + | + | + | + |
| 316 | / | 542.7990 | 14.46 | 2 | + | + | + | + |
| 317 | / | 545.3081 | 14.46 | 2 | + | + | + | + |
| 318 | / | 555.7896 | 14.46 | 2 | + | + | - | - |
| 319 | / | 569.6130 | 14.46 | 3 | + | + | + | + |
| 320 | / | 573.2504 | 14.46 | 2 | + | + | + | + |
| 321 | / | 575.3018 | 14.46 | 2 | + | + | + | + |
| 322 | / | 583.6149 | 14.46 | 3 | + | + | - | + |
| 323 | / | 594.2725 | 14.46 | 2 | + | + | + | + |
| 324 | / | 539.7992 | 14.82 | 2 | + | + | - | - |
| 325 | / | 591.8301 | 14.95 | 2 | + | + | - | - |
| 326 | / | 596.8323 | 14.97 | 2 | + | + | + | + |
| 327 | / | 579.6278 | 15.28 | 3 | + | + | - | - |
| 328 | / | 585.3025 | 15.28 | 1 | + | + | - | - |
| 329 | / | 589.3338 | 15.44 | 1 | + | + | + | + |
| 330 | / | 508.2906 | 15.50 | 1 | + | + | + | + |
| 331 | / | 564.2834 | 15.75 | 1 | + | + | + | + |
| 332 | / | 517.6038 | 16.04 | 3 | + | + | - | + |

FIG. 10 (Continued)

| | | | | | | | | |
|---|---|---|---|---|---|---|---|---|
| 333 | / | 546.7834 | 16.04 | 2 | + | + | + | + |
| 334 | / | 588.8368 | 16.04 | 2 | + | + | + | + |
| 335 | / | 587.3193 | 16.26 | 1 | + | + | + | - |
| 336 | / | 586.3359 | 16.42 | 1 | + | + | + | + |
| 337 | / | 512.2539 | 16.68 | 2 | + | + | + | + |
| 338 | / | 544.7864 | 16.68 | 2 | + | + | + | + |
| 339 | / | 510.2391 | 16.77 | 2 | + | + | + | + |
| 340 | / | 556.7927 | 17.20 | 2 | + | + | + | + |
| 341 | / | 538.7866 | 17.27 | 2 | + | + | + | + |
| 342 | / | 544.7866 | 17.43 | 2 | + | + | + | + |
| 343 | / | 581.8293 | 17.50 | 2 | + | + | + | + |
| 344 | / | 535.8036 | 17.75 | 2 | + | + | + | + |
| 345 | / | 524.8132 | 17.94 | 2 | + | + | + | - |
| 346 | / | 563.8012 | 17.94 | 2 | + | + | + | + |
| 347 | / | 532.2520 | 18.39 | 2 | + | + | - | - |
| 348 | / | 530.7887 | 18.89 | 2 | + | + | + | + |
| 349 | 1 | 518.2695 | 18.92 | 4 | + | - | - | - |
| 350 | / | 509.7630 | 19.19 | 2 | + | + | + | + |
| 351 | / | 543.3277 | 19.19 | 1 | + | + | - | - |
| 352 | / | 565.3103 | 19.19 | 1 | + | + | - | - |
| 353 | / | 529.6020 | 19.40 | 3 | + | + | + | + |

FIG. 10 (Continued)

| | | | | | | | |
|---|---|---|---|---|---|---|---|
| 354 | / | 515.2510 | 19.50 | 2 | + | + | + | + |
| 355 | / | 512.5736 | 19.63 | 3 | + | + | + | + |
| 356 | / | 530.9570 | 19.63 | 3 | + | + | + | + |
| 357 | / | 538.2836 | 19.63 | 3 | + | + | + | + |
| 358 | / | 543.6046 | 19.63 | 3 | + | + | + | + |
| 359 | / | 548.9296 | 19.63 | 3 | + | + | + | + |
| 360 | / | 581.2635 | 19.63 | 2 | + | + | + | + |
| 361 | / | 507.7421 | 19.80 | 2 | + | + | + | + |
| 362 | / | 511.7312 | 19.81 | 2 | + | + | + | + |
| 363 | / | 518.7344 | 19.81 | 2 | + | + | + | + |
| 364 | / | 526.7177 | 19.81 | 2 | + | + | + | + |
| 365 | / | 534.1999 | 19.81 | 2 | + | + | + | + |
| 366 | / | 571.3244 | 19.81 | 1 | + | + | + | - |
| 367 | / | 528.9272 | 20.10 | 3 | + | + | + | - |
| 368 | / | 510.9530 | 20.13 | 3 | + | + | - | - |
| 369 | / | 523.6025 | 20.13 | 3 | + | + | - | - |
| 370 | / | 528.5910 | 20.13 | 3 | + | + | - | - |
| 371 | / | 595.6501 | 20.13 | 3 | + | + | - | - |
| 372 | / | 518.2789 | 20.15 | 3 | + | + | - | - |
| 373 | / | 513.7482 | 20.49 | 2 | + | + | + | + |
| 374 | / | 598.3134 | 20.60 | 2 | + | + | - | - |

FIG. 10 (Continued)

| | | | | | | | |
|---|---|---|---|---|---|---|---|
| 375 | / | 535.6320 | 21.32 | 3 | + | + | - | - |
| 376 | / | 591.8236 | 21.95 | 2 | + | + | + | - |
| 377 | / | 599.3923 | 22.27 | 1 | + | + | + | + |
| 378 | / | 573.3398 | 23.14 | 1 | + | + | + | + |
| 379 | / | 511.2845 | 23.66 | 2 | + | + | + | + |
| 380 | / | 501.7630 | 24.02 | 2 | + | + | + | + |
| 381 | / | 512.7552 | 24.02 | 2 | + | + | + | + |
| 382 | / | 520.7371 | 24.02 | 2 | + | + | + | + |
| 383 | / | 561.3171 | 24.91 | 1 | + | + | + | + |
| 384 | / | 572.3803 | 25.69 | 1 | + | + | + | + |
| 385 | / | 544.3862 | 26.81 | 1 | + | + | + | + |
| 386 | / | 547.7753 | 27.08 | 2 | + | + | + | + |
| 387 | / | 558.7653 | 27.09 | 2 | + | + | + | + |
| 388 | / | 574.2337 | 27.09 | 2 | + | + | + | + |
| 389 | / | 539.7781 | 28.50 | 2 | + | + | + | + |
| 390 | / | 602.3390 | 8.27 | 1 | + | + | + | + |
| 391 | / | 604.3075 | 9.40 | 1 | + | + | + | + |
| 392 | / | 644.3510 | 10.06 | 1 | + | + | + | + |
| 393 | / | 677.3781 | 10.98 | 1 | + | + | + | + |
| 394 | / | 694.4061 | 11.52 | 1 | + | + | + | + |
| 395 | / | 628.3564 | 12.10 | 2 | + | + | + | + |

FIG. 10 (Continued)

| | | | | | | | |
|---|---|---|---|---|---|---|---|
| 396 | / | 604.2905 | 12.35 | 1 | + | + | + | + |
| 397 | / | 618.3392 | 12.35 | 1 | + | + | + | + |
| 398 | / | 600.2304 | 12.78 | | + | + | + | + |
| 399 | / | 629.8132 | 12.78 | 2 | + | + | + | + |
| 400 | / | 655.3930 | 13.03 | 1 | + | + | + | + |
| 401 | / | 696.8466 | 13.03 | 2 | + | + | + | - |
| 402 | / | 666.8469 | 13.20 | 2 | + | + | + | + |
| 403 | / | 618.3262 | 13.31 | 2 | + | + | - | - |
| 404 | / | 602.2936 | 14.24 | 1 | + | + | + | + |
| 405 | / | 655.8360 | 14.50 | 2 | + | + | + | - |
| 406 | / | 690.8569 | 14.62 | 2 | + | + | - | - |
| 407 | / | 607.8255 | 14.80 | 2 | + | + | + | + |
| 408 | / | 660.3497 | 15.00 | 2 | + | + | + | + |
| 409 | / | 655.3567 | 15.28 | 1 | + | + | - | + |
| 410 | / | 607.2546 | 15.50 | 1 | + | + | + | + |
| 411 | / | 670.3497 | 15.50 | 2 | + | + | + | + |
| 412 | / | 624.3507 | 15.75 | 1 | + | + | + | + |
| 413 | / | 643.3687 | 16.42 | 1 | + | + | + | + |
| 414 | / | 614.6549 | 16.68 | 3 | + | + | - | - |
| 415 | / | 608.3549 | 16.74 | 1 | + | + | + | + |
| 416 | / | 654.3494 | 16.74 | 2 | + | + | - | - |

FIG. 10 (Continued)

| | | | | | | | |
|---|---|---|---|---|---|---|---|
| 417 | / | 644.8290 | 16.75 | 2 | + | + | + | - |
| 418 | / | 602.3176 | 17.10 | 3 | + | + | - | + |
| 419 | / | 621.9774 | 17.10 | 3 | + | + | + | - |
| 420 | / | 662.3516 | 17.34 | 2 | + | + | + | + |
| 421 | / | 609.8244 | 17.75 | 2 | + | + | + | + |
| 422 | / | 647.3307 | 17.75 | 1 | + | + | + | + |
| 423 | / | 654.3328 | 17.94 | 2 | + | + | + | + |
| 424 | / | 601.3122 | 18.39 | 2 | + | + | + | + |
| 425 | / | 600.9833 | 18.89 | 3 | + | + | - | - |
| 426 | / | 649.3496 | 18.89 | 3 | + | + | - | - |
| 427 | / | 672.3542 | 18.90 | 2 | + | + | + | + |
| 428 | / | 698.3878 | 19.19 | 1 | + | + | - | - |
| 429 | / | 607.2905 | 19.63 | 1 | + | + | + | + |
| 430 | / | 669.3605 | 19.63 | 2 | + | + | - | - |
| 431 | / | 649.3000 | 19.82 | 1 | + | + | + | + |
| 432 | / | 672.8430 | 20.00 | 2 | + | + | + | + |
| 433 | / | 648.3511 | 20.10 | 2 | + | + | + | + |
| 434 | / | 600.3867 | 20.13 | 1 | + | + | + | + |
| 435 | / | 635.3197 | 20.13 | 1 | + | + | - | - |
| 436 | / | 688.4038 | 20.13 | 1 | + | + | + | + |
| 437 | / | 683.8020 | 20.49 | 2 | + | + | + | + |

FIG. 10 (Continued)

| | | | | | | | |
|---|---|---|---|---|---|---|---|
| 438 | / | 664.8443 | 20.70 | 2 | + | + | + | + |
| 439 | / | 661.3627 | 20.80 | 2 | + | + | - | - |
| 440 | / | 621.3747 | 21.95 | 1 | + | + | + | + |
| 441 | / | 646.7862 | 21.95 | 2 | + | + | + | + |
| 442 | / | 656.8466 | 21.95 | 2 | + | + | + | + |
| 443 | / | 603.2689 | 22.63 | 2 | + | + | + | + |
| 444 | / | 649.3232 | 22.63 | 2 | + | + | + | + |
| 445 | / | 623.8404 | 23.30 | 2 | + | + | - | - |
| 446 | / | 641.3310 | 23.36 | 2 | + | + | + | + |
| 447 | / | 648.8497 | 23.36 | 2 | + | + | + | + |
| 448 | / | 670.4318 | 23.36 | 1 | + | + | + | + |
| 449 | 2 | 675.6632 | 23.36 | 3 | + | - | - | - |
| 450 | / | 656.4151 | 23.66 | 1 | + | + | - | - |
| 451 | / | 676.8740 | 26.90 | 2 | + | + | - | - |
| 452 | / | 745.3828 | 5.59 | | + | + | + | + |
| 453 | / | 767.4245 | 8.27 | 1 | + | + | + | - |
| 454 | / | 771.3333 | 10.39 | 1 | + | + | + | + |
| 455 | / | 785.4468 | 10.98 | 1 | + | + | + | - |
| 456 | / | 726.3605 | 11.86 | 1 | + | + | + | + |
| 457 | / | 780.7086 | 11.86 | 3 | + | + | - | - |
| 458 | / | 773.3523 | 12.10 | | + | + | + | + |

FIG. 10 (Continued)

| | | | | | | | |
|---|---|---|---|---|---|---|---|
| 459 | / | 748.3914 | 12.40 | 1 | + | + | + | + |
| 460 | / | 731.8613 | 12.90 | 2 | + | + | - | + |
| 461 | / | 762.8742 | 13.03 | 2 | + | + | - | + |
| 462 | / | 783.4554 | 13.03 | 1 | + | + | + | + |
| 463 | / | 723.3107 | 13.49 | 1 | + | + | + | + |
| 464 | / | 746.8769 | 13.70 | 2 | + | + | - | - |
| 465 | / | 763.8432 | 13.80 | 2 | + | + | - | - |
| 466 | / | 724.3671 | 13.88 | 2 | + | + | - | + |
| 467 | / | 766.7067 | 13.88 | 3 | + | + | + | + |
| 468 | / | 708.6879 | 14.08 | 3 | + | + | + | + |
| 469 | / | 718.2710 | 14.08 | 1 | + | + | + | + |
| 470 | / | 703.3402 | 14.46 | 2 | + | + | + | + |
| 471 | / | 761.0394 | 14.46 | 3 | + | + | + | + |
| 472 | / | 778.3712 | 14.88 | 2 | + | + | + | + |
| 473 | / | 749.0318 | 14.89 | 3 | + | + | + | + |
| 474 | / | 753.8639 | 14.89 | 2 | + | + | + | + |
| 475 | / | 767.7089 | 14.89 | 3 | + | + | + | - |
| 476 | / | 755.7079 | 15.33 | 3 | + | + | + | + |
| 477 | / | 710.8729 | 15.35 | 2 | + | + | + | + |
| 478 | / | 745.8657 | 15.95 | 2 | + | + | - | + |
| 479 | / | 775.9012 | 16.04 | 2 | + | + | - | + |

FIG. 10 (Continued)

| | | | | | | | |
|---|---|---|---|---|---|---|---|
| 480 | / | 798.9020 | 16.04 | 2 | + | + | - | + |
| 481 | / | 733.3679 | 16.20 | 2 | + | + | - | - |
| 482 | / | 730.3692 | 16.42 | 2 | + | + | + | + |
| 483 | / | 760.8886 | 16.89 | 2 | + | + | - | - |
| 484 | / | 732.3417 | 17.04 | 1 | + | + | + | + |
| 485 | / | 723.7094 | 17.26 | 3 | + | + | + | - |
| 486 | / | 724.0438 | 17.34 | 3 | + | + | + | - |
| 487 | / | 718.7115 | 18.11 | 3 | + | + | + | - |
| 488 | / | 792.8801 | 18.34 | 2 | + | + | + | + |
| 489 | / | 737.6915 | 18.80 | 3 | + | + | - | - |
| 490 | / | 708.3562 | 18.89 | 2 | + | + | + | + |
| 491 | / | 713.0401 | 19.05 | 3 | + | + | + | - |
| 492 | / | 793.8986 | 19.40 | 2 | + | + | + | + |
| 493 | / | 795.9306 | 19.61 | 2 | + | + | + | + |
| 494 | / | 785.8968 | 19.81 | 2 | + | + | + | + |
| 495 | / | 765.9196 | 20.10 | 2 | + | + | + | - |
| 496 | / | 726.3114 | 20.13 | 2 | + | + | + | + |
| 497 | / | 765.9238 | 20.13 | 2 | + | + | - | - |
| 498 | / | 776.9109 | 20.13 | 2 | + | + | - | - |
| 499 | / | 784.8969 | 20.13 | 2 | + | + | + | + |
| 500 | / | 761.0683 | 20.49 | 3 | + | + | - | - |

FIG. 10 (Continued)

| | | | | | | | |
|---|---|---|---|---|---|---|---|
| 501 | / | 705.8646 | 21.52 | 2 | + | + | + | - |
| 502 | / | 753.3849 | 21.52 | 2 | + | + | - | - |
| 503 | / | 781.9374 | 21.52 | 2 | + | + | + | + |
| 504 | / | 728.4091 | 22.27 | 2 | + | + | - | - |
| 505 | / | 781.9127 | 22.43 | 2 | + | + | + | + |
| 506 | 4 | 766.6952 | 23.36 | 3 | + | - | - | - |
| 507 | 5 | 774.0218 | 23.36 | 3 | + | - | - | - |
| 508 | 6 | 784.3392 | 23.36 | 3 | + | - | - | - |
| 509 | / | 786.4556 | 23.66 | 1 | + | + | - | - |
| 510 | 3 | 761.3672 | 24.24 | 3 | + | - | - | - |
| 511 | / | 757.4285 | 24.97 | 1 | + | + | + | - |
| 512 | / | 868.4834 | 10.62 | 1 | + | + | + | + |
| 513 | / | 800.3909 | 11.86 | 2 | + | + | + | - |
| 514 | / | 811.4634 | 12.10 | 1 | + | + | + | + |
| 515 | / | 811.4623 | 12.27 | 1 | + | + | + | + |
| 516 | / | 928.4948 | 12.27 | 1 | + | + | + | + |
| 517 | / | 811.4610 | 12.30 | 1 | + | + | + | + |
| 518 | / | 883.4320 | 12.40 | 2 | + | + | - | + |
| 519 | / | 937.5318 | 13.03 | 1 | + | + | - | - |
| 520 | / | 811.4614 | 13.13 | 1 | + | + | + | - |
| 521 | / | 811.4615 | 13.20 | 1 | + | + | + | - |

FIG. 10 (Continued)

| | | | | | | | |
|---|---|---|---|---|---|---|---|
| 522 | / | 804.8810 | 13.59 | 2 | + | + | + | + |
| 523 | / | 854.4121 | 14.46 | 2 | + | + | + | + |
| 524 | / | 874.9170 | 14.46 | 2 | + | + | - | + |
| 525 | / | 892.5215 | 14.62 | 1 | + | + | + | + |
| 526 | / | 868.9328 | 14.88 | 2 | + | + | - | - |
| 527 | / | 845.9125 | 15.33 | 2 | + | + | + | + |
| 528 | / | 813.4302 | 15.75 | 1 | + | + | + | + |
| 529 | / | 823.5000 | 15.75 | 1 | + | + | + | - |
| 530 | / | 816.4244 | 16.24 | 2 | + | + | + | + |
| 531 | / | 898.5327 | 16.42 | 1 | + | + | + | + |
| 532 | / | 825.9096 | 16.49 | 2 | + | + | - | - |
| 533 | / | 921.4785 | 16.68 | 2 | + | + | - | - |
| 534 | / | 852.4311 | 17.04 | 1 | + | + | + | + |
| 535 | / | 834.7436 | 17.43 | 3 | + | + | + | + |
| 536 | / | 934.4512 | 17.75 | 1 | + | + | + | + |
| 537 | / | 874.7801 | 17.92 | 3 | + | + | + | + |
| 538 | / | 804.3942 | 18.11 | 2 | + | + | - | + |
| 539 | / | 811.7179 | 18.34 | 3 | + | + | + | + |
| 540 | / | 900.9699 | 18.89 | 2 | + | + | - | - |
| 541 | / | 829.4146 | 19.19 | 2 | + | + | - | - |
| 542 | / | 824.4354 | 19.63 | 2 | + | + | + | + |

FIG. 10 (Continued)

| | | | | | | | |
|---|---|---|---|---|---|---|---|
| 543 | / | 892.9678 | 20.00 | 2 | + | + | - | - |
| 544 | / | 841.4766 | 20.13 | 1 | + | + | + | + |
| 545 | / | 821.4173 | 20.49 | 2 | + | + | - | - |
| 546 | / | 850.4249 | 21.02 | 3 | + | + | + | + |
| 547 | / | 976.5327 | 21.02 | 1 | + | + | - | - |
| 548 | / | 821.3904 | 21.20 | 1 | + | + | + | + |
| 549 | / | 802.9475 | 21.40 | 2 | + | + | - | - |
| 550 | / | 845.4240 | 22.27 | 3 | + | + | + | + |
| 551 | / | 960.5383 | 22.63 | 1 | + | + | - | - |
| 552 | / | 844.4641 | 23.36 | 1 | + | + | + | - |
| 553 | / | 926.5504 | 23.66 | 1 | + | + | + | + |
| 554 | 7 | 854.0603 | 27.08 | 3 | + | - | - | - |
| 555 | / | 874.5250 | 31.78 | 1 | + | + | + | + |
| 556 | / | 1008.4980 | 12.55 | 1 | + | + | + | - |
| 557 | / | 1027.4908 | 13.59 | 1 | + | + | - | + |
| 558 | / | 1105.5997 | 13.59 | 1 | + | + | + | + |
| 559 | / | 1149.5944 | 14.46 | 1 | + | + | + | + |
| 560 | / | 1078.5911 | 14.88 | 1 | + | + | - | - |
| 561 | / | 1192.6607 | 15.00 | 1 | + | + | + | + |
| 562 | / | 1092.5548 | 16.04 | 1 | + | + | + | + |
| 563 | / | 1088.5613 | 17.34 | 1 | + | + | + | + |

FIG. 10 (Continued)

| 564 | / | 1018.5114 | 19.19 | 1 | + | + | + | + |
| 565 | / | 1029.4871 | 19.50 | 1 | + | + | + | + |
| 566 | / | 1014.4776 | 19.81 | 1 | + | + | + | + |
| 567 | 4 | 1150.0642 | 23.40 | 2 | + | - | - | - |
| 568 | / | 1021.5555 | 23.66 |   | + | + | + | + |
| 569 | / | 1094.5447 | 27.08 | 1 | + | + | + | + |

FIG. 10 (Continued)

Table 2

| Horse marker No. | m/z | RT (min) | Charge | Donkey | Horse | Cattle | Pig |
|---|---|---|---|---|---|---|---|
| / | 189.1288 | 5.31 | 1 | + | + | + | + |
| / | 216.6198 | 8.26 | 2 | + | + | + | + |
| / | 219.1404 | 10.98 | 1 | + | + | + | + |
| / | 223.1141 | 8.27 | 1 | + | + | + | + |
| / | 224.1352 | 31.00 | 1 | + | + | + | + |
| / | 228.6384 | 5.31 | 2 | + | + | + | + |
| / | 229.6280 | 12.09 | 2 | + | + | + | + |
| / | 231.1762 | 10.44 | 1 | + | + | + | + |
| / | 231.1771 | 7.77 |   | + | + | + | + |
| / | 233.1565 | 5.55 | 1 | + | + | + | + |
| / | 234.1024 | 22.27 |   | + | + | + | + |

FIG. 11

| | | | | | | | |
|---|---|---|---|---|---|---|---|
| / | 236.6544 | 9.34 | 2 | + | + | + | + |
| / | 237.6260 | 10.08 | 2 | + | + | + | + |
| / | 237.6447 | 5.31 | 2 | + | + | + | + |
| / | 242.1565 | 10.08 | 1 | + | + | + | + |
| / | 243.1408 | 15.75 | 1 | + | + | + | + |
| / | 245.1925 | 14.24 | 1 | + | + | + | + |
| / | 245.1925 | 15.38 | 1 | + | + | + | + |
| / | 249.6631 | 10.08 | 2 | + | + | + | + |
| / | 250.1855 | 32.78 | 1 | + | + | + | + |
| / | 258.1766 | 10.10 | 2 | + | + | + | + |
| / | 260.1678 | 9.58 | 1 | + | + | + | + |
| / | 260.2043 | 6.27 | 1 | + | + | + | + |
| / | 265.1621 | 13.32 | 1 | + | + | + | + |
| / | 267.6266 | 6.27 | 2 | + | + | + | + |
| / | 270.2001 | 10.08 | 1 | + | + | + | + |
| / | 272.1795 | 9.40 | 1 | + | + | + | + |
| / | 272.6535 | 12.27 | 2 | + | + | + | + |
| / | 274.1954 | 10.08 | 1 | + | + | + | + |
| / | 276.1632 | 7.57 | 1 | + | + | + | + |
| / | 277.1257 | 9.74 | 1 | + | + | + | + |
| / | 278.6662 | 12.50 | 2 | + | + | + | + |

FIG. 11 (Continued)

| | | | | | | | |
|---|---|---|---|---|---|---|---|
| / | 279.1418 | 17.53 | 1 | + | + | + | + |
| / | 279.1777 | 18.20 | 1 | + | + | + | + |
| / | 281.1213 | 10.08 | 1 | + | + | + | + |
| / | 281.1566 | 5.59 | 1 | + | + | + | + |
| / | 283.8095 | 12.27 | 2 | + | + | + | + |
| / | 288.2009 | 20.49 | / | + | + | + | + |
| / | 288.2116 | 6.30 | / | + | + | + | + |
| / | 290.1784 | 6.30 | / | + | + | + | + |
| / | 292.6630 | 12.27 | 2 | + | + | + | + |
| / | 295.1730 | 10.98 | 1 | + | + | + | + |
| / | 295.1740 | 10.08 | 1 | + | + | + | + |
| / | 297.6402 | 12.50 | 2 | + | + | + | + |
| / | 300.6175 | 12.78 | 2 | + | + | + | + |
| / | 301.1832 | 6.30 | 2 | + | + | + | + |
| / | 301.6758 | 8.27 | 2 | + | + | + | + |
| / | 301.6768 | 14.24 | 2 | + | + | + | + |
| / | 302.1801 | 10.08 | 1 | + | + | + | + |
| / | 302.2159 | 19.22 | 1 | + | + | + | + |
| / | 302.2166 | 18.21 | 1 | + | + | + | + |
| / | 303.6207 | 6.30 | 1 | + | + | + | + |
| / | 305.6956 | 11.52 | 2 | + | + | + | + |

FIG. 11 (Continued)

| / | 306.1484 | 23.08 | 2 | + | + | + | + |
|---|---|---|---|---|---|---|---|
| / | 306.1739 | 6.30 |   | + | + | + | + |
| / | 309.6738 | 12.35 | 2 | + | + | + | + |
| / | 312.8329 | 16.42 | 3 | + | + | + | + |
| / | 314.6831 | 12.07 | 2 | + | + | + | + |
| / | 314.7013 | 11.46 | 2 | + | + | + | - |
| / | 316.2312 | 19.63 | 1 | + | + | + | + |
| / | 317.1910 | 6.30 | 3 | + | + | + | + |
| / | 320.1733 | 14.88 | 1 | + | + | + | + |
| / | 320.1866 | 8.27 | 1 | + | + | + | - |
| / | 320.2031 | 12.78 | 3 | + | + | + | + |
| / | 321.1797 | 13.31 | 2 | + | + | + | - |
| / | 321.1817 | 5.59 | 1 | + | + | + | + |
| / | 322.6805 | 10.06 | 2 | + | + | + | + |
| / | 322.8205 | 12.27 | 3 | + | + | + | + |
| / | 323.1587 | 6.30 |   | + | + | + | + |
| / | 323.4940 | 6.30 |   | + | + | + | + |
| / | 324.1811 | 5.59 | 2 | + | + | + | + |
| / | 325.6760 | 8.17 | 2 | + | + | - | - |
| / | 327.8098 | 12.27 | 3 | + | + | + | + |
| / | 329.1909 | 6.30 | 2 | + | + | + | + |

FIG. 11 (Continued)

| | | | | | | |
|---|---|---|---|---|---|---|
| / | 329.2007 | 5.31 | 1 | + | + | + | + |
| / | 329.2282 | 15.00 | 2 | + | + | + | + |
| / | 330.1635 | 19.95 | 1 | + | + | + | + |
| / | 330.2011 | 12.78 | 2 | + | + | + | + |
| / | 332.2266 | 14.24 | 1 | + | + | + | + |
| / | 332.2273 | 18.89 | 1 | + | + | + | + |
| / | 335.1611 | 21.76 | 3 | + | + | + | + |
| / | 337.1392 | 20.13 | 2 | + | + | - | - |
| / | 338.8360 | 21.02 | | + | + | - | - |
| / | 339.1935 | 10.87 | 2 | + | + | + | + |
| / | 339.6729 | 11.52 | 2 | + | + | + | + |
| / | 343.2051 | 12.27 | | + | + | + | + |
| / | 344.2632 | 20.16 | 1 | + | + | + | + |
| / | 345.1529 | 9.63 | 1 | + | + | + | + |
| / | 345.2333 | 5.31 | 1 | + | + | + | + |
| / | 347.2014 | 7.77 | 1 | + | + | + | + |
| / | 347.7072 | 11.46 | 2 | + | + | + | + |
| / | 350.1806 | 9.63 | 1 | + | + | + | + |
| / | 350.6348 | 14.08 | 2 | + | + | + | + |
| / | 353.4912 | 14.88 | 3 | + | + | + | + |
| / | 359.2392 | 10.08 | 1 | + | + | + | + |

FIG. 11 (Continued)

| | | | | | | | |
|---|---|---|---|---|---|---|---|
| / | 359.6404 | 14.08 | 2 | + | + | + | + |
| / | 365.8721 | 8.27 | | + | + | + | - |
| / | 366.2176 | 17.35 | 2 | + | + | + | + |
| / | 369.2061 | 13.59 | 3 | + | + | + | + |
| / | 369.7033 | 6.30 | 2 | + | + | + | + |
| / | 371.2385 | 10.98 | 1 | + | + | + | + |
| / | 371.7236 | 16.41 | 2 | + | + | + | + |
| / | 372.2159 | 10.36 | 2 | + | + | + | + |
| / | 372.6956 | 5.59 | 2 | + | + | + | + |
| / | 372.8516 | 14.88 | 3 | + | + | - | - |
| / | 373.2899 | 6.30 | 1 | + | + | + | + |
| / | 374.2389 | 18.89 | 1 | + | + | + | + |
| / | 374.7011 | 12.41 | 2 | + | + | + | + |
| / | 374.8536 | 14.46 | 3 | + | + | + | + |
| / | 375.2342 | 7.77 | 1 | + | + | + | + |
| / | 377.1926 | 13.59 | 1 | + | + | + | + |
| / | 377.1953 | 11.46 | 1 | + | + | + | + |
| / | 377.8407 | 14.88 | 3 | + | + | - | - |
| / | 378.6137 | 14.08 | 2 | + | + | + | + |
| / | 379.2181 | 24.94 | 2 | + | + | + | + |
| / | 379.7035 | 10.98 | 2 | + | + | + | + |

FIG. 11 (Continued)

| | | | | | | | |
|---|---|---|---|---|---|---|---|
| / | 379.8415 | 14.46 | 3 | + | + | + | + |
| / | 381.8550 | 13.59 | 3 | + | + | + | + |
| / | 382.5030 | 14.46 | 3 | + | + | + | + |
| / | 383.7419 | 15.00 | 2 | + | + | + | - |
| / | 384.2149 | 8.64 | 2 | + | + | + | - |
| / | 385.2063 | 8.27 | 2 | + | + | + | + |
| / | 385.2297 | 10.08 | 1 | + | + | + | + |
| / | 385.2661 | 9.40 | 1 | + | + | + | + |
| / | 385.5505 | 13.59 | 3 | + | + | - | - |
| 1 | 386.2108 | 10.36 | 2 | - | + | - | - |
| / | 386.8436 | 13.59 | 3 | + | + | + | + |
| / | 387.8462 | 19.63 | 3 | + | + | + | + |
| / | 388.2293 | 6.30 | | + | + | + | + |
| / | 388.2296 | 12.27 | | + | + | + | + |
| / | 389.2488 | 11.01 | 1 | + | + | + | + |
| / | 390.2222 | 10.60 | 2 | + | + | + | + |
| / | 390.8836 | 12.91 | 3 | + | + | - | - |
| / | 391.1910 | 5.31 | 1 | + | + | + | + |
| / | 391.2092 | 18.32 | 1 | + | + | + | + |
| / | 392.2315 | 13.05 | 2 | + | + | + | + |
| / | 392.9530 | 20.13 | 4 | + | + | - | - |

FIG. 11 (Continued)

| | | | | | | |
|---|---|---|---|---|---|---|
| / | 393.2091 | 9.40 | 2 | + | + | + | + |
| / | 393.2267 | 11.01 | 2 | + | + | + | - |
| / | 393.7321 | 23.66 | 2 | + | + | - | - |
| / | 395.6893 | 8.94 | 2 | + | + | + | + |
| / | 396.2707 | 14.62 | 1 | + | + | + | + |
| / | 396.6962 | 20.13 | 4 | + | + | + | - |
| / | 398.1658 | 6.30 | | + | + | - | + |
| / | 398.2194 | 10.08 | | + | + | + | - |
| / | 398.2272 | 15.00 | 3 | + | + | + | + |
| / | 398.2504 | 14.18 | 1 | + | + | + | + |
| / | 399.2711 | 17.34 | 1 | + | + | + | + |
| / | 400.2297 | 9.40 | 1 | + | + | + | + |
| / | 400.2298 | 12.78 | 2 | + | + | + | + |
| / | 402.2567 | 10.08 | 1 | + | + | + | + |
| / | 402.5164 | 22.63 | 3 | + | + | + | + |
| / | 403.2657 | 15.00 | 1 | + | + | + | + |
| / | 403.2657 | 16.04 | 1 | + | + | - | - |
| / | 404.2236 | 9.40 | 1 | + | + | + | + |
| / | 404.4604 | 19.63 | 4 | + | + | + | + |
| / | 405.2085 | 10.36 | | + | + | - | - |
| / | 405.2186 | 9.63 | 2 | + | + | + | + |

FIG. 11 (Continued)

| | | | | | | | |
|---|---|---|---|---|---|---|---|
| / | 406.2352 | 13.25 | 2 | + | + | + | - |
| / | 406.2358 | 12.21 | 2 | + | + | + | + |
| / | 407.2195 | 15.76 | 2 | + | + | + | + |
| / | 407.9573 | 19.63 | 4 | + | + | + | + |
| / | 410.8747 | 15.00 | 3 | + | + | + | + |
| / | 411.2322 | 10.98 | 1 | + | + | + | + |
| / | 411.6992 | 19.63 | 4 | + | + | + | + |
| / | 412.2536 | 16.04 | 2 | + | + | + | + |
| / | 412.2540 | 15.75 | 2 | + | + | + | + |
| / | 413.2410 | 14.18 | 2 | + | + | + | + |
| / | 413.2866 | 21.76 | 1 | + | + | + | + |
| / | 414.2108 | 14.52 | 2 | + | + | - | - |
| / | 414.2413 | 14.88 | 3 | + | + | + | + |
| / | 414.2457 | 12.27 | 1 | + | + | + | + |
| / | 415.2447 | 22.63 | 1 | + | + | + | + |
| / | 415.8626 | 15.00 | 3 | + | + | + | + |
| / | 418.2195 | 17.95 | 1 | + | + | + | + |
| / | 418.7339 | 10.36 | 2 | + | + | + | + |
| / | 420.1979 | 13.01 | 1 | + | + | + | + |
| / | 421.2412 | 12.45 | 2 | + | + | + | + |
| / | 421.2432 | 20.13 | 2 | + | + | + | + |

FIG. 11 (Continued)

| | | | | | | | |
|---|---|---|---|---|---|---|---|
| / | 421.2612 | 15.00 | 2 | + | + | + | + |
| / | 421.7331 | 9.63 | 2 | + | + | + | + |
| / | 422.2127 | 5.31 | 1 | + | + | + | + |
| / | 426.7299 | 8.94 | 2 | + | + | + | + |
| / | 427.7383 | 11.01 | 2 | + | + | - | - |
| / | 427.7393 | 10.98 | 2 | + | + | - | - |
| / | 429.2457 | 22.30 | 1 | + | + | + | + |
| / | 429.2826 | 21.01 | 1 | + | + | + | + |
| / | 430.2411 | 12.78 | 1 | + | + | + | + |
| / | 430.2775 | 20.63 | 1 | + | + | + | + |
| / | 431.2253 | 13.59 | 2 | + | + | + | + |
| / | 431.2478 | 6.30 | 1 | + | + | + | + |
| / | 431.5276 | 21.95 | 3 | + | + | + | + |
| / | 432.2315 | 8.27 | 1 | + | + | + | + |
| / | 434.2619 | 17.34 | 2 | + | + | + | + |
| / | 434.7471 | 10.81 | 2 | + | + | + | + |
| / | 437.7673 | 31.77 | 2 | + | + | + | + |
| / | 441.2521 | 20.49 | 2 | + | + | + | + |
| / | 441.7730 | 18.54 | 2 | + | + | + | + |
| / | 442.7441 | 12.27 | 2 | + | + | + | + |
| / | 443.2353 | 6.30 | 1 | + | + | + | + |

FIG. 11 (Continued)

| | | | | | | | |
|---|---|---|---|---|---|---|---|
| / | 444.2303 | 10.08 | 2 | + | + | + | + |
| / | 444.2936 | 20.49 | 1 | + | + | + | + |
| / | 445.2527 | 7.80 | 1 | + | + | + | + |
| / | 446.2717 | 8.27 | 1 | + | + | + | + |
| / | 446.2722 | 16.69 | 1 | + | + | + | + |
| / | 446.5774 | 19.63 | 3 | + | + | - | - |
| / | 446.7472 | 11.52 | 2 | + | + | + | + |
| / | 446.7659 | 14.62 | 2 | + | + | + | + |
| / | 447.2085 | 13.59 | 1 | + | + | + | + |
| / | 447.2105 | 6.30 | 1 | + | + | + | + |
| / | 447.2542 | 14.60 | 1 | + | + | + | + |
| / | 448.2467 | 10.36 | 2 | + | + | + | + |
| / | 449.7704 | 16.48 | 2 | + | + | + | + |
| / | 451.2280 | 22.27 | 1 | + | + | + | + |
| / | 453.2203 | 12.27 | | + | + | + | + |
| / | 454.7644 | 13.80 | 2 | + | + | + | + |
| / | 455.2042 | 19.61 | 1 | + | + | + | + |
| 2 | 455.2539 | 10.90 | 2 | - | + | - | - |
| / | 456.2434 | 8.94 | 2 | + | + | + | + |
| / | 456.2456 | 13.15 | 2 | + | + | + | + |
| / | 456.2925 | 23.26 | 1 | + | + | + | + |

FIG. 11 (Continued)

|   |   |   |   |   |   |   |   |
|---|---|---|---|---|---|---|---|
| / | 457.2030 | 14.88 | 2 | + | + | + | + |
| / | 457.7509 | 12.27 | 2 | + | + | + | + |
| / | 458.2476 | 12.10 | 2 | + | + | + | + |
| / | 459.1892 | 12.27 | 2 | + | + | + | + |
| / | 459.2278 | 19.63 | 3 | + | + | + | + |
| / | 459.2678 | 10.98 | 1 | + | + | + | + |
| / | 459.2685 | 5.59 | 1 | + | + | + | + |
| / | 459.2935 | 21.96 | 1 | + | + | + | + |
| / | 460.4769 | 18.89 | 4 | + | + | - | - |
| / | 461.2554 | 11.46 | 2 | + | + | - | - |
| / | 462.2302 | 6.30 | 1 | + | + | + | + |
| / | 462.2472 | 19.19 | 1 | + | + | + | + |
| / | 464.2263 | 13.90 | 1 | + | + | + | + |
| / | 464.4752 | 18.89 | 4 | + | + | - | - |
| / | 464.7522 | 12.26 | 2 | + | + | + | + |
| / | 465.2464 | 14.88 | 1 | + | + | + | + |
| / | 467.7294 | 17.95 | 2 | + | + | + | + |
| / | 467.7517 | 11.01 | 2 | + | + | + | + |
| / | 468.2369 | 11.52 | 1 | + | + | + | + |
| / | 469.2535 | 10.08 | 2 | + | + | - | - |
| / | 469.2711 | 13.03 | 2 | + | + | - | - |

FIG. 11 (Continued)

| | | | | | | | |
|---|---|---|---|---|---|---|---|
| / | 471.7388 | 12.84 | 2 | + | + | + | + |
| / | 472.2880 | 13.31 | 1 | + | + | + | + |
| / | 472.2893 | 21.02 | 1 | + | + | + | + |
| / | 472.2992 | 9.40 | 1 | + | + | + | + |
| / | 472.5596 | 18.89 | 3 | + | + | + | + |
| / | 473.2079 | 18.21 | 2 | + | + | + | + |
| / | 473.2346 | 5.59 | | + | + | + | - |
| / | 474.2428 | 11.52 | 1 | + | + | + | + |
| / | 474.2429 | 10.08 | 1 | + | + | + | + |
| / | 474.2679 | 12.27 | 2 | + | + | + | + |
| / | 474.2682 | 12.27 | 1 | + | + | + | + |
| / | 474.2799 | 5.31 | 1 | + | + | + | + |
| / | 475.7502 | 10.57 | 2 | + | + | + | + |
| / | 476.2273 | 18.89 | 1 | + | + | + | + |
| / | 476.2476 | 12.35 | 2 | + | + | + | + |
| / | 478.2575 | 16.50 | 2 | + | + | - | + |
| / | 478.7565 | 13.59 | 2 | + | + | + | + |
| / | 479.2622 | 17.50 | 1 | + | + | + | + |
| / | 479.7979 | 12.78 | 2 | + | + | + | + |
| / | 480.2565 | 21.76 | 1 | + | + | + | + |
| / | 480.7737 | 22.63 | 2 | + | + | - | - |

FIG. 11 (Continued)

| | | | | | | | |
|---|---|---|---|---|---|---|---|
| / | 484.2314 | 6.30 | 2 | + | + | + | + |
| / | 486.3042 | 14.60 | 1 | + | + | + | + |
| / | 486.3052 | 14.62 | 1 | + | + | + | + |
| / | 488.7716 | 21.02 | 2 | + | + | - | - |
| / | 490.2600 | 5.59 | | + | + | + | + |
| / | 491.7648 | 22.63 | 2 | + | + | - | - |
| / | 492.5855 | 12.10 | 3 | + | + | - | - |
| / | 493.2424 | 19.19 | 1 | + | + | + | + |
| / | 498.7538 | 9.63 | 2 | + | + | + | + |
| / | 499.2625 | 7.80 | 1 | + | + | + | + |
| / | 499.2998 | 14.24 | 1 | + | + | - | - |
| / | 499.7645 | 21.01 | 2 | + | + | + | + |
| / | 501.2429 | 6.30 | 1 | + | + | + | + |
| / | 501.7630 | 24.02 | 2 | + | + | + | + |
| / | 504.7541 | 12.50 | 2 | + | + | + | - |
| / | 507.7421 | 19.80 | 2 | + | + | + | + |
| / | 508.2906 | 15.50 | 1 | + | + | + | + |
| / | 509.7630 | 19.19 | 2 | + | + | + | + |
| / | 510.2391 | 16.77 | 2 | + | + | + | + |
| / | 510.9530 | 20.13 | 3 | + | + | - | - |
| / | 511.2845 | 23.66 | 2 | + | + | + | + |

FIG. 11 (Continued)

|   |          |       |   |   |   |   |   |
|---|----------|-------|---|---|---|---|---|
| / | 511.7312 | 19.81 | 2 | + | + | + | + |
| / | 512.2539 | 16.68 | 2 | + | + | + | + |
| / | 512.5736 | 19.63 | 3 | + | + | + | + |
| / | 512.7552 | 24.02 | 2 | + | + | + | + |
| / | 513.7482 | 20.49 | 2 | + | + | + | + |
| / | 514.2510 | 13.59 | 2 | + | + | - | + |
| / | 515.2510 | 19.50 | 2 | + | + | + | + |
| / | 515.3429 | 10.06 | 1 | + | + | + | + |
| / | 517.6038 | 16.04 | 3 | + | + | - | + |
| / | 518.2789 | 20.15 | 3 | + | + | - | - |
| / | 518.7344 | 19.81 | 2 | + | + | + | + |
| / | 520.7371 | 24.02 | 2 | + | + | + | + |
| / | 520.9586 | 20.16 | 3 | - | + | + | - |
| / | 523.6025 | 20.13 | 3 | + | + | - | - |
| / | 524.7756 | 11.14 | 2 | - | + | + | - |
| / | 524.8132 | 17.94 | 2 | + | + | + | - |
| / | 526.2750 | 5.31  | 1 | + | + | + | + |
| / | 526.7177 | 19.81 | 2 | + | + | + | + |
| / | 527.2957 | 12.10 | 1 | + | + | + | + |
| / | 528.5910 | 20.13 | 3 | + | + | - | - |
| / | 528.9272 | 20.10 | 3 | + | + | + | - |

FIG. 11 (Continued)

| / | 529.6020 | 19.40 | 3 | + | + | + | + |
|---|---|---|---|---|---|---|---|
| / | 530.7887 | 18.89 | 2 | + | + | + | + |
| / | 530.9570 | 19.63 | 3 | + | + | + | + |
| / | 531.2907 | 12.27 | 1 | + | + | + | + |
| / | 531.7855 | 12.78 | 2 | + | + | + | + |
| / | 531.7965 | 13.21 | 2 | + | + | - | - |
| / | 532.2520 | 18.39 | 2 | + | + | - | - |
| / | 534.1999 | 19.81 | 2 | + | + | + | + |
| / | 534.2432 | 6.30 | 1 | + | + | + | + |
| / | 535.2696 | 14.08 | 1 | + | + | + | + |
| / | 535.6320 | 21.32 | 3 | + | + | - | - |
| / | 535.8036 | 17.75 | 2 | + | + | + | + |
| / | 536.7798 | 12.35 | 2 | + | + | + | - |
| / | 538.2274 | 12.65 | 2 | + | + | + | + |
| / | 538.2836 | 19.63 | 3 | + | + | + | + |
| / | 538.7866 | 17.27 | 2 | + | + | + | + |
| / | 539.7781 | 28.50 | 2 | + | + | + | + |
| / | 539.7992 | 14.82 | 2 | + | + | - | - |
| / | 542.7990 | 14.46 | 2 | + | + | + | + |
| / | 543.3277 | 19.19 | 1 | + | + | - | - |
| / | 543.6046 | 19.63 | 3 | + | + | + | + |

FIG. 11 (Continued)

|   |         |       |   |   |   |   |   |
|---|---------|-------|---|---|---|---|---|
| / | 544.2973 | 12.40 | 1 | + | + | + | + |
| / | 544.3862 | 26.81 | 1 | + | + | + | + |
| / | 544.7864 | 16.68 | 2 | + | + | + | + |
| / | 544.7866 | 17.43 | 2 | + | + | + | + |
| / | 545.3081 | 14.46 | 2 | + | + | + | + |
| / | 546.7834 | 16.04 | 2 | + | + | + | + |
| / | 547.7753 | 27.08 | 2 | + | + | + | + |
| / | 548.9296 | 19.63 | 3 | + | + | + | + |
| / | 550.7959 | 14.24 | 2 | + | + | + | + |
| / | 552.6142 | 12.58 | 3 | + | + | + | + |
| 3 | 552.7825 | 15.98 | 2 | - | + | - | - |
| / | 553.3052 | 13.59 | 2 | + | + | + | + |
| / | 553.7987 | 13.56 | 2 | + | + | + | + |
| / | 555.7896 | 14.46 | 2 | + | + | - | - |
| / | 556.3212 | 12.55 | 1 | + | + | + | + |
| / | 556.6228 | 13.31 | 3 | + | + | - | - |
| / | 556.7927 | 17.20 | 2 | + | + | + | + |
| / | 558.3128 | 5.59  |   | + | + | + | + |
| / | 558.7653 | 27.09 | 2 | + | + | + | + |
| / | 560.3174 | 13.31 | 1 | + | + | + | + |
| / | 561.3171 | 24.91 | 1 | + | + | + | + |

FIG. 11 (Continued)

| / | 562.2794 | 12.78 | 1 | + | + | + | + |
|---|----------|-------|---|---|---|---|---|
| / | 563.8012 | 17.94 | 2 | + | + | + | + |
| / | 564.2834 | 15.75 | 1 | + | + | + | + |
| / | 564.2942 | 13.60 | 2 | + | + | + | + |
| / | 565.3103 | 19.19 | 1 | + | + | - | - |
| / | 568.2868 | 6.30  | 1 | + | + | + | + |
| / | 569.6130 | 14.46 | 3 | + | + | + | + |
| / | 569.7932 | 10.06 | 2 | + | + | + | + |
| / | 570.3125 | 12.10 | 1 | + | + | + | + |
| / | 571.2687 | 13.00 | 1 | - | + | + | + |
| / | 571.2819 | 12.27 | 1 | + | + | + | + |
| / | 571.3244 | 19.81 | 1 | + | + | + | - |
| / | 572.2779 | 13.60 | 2 | + | + | + | + |
| / | 572.3803 | 25.69 | 1 | + | + | + | + |
| / | 573.2504 | 14.46 | 2 | + | + | + | + |
| / | 573.2644 | 5.31  | 1 | + | + | + | + |
| / | 573.3398 | 23.14 | 1 | + | + | + | + |
| / | 574.2337 | 27.09 | 2 | + | + | + | + |
| / | 575.3018 | 14.46 | 2 | + | + | + | + |
| / | 577.8215 | 13.75 | 2 | + | + | - | - |
| / | 578.2752 | 5.31  | 1 | + | + | + | + |

FIG. 11 (Continued)

| | | | | | | | |
|---|---|---|---|---|---|---|---|
| / | 578.3000 | 12.27 | 2 | + | + | + | + |
| / | 578.3056 | 12.53 | 1 | + | + | + | + |
| / | 579.6278 | 15.28 | 3 | + | + | - | - |
| / | 579.7647 | 13.59 | 2 | + | + | + | + |
| / | 581.2635 | 19.63 | 2 | + | + | + | + |
| / | 581.3193 | 11.52 | 1 | + | + | + | + |
| / | 581.8293 | 17.50 | 2 | + | + | + | + |
| / | 583.6149 | 14.46 | 3 | + | + | - | + |
| / | 583.8135 | 12.10 | 2 | + | + | + | + |
| / | 584.3129 | 6.30 | | + | + | + | + |
| / | 585.3025 | 15.28 | 1 | + | + | - | - |
| / | 586.3359 | 16.42 | 1 | + | + | + | + |
| / | 587.1737 | 14.08 | 1 | + | + | + | + |
| / | 587.3193 | 16.26 | 1 | + | + | + | - |
| / | 588.8368 | 16.04 | 2 | + | + | + | + |
| / | 589.2899 | 12.40 | 3 | + | + | - | + |
| / | 589.3338 | 15.44 | 1 | + | + | + | + |
| / | 591.8236 | 21.95 | 2 | + | + | + | - |
| / | 591.8301 | 14.95 | 2 | + | + | - | - |
| / | 594.2725 | 14.46 | 2 | + | + | + | + |
| / | 595.6501 | 20.13 | 3 | + | + | - | - |

FIG. 11 (Continued)

| | | | | | | | |
|---|---|---|---|---|---|---|---|
| / | 596.3298 | 12.10 | 1 | + | + | + | + |
| / | 596.8323 | 14.97 | 2 | + | + | + | + |
| / | 598.3134 | 20.60 | 2 | + | + | - | - |
| / | 599.3923 | 22.27 | 1 | + | + | + | + |
| / | 599.8293 | 14.00 | 2 | + | + | - | - |
| / | 600.2304 | 12.78 | | + | + | + | + |
| / | 600.3867 | 20.13 | 1 | + | + | + | + |
| / | 600.9833 | 18.89 | 3 | + | + | - | - |
| / | 601.3122 | 18.39 | 2 | + | + | + | + |
| / | 602.2936 | 14.24 | 1 | + | + | + | + |
| / | 602.3176 | 17.10 | 3 | + | + | - | + |
| / | 602.3390 | 8.27 | 1 | + | + | + | + |
| / | 603.2689 | 22.63 | 2 | + | + | + | + |
| / | 604.2905 | 12.35 | 1 | + | + | + | + |
| / | 604.3075 | 9.40 | 1 | + | + | + | + |
| / | 607.2546 | 15.50 | 1 | + | + | + | + |
| / | 607.2905 | 19.63 | 1 | + | + | + | + |
| / | 607.8255 | 14.80 | 2 | + | + | + | + |
| / | 608.3549 | 16.74 | 1 | + | + | + | + |
| / | 609.8244 | 17.75 | 2 | + | + | + | + |
| / | 614.6549 | 16.68 | 3 | + | + | - | - |

FIG. 11 (Continued)

| | | | | | | | |
|---|---|---|---|---|---|---|---|
| / | 618.3262 | 13.31 | 2 | + | + | - | - |
| / | 618.3392 | 12.35 | 1 | + | + | + | + |
| / | 621.3747 | 21.95 | 1 | + | + | + | + |
| / | 621.9774 | 17.10 | 3 | + | + | + | - |
| / | 623.8404 | 23.30 | 2 | + | + | - | - |
| / | 624.3507 | 15.75 | 1 | + | + | + | + |
| / | 628.3564 | 12.10 | 2 | + | + | + | + |
| / | 629.8132 | 12.78 | 2 | + | + | + | + |
| / | 635.3197 | 20.13 | 1 | + | + | - | - |
| / | 641.3310 | 23.36 | 2 | + | + | + | + |
| / | 643.3687 | 16.42 | 1 | + | + | + | + |
| / | 644.3510 | 10.06 | 1 | + | + | + | + |
| / | 644.8290 | 16.75 | 2 | + | + | + | - |
| / | 646.7862 | 21.95 | 2 | + | + | + | + |
| / | 647.3307 | 17.75 | 1 | + | + | + | + |
| / | 648.3511 | 20.10 | 2 | + | + | + | + |
| / | 648.8497 | 23.36 | 2 | + | + | + | + |
| / | 649.3000 | 19.82 | 1 | + | + | + | + |
| / | 649.3232 | 22.63 | 2 | + | + | + | + |
| / | 649.3496 | 18.89 | 3 | + | + | - | - |
| / | 654.3328 | 17.94 | 2 | + | + | + | + |

FIG. 11 (Continued)

| | | | | | | | |
|---|---|---|---|---|---|---|---|
| / | 654.3494 | 16.74 | 2 | + | + | - | - |
| / | 655.3567 | 15.28 | 1 | + | + | - | + |
| / | 655.3930 | 13.03 | 1 | + | + | + | + |
| / | 655.8360 | 14.50 | 2 | + | + | + | - |
| / | 656.4151 | 23.66 | 1 | + | + | - | - |
| / | 656.8466 | 21.95 | 2 | + | + | + | + |
| / | 660.3497 | 15.00 | 2 | + | + | + | + |
| / | 661.3627 | 20.80 | 2 | + | + | - | - |
| / | 662.3516 | 17.34 | 2 | + | + | + | + |
| / | 664.8443 | 20.70 | 2 | + | + | + | + |
| / | 666.8469 | 13.20 | 2 | + | + | + | + |
| / | 669.3605 | 19.63 | 2 | + | + | - | - |
| / | 670.3497 | 15.50 | 2 | + | + | + | + |
| / | 670.4318 | 23.36 | 1 | + | + | + | + |
| / | 672.3542 | 18.90 | 2 | + | + | + | + |
| / | 672.8430 | 20.00 | 2 | + | + | + | + |
| / | 676.8740 | 26.90 | 2 | + | + | - | - |
| / | 677.3781 | 10.98 | 1 | + | + | + | + |
| / | 683.8020 | 20.49 | 2 | + | + | + | + |
| / | 688.4038 | 20.13 | 1 | + | + | + | + |
| / | 690.3999 | 25.69 | 1 | - | + | + | - |

FIG. 11 (Continued)

|   |          |       |   |   |   |   |   |
|---|----------|-------|---|---|---|---|---|
| / | 690.8569 | 14.62 | 2 | + | + | - | - |
| / | 694.4061 | 11.52 | 1 | + | + | + | + |
| / | 696.8466 | 13.03 | 2 | + | + | + | - |
| / | 698.3878 | 19.19 | 1 | + | + | - | - |
| / | 703.3402 | 14.46 | 2 | + | + | + | + |
| / | 705.8646 | 21.52 | 2 | + | + | + | - |
| / | 708.3562 | 18.89 | 2 | + | + | + | + |
| / | 708.6879 | 14.08 | 3 | + | + | + | + |
| / | 710.8729 | 15.35 | 2 | + | + | + | + |
| / | 713.0401 | 19.05 | 3 | + | + | + | - |
| 4 | 716.4201 | 27.31 | 1 | - | + | - | - |
| / | 718.2710 | 14.08 | 1 | + | + | + | + |
| / | 718.7115 | 18.11 | 3 | + | + | + | - |
| / | 723.3107 | 13.49 | 1 | + | + | + | + |
| / | 723.7094 | 17.26 | 3 | + | + | + | - |
| / | 724.0438 | 17.34 | 3 | + | + | + | - |
| / | 724.3671 | 13.88 | 2 | + | + | - | + |
| / | 726.3114 | 20.13 | 2 | + | + | + | + |
| / | 726.3605 | 11.86 | 1 | + | + | + | + |
| / | 728.4091 | 22.27 | 2 | + | + | - | - |
| / | 730.3692 | 16.42 | 2 | + | + | + | + |

FIG. 11 (Continued)

| | | | | | | | |
|---|---|---|---|---|---|---|---|
| / | 731.8613 | 12.90 | 2 | + | + | - | + |
| / | 732.3417 | 17.04 | 1 | + | + | + | + |
| / | 733.3679 | 16.20 | 2 | + | + | - | - |
| / | 737.6915 | 18.80 | 3 | + | + | - | - |
| / | 745.3828 | 5.59 | | + | + | + | + |
| / | 745.8657 | 15.95 | 2 | + | + | - | + |
| / | 745.8669 | 15.33 | 2 | - | + | + | - |
| / | 746.8769 | 13.70 | 2 | + | + | - | - |
| / | 748.3914 | 12.40 | 1 | + | + | + | + |
| / | 749.0318 | 14.89 | 3 | + | + | + | + |
| / | 753.3849 | 21.52 | 2 | + | + | - | - |
| / | 753.8639 | 14.89 | 2 | + | + | + | + |
| / | 755.7079 | 15.33 | 3 | + | + | + | + |
| / | 757.4285 | 24.97 | 1 | + | + | + | - |
| / | 760.8886 | 16.89 | 2 | + | + | - | - |
| / | 761.0394 | 14.46 | 3 | + | + | + | + |
| / | 761.0683 | 20.49 | 3 | + | + | - | - |
| / | 762.3766 | 22.94 | 3 | - | + | - | + |
| / | 762.8742 | 13.03 | 2 | + | + | - | + |
| / | 763.8432 | 13.80 | 2 | + | + | - | - |
| / | 765.9196 | 20.10 | 2 | + | + | + | - |

FIG. 11 (Continued)

| | | | | | | | |
|---|---|---|---|---|---|---|---|
| / | 765.9238 | 20.13 | 2 | + | + | - | - |
| / | 766.7067 | 13.88 | 3 | + | + | + | + |
| / | 767.4245 | 8.27 | 1 | + | + | + | - |
| / | 767.7089 | 14.89 | 3 | + | + | + | - |
| / | 771.3333 | 10.39 | 1 | + | + | + | + |
| / | 773.3523 | 12.10 | | + | + | + | + |
| / | 775.9012 | 16.04 | 2 | + | + | - | + |
| / | 776.9109 | 20.13 | 2 | + | + | - | - |
| / | 778.3712 | 14.88 | 2 | + | + | + | + |
| / | 780.7086 | 11.86 | 3 | + | + | - | - |
| / | 780.9306 | 20.10 | 2 | - | + | + | + |
| / | 781.9127 | 22.43 | 2 | + | + | + | + |
| / | 781.9374 | 21.52 | 2 | + | + | + | + |
| / | 783.4554 | 13.03 | 1 | + | + | + | + |
| / | 784.8969 | 20.13 | 2 | + | + | + | + |
| / | 785.4468 | 10.98 | 1 | + | + | + | - |
| / | 785.8968 | 19.81 | 2 | + | + | + | + |
| / | 786.4556 | 23.66 | 1 | + | + | - | - |
| / | 790.9093 | 15.95 | 2 | - | + | + | - |
| / | 792.8801 | 18.34 | 2 | + | + | + | + |
| / | 793.8986 | 19.40 | 2 | + | + | + | + |

FIG. 11 (Continued)

| | | | | | | | |
|---|---|---|---|---|---|---|---|
| / | 795.9306 | 19.61 | 2 | + | + | + | + |
| / | 798.9020 | 16.04 | 2 | + | + | - | + |
| / | 800.3909 | 11.86 | 2 | + | + | + | - |
| / | 802.9475 | 21.40 | 2 | + | + | - | - |
| / | 804.3942 | 18.11 | 2 | + | + | - | + |
| / | 804.8810 | 13.59 | 2 | + | + | + | + |
| / | 811.4610 | 12.30 | 1 | + | + | + | + |
| / | 811.4614 | 13.13 | 1 | + | + | + | - |
| / | 811.4615 | 13.20 | 1 | + | + | + | - |
| / | 811.4623 | 12.27 | 1 | + | + | + | + |
| / | 811.4634 | 12.10 | 1 | + | + | + | + |
| / | 811.7179 | 18.34 | 3 | + | + | + | + |
| / | 813.4302 | 15.75 | 1 | + | + | + | + |
| / | 816.4244 | 16.24 | 2 | + | + | + | + |
| / | 821.3904 | 21.20 | 1 | + | + | + | + |
| / | 821.4173 | 20.49 | 2 | + | + | - | - |
| / | 823.5000 | 15.75 | 1 | + | + | + | - |
| / | 824.4354 | 19.63 | 2 | + | + | + | + |
| / | 825.9096 | 16.49 | 2 | + | + | - | - |
| / | 829.4146 | 19.19 | 2 | + | + | - | - |
| / | 834.7436 | 17.43 | 3 | + | + | + | + |

FIG. 11 (Continued)

| | | | | | | | |
|---|---|---|---|---|---|---|---|
| / | 841.4766 | 20.13 | 1 | + | + | + | + |
| / | 842.9218 | 18.95 | 2 | - | + | + | - |
| / | 844.4641 | 23.36 | 1 | + | + | + | - |
| / | 845.4240 | 22.27 | 3 | + | + | + | + |
| / | 845.9125 | 15.33 | 2 | + | + | + | + |
| / | 849.7429 | 26.80 | 3 | - | + | - | + |
| / | 850.4249 | 21.02 | 3 | + | + | + | + |
| / | 852.4311 | 17.04 | 1 | + | + | + | + |
| / | 854.4121 | 14.46 | 2 | + | + | + | + |
| / | 868.4834 | 10.62 | 1 | + | + | + | + |
| / | 868.9328 | 14.88 | 2 | + | + | - | - |
| / | 874.5250 | 31.78 | 1 | + | + | + | + |
| / | 874.7801 | 17.92 | 3 | + | + | + | + |
| / | 874.9170 | 14.46 | 2 | + | + | - | + |
| / | 883.4320 | 12.40 | 2 | + | + | - | + |
| / | 892.5215 | 14.62 | 1 | + | + | + | + |
| / | 892.9678 | 20.00 | 2 | + | + | - | - |
| / | 898.5327 | 16.42 | 1 | + | + | + | + |
| / | 900.9699 | 18.89 | 2 | + | + | - | - |
| / | 921.4785 | 16.68 | 2 | + | + | - | - |
| / | 926.5504 | 23.66 | 1 | + | + | + | + |

FIG. 11 (Continued)

| / | 928.4948 | 12.27 | 1 | + | + | + | + |
|---|---|---|---|---|---|---|---|
| / | 934.4512 | 17.75 | 1 | + | + | + | + |
| / | 937.5318 | 13.03 | 1 | + | + | - | - |
| / | 960.5383 | 22.63 | 1 | + | + | - | - |
| / | 976.5327 | 21.02 | 1 | + | + | - | - |
| / | 1008.4980 | 12.55 | 1 | + | + | + | - |
| / | 1014.4776 | 19.81 | 1 | + | + | + | + |
| / | 1018.5114 | 19.19 | 1 | + | + | + | + |
| / | 1021.5555 | 23.66 |   | + | + | + | + |
| / | 1027.4908 | 13.59 | 1 | + | + | - | + |
| / | 1029.4871 | 19.50 | 1 | + | + | + | + |
| / | 1078.5911 | 14.88 | 1 | + | + | - | - |
| / | 1088.5613 | 17.34 | 1 | + | + | + | + |
| / | 1092.5548 | 16.04 | 1 | + | + | + | + |
| / | 1094.5447 | 27.08 | 1 | + | + | + | + |
| / | 1105.5997 | 13.59 | 1 | + | + | + | + |
| / | 1149.5944 | 14.46 | 1 | + | + | + | + |
| / | 1192.6607 | 15.00 | 1 | + | + | + | + |

FIG. 11 (Continued)

Table 3

| Cattle marker No. | m/z | RT (min) | Charge | Donkey | Horse | Cattle | Pig |
|---|---|---|---|---|---|---|---|
| / | 189.1288 | 5.31 | 1 | + | + | + | + |
| / | 216.6198 | 8.26 | 2 | + | + | + | + |
| / | 219.1404 | 10.98 | 1 | + | + | + | + |
| / | 223.1141 | 8.27 | 1 | + | + | + | + |
| / | 224.1352 | 31.00 | 1 | + | + | + | + |
| / | 228.6384 | 5.31 | 2 | + | + | + | + |
| / | 229.6280 | 12.09 | 2 | + | + | + | + |
| / | 231.1762 | 10.44 | 1 | + | + | + | + |
| / | 231.1771 | 7.77 | | + | + | + | + |
| / | 233.1565 | 5.55 | 1 | + | + | + | + |
| / | 234.1024 | 22.27 | | + | + | + | + |
| / | 236.6544 | 9.34 | 2 | + | + | + | + |
| / | 237.6260 | 10.08 | 2 | + | + | + | + |
| / | 237.6447 | 5.31 | 2 | + | + | + | + |
| / | 242.1565 | 10.08 | 1 | + | + | + | + |
| / | 243.1408 | 15.75 | 1 | + | + | + | + |
| / | 245.1925 | 14.24 | 1 | + | + | + | + |
| / | 245.1925 | 15.38 | 1 | + | + | + | + |
| / | 249.6631 | 10.08 | 2 | + | + | + | + |

FIG. 12

| | | | | | | | |
|---|---|---|---|---|---|---|---|
| / | 250.1855 | 32.78 | 1 | + | + | + | + |
| / | 258.1766 | 10.10 | 2 | + | + | + | + |
| / | 260.1678 | 9.58 | 1 | + | + | + | + |
| / | 260.2043 | 6.27 | 1 | + | + | + | + |
| / | 265.1621 | 13.32 | 1 | + | + | + | + |
| / | 267.6266 | 6.27 | 2 | + | + | + | + |
| / | 270.2001 | 10.08 | 1 | + | + | + | + |
| / | 272.1795 | 9.40 | 1 | + | + | + | + |
| / | 272.6535 | 12.27 | 2 | + | + | + | + |
| / | 274.1954 | 10.08 | 1 | + | + | + | + |
| / | 276.1632 | 7.57 | 1 | + | + | + | + |
| / | 277.1257 | 9.74 | 1 | + | + | + | + |
| / | 278.6662 | 12.50 | 2 | + | + | + | + |
| / | 279.1418 | 17.53 | 1 | + | + | + | + |
| / | 279.1777 | 18.20 | 1 | + | + | + | + |
| / | 281.1213 | 10.08 | 1 | + | + | + | + |
| / | 281.1566 | 5.59 | 1 | + | + | + | + |
| / | 283.8095 | 12.27 | 2 | + | + | + | + |
| / | 288.2009 | 20.49 | | + | + | + | + |
| / | 288.2116 | 6.30 | | + | + | + | + |
| / | 290.1784 | 6.30 | | + | + | + | + |

FIG. 12 (Continued)

| | | | | | | | |
|---|---|---|---|---|---|---|---|
| / | 292.6630 | 12.27 | 2 | + | + | + | + |
| / | 295.1730 | 10.98 | 1 | + | + | + | + |
| / | 295.1740 | 10.08 | 1 | + | + | + | + |
| / | 297.6402 | 12.50 | 2 | + | + | + | + |
| / | 300.6175 | 12.78 | 2 | + | + | + | + |
| / | 301.1832 | 6.30 | 2 | + | + | + | + |
| / | 301.6758 | 8.27 | 2 | + | + | + | + |
| / | 301.6768 | 14.24 | 2 | + | + | + | + |
| / | 302.1801 | 10.08 | 1 | + | + | + | + |
| / | 302.2159 | 19.22 | 1 | + | + | + | + |
| / | 302.2166 | 18.21 | 1 | + | + | + | + |
| / | 303.6207 | 6.30 | 1 | + | + | + | + |
| / | 305.6956 | 11.52 | 2 | + | + | + | + |
| / | 306.1484 | 23.08 | 2 | + | + | + | + |
| / | 306.1739 | 6.30 | | + | + | + | + |
| / | 309.6738 | 12.35 | 2 | + | + | + | + |
| / | 312.8329 | 16.42 | 3 | + | + | + | + |
| / | 314.6831 | 12.07 | 2 | + | + | + | + |
| / | 314.7013 | 11.46 | 2 | + | + | + | - |
| / | 316.2312 | 19.63 | 1 | + | + | + | + |
| / | 317.1910 | 6.30 | 3 | + | + | + | + |

FIG. 12 (Continued)

| | | | | | | | |
|---|---|---|---|---|---|---|---|
| / | 320.1733 | 14.88 | 1 | + | + | + | + |
| / | 320.1866 | 8.27 | 1 | + | + | + | - |
| / | 320.2031 | 12.78 | 3 | + | + | + | + |
| / | 321.1797 | 13.31 | 2 | + | + | + | - |
| / | 321.1817 | 5.59 | 1 | + | + | + | + |
| / | 322.6805 | 10.06 | 2 | + | + | + | + |
| / | 322.8205 | 12.27 | 3 | + | + | + | + |
| / | 323.1587 | 6.30 | | + | + | + | + |
| / | 323.4940 | 6.30 | | + | + | + | + |
| / | 324.1811 | 5.59 | 2 | + | + | + | + |
| / | 327.8098 | 12.27 | 3 | + | + | + | + |
| / | 329.1909 | 6.30 | 2 | + | + | + | + |
| / | 329.2007 | 5.31 | 1 | + | + | + | + |
| / | 329.2282 | 15.00 | 2 | + | + | + | + |
| / | 330.1635 | 19.95 | 1 | + | + | + | + |
| / | 330.2011 | 12.78 | 2 | + | + | + | + |
| / | 332.2266 | 14.24 | 1 | + | + | + | + |
| / | 332.2273 | 18.89 | 1 | + | + | + | + |
| / | 335.1611 | 21.76 | 3 | + | + | + | + |
| / | 339.1935 | 10.87 | 2 | + | + | + | + |
| / | 339.6729 | 11.52 | 2 | + | + | + | + |

FIG. 12 (Continued)

| | | | | | | | |
|---|---|---|---|---|---|---|---|
| / | 343.2051 | 12.27 |   | + | + | + | + |
| / | 344.2632 | 20.16 | 1 | + | + | + | + |
| / | 345.1529 | 9.63 | 1 | + | + | + | + |
| / | 345.2333 | 5.31 | 1 | + | + | + | + |
| / | 347.2014 | 7.77 | 1 | + | + | + | + |
| / | 347.7072 | 11.46 | 2 | + | + | + | + |
| / | 350.1806 | 9.63 | 1 | + | + | + | + |
| / | 350.6348 | 14.08 | 2 | + | + | + | + |
| / | 353.4912 | 14.88 | 3 | + | + | + | + |
| / | 359.2392 | 10.08 | 1 | + | + | + | + |
| / | 359.6404 | 14.08 | 2 | + | + | + | + |
| / | 365.8721 | 8.27 |   | + | + | + | - |
| / | 366.2176 | 17.35 | 2 | + | + | + | + |
| / | 369.2061 | 13.59 | 3 | + | + | + | + |
| / | 369.7033 | 6.30 | 2 | + | + | + | + |
| / | 371.2385 | 10.98 | 1 | + | + | + | + |
| / | 371.7236 | 16.41 | 2 | + | + | + | + |
| / | 372.2159 | 10.36 | 2 | + | + | + | + |
| / | 372.6956 | 5.59 | 2 | + | + | + | + |
| / | 373.2899 | 6.30 | 1 | + | + | + | + |
| / | 374.2389 | 18.89 | 1 | + | + | + | + |

FIG. 12 (Continued)

| | | | | | | | |
|---|---|---|---|---|---|---|---|
| / | 374.7011 | 12.41 | 2 | + | + | + | + |
| / | 374.8536 | 14.46 | 3 | + | + | + | + |
| / | 375.2342 | 7.77 | 1 | + | + | + | + |
| / | 377.1926 | 13.59 | 1 | + | + | + | + |
| / | 377.1953 | 11.46 | 1 | + | + | + | + |
| / | 378.6137 | 14.08 | 2 | + | + | + | + |
| / | 379.2181 | 24.94 | 2 | + | + | + | + |
| / | 379.7035 | 10.98 | 2 | + | + | + | + |
| / | 379.8415 | 14.46 | 3 | + | + | + | + |
| / | 381.8550 | 13.59 | 3 | + | + | + | + |
| / | 382.5030 | 14.46 | 3 | + | + | + | + |
| / | 383.7419 | 15.00 | 2 | + | + | + | - |
| / | 384.2149 | 8.64 | 2 | + | + | + | - |
| / | 385.2063 | 8.27 | 2 | + | + | + | + |
| / | 385.2297 | 10.08 | 1 | + | + | + | + |
| / | 385.2661 | 9.40 | 1 | + | + | + | + |
| / | 386.8436 | 13.59 | 3 | + | + | + | + |
| / | 387.8462 | 19.63 | 3 | + | + | + | + |
| / | 388.2293 | 6.30 | | + | + | + | + |
| / | 388.2296 | 12.27 | | + | + | + | + |
| / | 389.2488 | 11.01 | 1 | + | + | + | + |

FIG. 12 (Continued)

| | | | | | | | |
|---|---|---|---|---|---|---|---|
| / | 390.2222 | 10.60 | 2 | + | + | + | + |
| / | 391.1910 | 5.31 | 1 | + | + | + | + |
| / | 391.2092 | 18.32 | 1 | + | + | + | + |
| / | 392.2315 | 13.05 | 2 | + | + | + | + |
| / | 393.2091 | 9.40 | 2 | + | + | + | + |
| / | 393.2267 | 11.01 | 2 | + | + | + | - |
| / | 395.6893 | 8.94 | 2 | + | + | + | + |
| / | 396.2707 | 14.62 | 1 | + | + | + | + |
| / | 396.6962 | 20.13 | 4 | + | + | + | - |
| / | 398.2194 | 10.08 |   | + | + | + | - |
| / | 398.2272 | 15.00 | 3 | + | + | + | + |
| / | 398.2504 | 14.18 | 1 | + | + | + | + |
| / | 399.2711 | 17.34 | 1 | + | + | + | + |
| / | 400.2297 | 9.40 | 1 | + | + | + | + |
| / | 400.2298 | 12.78 | 2 | + | + | + | + |
| / | 402.2567 | 10.08 | 1 | + | + | + | + |
| / | 402.5164 | 22.63 | 3 | + | + | + | + |
| / | 403.2657 | 15.00 | 1 | + | + | + | + |
| / | 404.2236 | 9.40 | 1 | + | + | + | + |
| / | 404.4604 | 19.63 | 4 | + | + | + | + |
| / | 405.2186 | 9.63 | 2 | + | + | + | + |

FIG. 12 (Continued)

| | | | | | | | |
|---|---|---|---|---|---|---|---|
| / | 406.2352 | 13.25 | 2 | + | + | + | - |
| / | 406.2358 | 12.21 | 2 | + | + | + | + |
| / | 407.2195 | 15.76 | 2 | + | + | + | + |
| / | 407.9573 | 19.63 | 4 | + | + | + | + |
| / | 410.8747 | 15.00 | 3 | + | + | + | + |
| / | 411.2322 | 10.98 | 1 | + | + | + | + |
| / | 411.6992 | 19.63 | 4 | + | + | + | + |
| / | 412.2536 | 16.04 | 2 | + | + | + | + |
| / | 412.2540 | 15.75 | 2 | + | + | + | + |
| / | 413.2410 | 14.18 | 2 | + | + | + | + |
| / | 413.2866 | 21.76 | 1 | + | + | + | + |
| / | 414.2413 | 14.88 | 3 | + | + | + | + |
| / | 414.2457 | 12.27 | 1 | + | + | + | + |
| / | 415.2447 | 22.63 | 1 | + | + | + | + |
| / | 415.8626 | 15.00 | 3 | + | + | + | + |
| / | 418.2195 | 17.95 | 1 | + | + | + | + |
| / | 418.7339 | 10.36 | 2 | + | + | + | + |
| / | 420.1979 | 13.01 | 1 | + | + | + | + |
| / | 421.2412 | 12.45 | 2 | + | + | + | + |
| / | 421.2432 | 20.13 | 2 | + | + | + | + |
| / | 421.2612 | 15.00 | 2 | + | + | + | + |

FIG. 12 (Continued)

| | | | | | | | |
|---|---|---|---|---|---|---|---|
| / | 421.7331 | 9.63 | 2 | + | + | + | + |
| / | 422.2127 | 5.31 | 1 | + | + | + | + |
| / | 426.7299 | 8.94 | 2 | + | + | + | + |
| / | 429.2457 | 22.30 | 1 | + | + | + | + |
| / | 429.2826 | 21.01 | 1 | + | + | + | + |
| / | 430.2411 | 12.78 | 1 | + | + | + | + |
| / | 430.2775 | 20.63 | 1 | + | + | + | + |
| / | 431.2253 | 13.59 | 2 | + | + | + | + |
| / | 431.2478 | 6.30 | 1 | + | + | + | + |
| / | 431.5276 | 21.95 | 3 | + | + | + | + |
| / | 432.2315 | 8.27 | 1 | + | + | + | + |
| / | 434.2619 | 17.34 | 2 | + | + | + | + |
| / | 434.7471 | 10.81 | 2 | + | + | + | + |
| / | 437.7673 | 31.77 | 2 | + | + | + | + |
| / | 441.2521 | 20.49 | 2 | + | + | + | + |
| / | 441.7730 | 18.54 | 2 | + | + | + | + |
| / | 442.7441 | 12.27 | 2 | + | + | + | + |
| / | 443.2353 | 6.30 | 1 | + | + | + | + |
| / | 444.2303 | 10.08 | 2 | + | + | + | + |
| / | 444.2936 | 20.49 | 1 | + | + | + | + |
| / | 445.2527 | 7.80 | 1 | + | + | + | + |

FIG. 12 (Continued)

| | | | | | | | |
|---|---|---|---|---|---|---|---|
| / | 446.2717 | 8.27 | 1 | + | + | + | + |
| / | 446.2722 | 16.69 | 1 | + | + | + | + |
| / | 446.7472 | 11.52 | 2 | + | + | + | + |
| / | 446.7659 | 14.62 | 2 | + | + | + | + |
| / | 447.2085 | 13.59 | 1 | + | + | + | + |
| / | 447.2105 | 6.30 | 1 | + | + | + | + |
| / | 447.2542 | 14.60 | 1 | + | + | + | + |
| / | 448.2467 | 10.36 | 2 | + | + | + | + |
| / | 449.7704 | 16.48 | 2 | + | + | + | + |
| / | 451.2280 | 22.27 | 1 | + | + | + | + |
| / | 453.2203 | 12.27 | | + | + | + | + |
| / | 454.7644 | 13.80 | 2 | + | + | + | + |
| / | 455.2042 | 19.61 | 1 | + | + | + | + |
| / | 456.2434 | 8.94 | 2 | + | + | + | + |
| / | 456.2456 | 13.15 | 2 | + | + | + | + |
| / | 456.2925 | 23.26 | 1 | + | + | + | + |
| / | 457.2030 | 14.88 | 2 | + | + | + | + |
| / | 457.7509 | 12.27 | 2 | + | + | + | + |
| / | 458.2476 | 12.10 | 2 | + | + | + | + |
| / | 459.1892 | 12.27 | 2 | + | + | + | + |
| / | 459.2278 | 19.63 | 3 | + | + | + | + |

FIG. 12 (Continued)

| | | | | | | | |
|---|---|---|---|---|---|---|---|
| / | 459.2678 | 10.98 | 1 | + | + | + | + |
| / | 459.2685 | 5.59 | 1 | + | + | + | + |
| / | 459.2935 | 21.96 | 1 | + | + | + | + |
| / | 462.2302 | 6.30 | 1 | + | + | + | + |
| / | 462.2472 | 19.19 | 1 | + | + | + | + |
| / | 464.2263 | 13.90 | 1 | + | + | + | + |
| / | 464.7522 | 12.26 | 2 | + | + | + | + |
| / | 465.2464 | 14.88 | 1 | + | + | + | + |
| / | 467.7294 | 17.95 | 2 | + | + | + | + |
| / | 467.7517 | 11.01 | 2 | + | + | + | + |
| / | 468.2369 | 11.52 | 1 | + | + | + | + |
| / | 471.7388 | 12.84 | 2 | + | + | + | + |
| / | 472.2880 | 13.31 | 1 | + | + | + | + |
| / | 472.2893 | 21.02 | 1 | + | + | + | + |
| / | 472.2992 | 9.40 | 1 | + | + | + | + |
| / | 472.5596 | 18.89 | 3 | + | + | + | + |
| / | 473.2079 | 18.21 | 2 | + | + | + | + |
| / | 473.2346 | 5.59 | | + | + | + | - |
| / | 474.2428 | 11.52 | 1 | + | + | + | + |
| / | 474.2429 | 10.08 | 1 | + | + | + | + |
| / | 474.2679 | 12.27 | 2 | + | + | + | + |

FIG. 12 (Continued)

| | | | | | | | |
|---|---|---|---|---|---|---|---|
| / | 474.2682 | 12.27 | 1 | + | + | + | + |
| / | 474.2799 | 5.31 | 1 | + | + | + | + |
| / | 475.7502 | 10.57 | 2 | + | + | + | + |
| / | 476.2273 | 18.89 | 1 | + | + | + | + |
| / | 476.2476 | 12.35 | 2 | + | + | + | + |
| / | 478.7565 | 13.59 | 2 | + | + | + | + |
| / | 479.2622 | 17.50 | 1 | + | + | + | + |
| / | 479.7979 | 12.78 | 2 | + | + | + | + |
| / | 480.2565 | 21.76 | 1 | + | + | + | + |
| / | 484.2314 | 6.30 | 2 | + | + | + | + |
| / | 486.3042 | 14.60 | 1 | + | + | + | + |
| / | 486.3052 | 14.62 | 1 | + | + | + | + |
| / | 490.2600 | 5.59 | | + | + | + | + |
| / | 493.2424 | 19.19 | 1 | + | + | + | + |
| / | 498.7538 | 9.63 | 2 | + | + | + | + |
| / | 499.2625 | 7.80 | 1 | + | + | + | + |
| / | 499.7645 | 21.01 | 2 | + | + | + | + |
| / | 501.2429 | 6.30 | 1 | + | + | + | + |
| / | 501.7630 | 24.02 | 2 | + | + | + | + |
| / | 504.7541 | 12.50 | 2 | + | + | + | - |
| / | 507.7421 | 19.80 | 2 | + | + | + | + |

FIG. 12 (Continued)

| | | | | | | | |
|---|---|---|---|---|---|---|---|
| / | 508.2906 | 15.50 | 1 | + | + | + | + |
| / | 509.7630 | 19.19 | 2 | + | + | + | + |
| / | 510.2391 | 16.77 | 2 | + | + | + | + |
| / | 511.2845 | 23.66 | 2 | + | + | + | + |
| / | 511.7312 | 19.81 | 2 | + | + | + | + |
| / | 512.2539 | 16.68 | 2 | + | + | + | + |
| / | 512.5736 | 19.63 | 3 | + | + | + | + |
| / | 512.7552 | 24.02 | 2 | + | + | + | + |
| / | 513.7482 | 20.49 | 2 | + | + | + | + |
| / | 515.2510 | 19.50 | 2 | + | + | + | + |
| / | 515.3429 | 10.06 | 1 | + | + | + | + |
| / | 518.7344 | 19.81 | 2 | + | + | + | + |
| / | 520.7371 | 24.02 | 2 | + | + | + | + |
| / | 520.9586 | 20.16 | 3 | - | + | + | - |
| / | 524.7756 | 11.14 | 2 | - | + | + | - |
| / | 524.8132 | 17.94 | 2 | + | + | + | - |
| / | 525.7364 | 25.65 | 2 | - | - | + | + |
| / | 526.2750 | 5.31 | 1 | + | + | + | + |
| / | 526.7177 | 19.81 | 2 | + | + | + | + |
| / | 527.2957 | 12.10 | 1 | + | + | + | + |
| / | 528.9272 | 20.10 | 3 | + | + | + | - |

FIG. 12 (Continued)

| | | | | | | | |
|---|---|---|---|---|---|---|---|
| / | 529.6020 | 19.40 | 3 | + | + | + | + |
| / | 530.7887 | 18.89 | 2 | + | + | + | + |
| / | 530.9570 | 19.63 | 3 | + | + | + | + |
| / | 531.2907 | 12.27 | 1 | + | + | + | + |
| / | 531.7855 | 12.78 | 2 | + | + | + | + |
| / | 534.1999 | 19.81 | 2 | + | + | + | + |
| / | 534.2432 | 6.30 | 1 | + | + | + | + |
| / | 535.2696 | 14.08 | 1 | + | + | + | + |
| / | 535.8036 | 17.75 | 2 | + | + | + | + |
| / | 536.7798 | 12.35 | 2 | + | + | + | - |
| / | 538.2274 | 12.65 | 2 | + | + | + | + |
| / | 538.2836 | 19.63 | 3 | + | + | + | + |
| / | 538.7866 | 17.27 | 2 | + | + | + | + |
| / | 539.7781 | 28.50 | 2 | + | + | + | + |
| / | 542.7990 | 14.46 | 2 | + | + | + | + |
| / | 543.6046 | 19.63 | 3 | + | + | + | + |
| / | 544.2973 | 12.40 | 1 | + | + | + | + |
| / | 544.3862 | 26.81 | 1 | + | + | + | + |
| / | 544.7864 | 16.68 | 2 | + | + | + | + |
| / | 544.7866 | 17.43 | 2 | + | + | + | + |
| / | 545.3081 | 14.46 | 2 | + | + | + | + |

FIG. 12 (Continued)

| | | | | | | | |
|---|---|---|---|---|---|---|---|
| / | 546.7834 | 16.04 | 2 | + | + | + | + |
| / | 547.7753 | 27.08 | 2 | + | + | + | + |
| / | 548.9296 | 19.63 | 3 | + | + | + | + |
| / | 550.7959 | 14.24 | 2 | + | + | + | + |
| / | 552.6142 | 12.58 | 3 | + | + | + | + |
| / | 553.3052 | 13.59 | 2 | + | + | + | + |
| / | 553.7987 | 13.56 | 2 | + | + | + | + |
| / | 556.3212 | 12.55 | 1 | + | + | + | + |
| / | 556.7927 | 17.20 | 2 | + | + | + | + |
| / | 558.3128 | 5.59 | | + | + | + | + |
| / | 558.7653 | 27.09 | 2 | + | + | + | + |
| / | 560.3174 | 13.31 | 1 | + | + | + | + |
| / | 561.3171 | 24.91 | 1 | + | + | + | + |
| / | 562.2794 | 12.78 | 1 | + | + | + | + |
| / | 563.8012 | 17.94 | 2 | + | + | + | + |
| / | 564.2834 | 15.75 | 1 | + | + | + | + |
| / | 564.2942 | 13.60 | 2 | + | + | + | + |
| / | 568.2868 | 6.30 | 1 | + | + | + | + |
| / | 569.6130 | 14.46 | 3 | + | + | + | + |
| / | 569.7932 | 10.06 | 2 | + | + | + | + |
| / | 570.3125 | 12.10 | 1 | + | + | + | + |

FIG. 12 (Continued)

| / | 571.2687 | 13.00 | 1 | - | + | + | + |
|---|---|---|---|---|---|---|---|
| / | 571.2819 | 12.27 | 1 | + | + | + | + |
| / | 571.3244 | 19.81 | 1 | + | + | + | - |
| / | 572.2779 | 13.60 | 2 | + | + | + | + |
| / | 572.3803 | 25.69 | 1 | + | + | + | + |
| / | 573.2504 | 14.46 | 2 | + | + | + | + |
| / | 573.2644 | 5.31 | 1 | + | + | + | + |
| / | 573.3398 | 23.14 | 1 | + | + | + | + |
| / | 574.2337 | 27.09 | 2 | + | + | + | + |
| / | 575.3018 | 14.46 | 2 | + | + | + | + |
| / | 578.2752 | 5.31 | 1 | + | + | + | + |
| / | 578.3000 | 12.27 | 2 | + | + | + | + |
| / | 578.3056 | 12.53 | 1 | + | + | + | + |
| / | 579.7647 | 13.59 | 2 | + | + | + | + |
| / | 581.2635 | 19.63 | 2 | + | + | + | + |
| / | 581.3193 | 11.52 | 1 | + | + | + | + |
| / | 581.8293 | 17.50 | 2 | + | + | + | + |
| / | 583.8135 | 12.10 | 2 | + | + | + | + |
| / | 584.3129 | 6.30 |  | + | + | + | + |
| / | 586.3359 | 16.42 | 1 | + | + | + | + |
| / | 587.1737 | 14.08 | 1 | + | + | + | + |

FIG. 12 (Continued)

|   |          |       |   |   |   |   |   |
|---|----------|-------|---|---|---|---|---|
| / | 587.3193 | 16.26 | 1 | + | + | + | - |
| / | 588.8368 | 16.04 | 2 | + | + | + | + |
| / | 589.3338 | 15.44 | 1 | + | + | + | + |
| / | 591.8236 | 21.95 | 2 | + | + | + | - |
| / | 594.2725 | 14.46 | 2 | + | + | + | + |
| / | 596.3298 | 12.10 | 1 | + | + | + | + |
| / | 596.8323 | 14.97 | 2 | + | + | + | + |
| 1 | 596.8454 | 18.90 | 2 | - | - | + | - |
| / | 599.3923 | 22.27 | 1 | + | + | + | + |
| / | 600.2304 | 12.78 |   | + | + | + | + |
| / | 600.3867 | 20.13 | 1 | + | + | + | + |
| / | 601.3122 | 18.39 | 2 | + | + | + | + |
| / | 602.2936 | 14.24 | 1 | + | + | + | + |
| / | 602.3390 | 8.27  | 1 | + | + | + | + |
| / | 603.2689 | 22.63 | 2 | + | + | + | + |
| / | 604.2905 | 12.35 | 1 | + | + | + | + |
| / | 604.3075 | 9.40  | 1 | + | + | + | + |
| 2 | 604.8556 | 17.84 | 2 | - | - | + | - |
| / | 607.2546 | 15.50 | 1 | + | + | + | + |
| / | 607.2905 | 19.63 | 1 | + | + | + | + |
| / | 607.8255 | 14.80 | 2 | + | + | + | + |

FIG. 12 (Continued)

| | | | | | | | |
|---|---|---|---|---|---|---|---|
| / | 608.3549 | 16.74 | 1 | + | + | + | + |
| / | 609.8244 | 17.75 | 2 | + | + | + | + |
| / | 618.3392 | 12.35 | 1 | + | + | + | + |
| / | 621.3747 | 21.95 | 1 | + | + | + | + |
| / | 621.9774 | 17.10 | 3 | + | + | + | - |
| / | 624.3507 | 15.75 | 1 | + | + | + | + |
| / | 628.3564 | 12.10 | 2 | + | + | + | + |
| / | 629.8132 | 12.78 | 2 | + | + | + | + |
| / | 641.3310 | 23.36 | 2 | + | + | + | + |
| / | 643.3687 | 16.42 | 1 | + | + | + | + |
| / | 644.3510 | 10.06 | 1 | + | + | + | + |
| / | 644.8290 | 16.75 | 2 | + | + | + | - |
| / | 646.7862 | 21.95 | 2 | + | + | + | + |
| / | 647.3307 | 17.75 | 1 | + | + | + | + |
| / | 648.3511 | 20.10 | 2 | + | + | + | + |
| / | 648.8497 | 23.36 | 2 | + | + | + | + |
| / | 649.3000 | 19.82 | 1 | + | + | + | + |
| / | 649.3232 | 22.63 | 2 | + | + | + | + |
| / | 654.3328 | 17.94 | 2 | + | + | + | + |
| / | 655.3930 | 13.03 | 1 | + | + | + | + |
| / | 655.8360 | 14.50 | 2 | + | + | + | - |

FIG. 12 (Continued)

| | | | | | | | |
|---|---|---|---|---|---|---|---|
| / | 656.8466 | 21.95 | 2 | + | + | + | + |
| / | 660.3497 | 15.00 | 2 | + | + | + | + |
| / | 662.3516 | 17.34 | 2 | + | + | + | + |
| / | 664.8443 | 20.70 | 2 | + | + | + | + |
| / | 666.8469 | 13.20 | 2 | + | + | + | + |
| / | 670.3497 | 15.50 | 2 | + | + | + | + |
| / | 670.4318 | 23.36 | 1 | + | + | + | + |
| / | 672.3542 | 18.90 | 2 | + | + | + | + |
| / | 672.8430 | 20.00 | 2 | + | + | + | + |
| / | 677.3781 | 10.98 | 1 | + | + | + | + |
| / | 683.8020 | 20.49 | 2 | + | + | + | + |
| / | 688.4038 | 20.13 | 1 | + | + | + | + |
| / | 690.3999 | 25.69 | 1 | - | + | + | - |
| / | 694.4061 | 11.52 | 1 | + | + | + | + |
| / | 696.8466 | 13.03 | 2 | + | + | + | - |
| / | 703.3402 | 14.46 | 2 | + | + | + | + |
| / | 705.8646 | 21.52 | 2 | + | + | + | - |
| / | 708.3562 | 18.89 | 2 | + | + | + | + |
| / | 708.6879 | 14.08 | 3 | + | + | + | + |
| / | 710.8729 | 15.35 | 2 | + | + | + | + |
| / | 713.0401 | 19.05 | 3 | + | + | + | - |

FIG. 12 (Continued)

| | | | | | | | |
|---|---|---|---|---|---|---|---|
| / | 718.2710 | 14.08 | 1 | + | + | + | + |
| / | 718.7115 | 18.11 | 3 | + | + | + | - |
| / | 723.3107 | 13.49 | 1 | + | + | + | + |
| / | 723.7094 | 17.26 | 3 | + | + | + | - |
| / | 724.0438 | 17.34 | 3 | + | + | + | - |
| / | 726.3114 | 20.13 | 2 | + | + | + | + |
| / | 726.3605 | 11.86 | 1 | + | + | + | + |
| / | 730.3692 | 16.42 | 2 | + | + | + | + |
| / | 732.3417 | 17.04 | 1 | + | + | + | + |
| / | 745.3828 | 5.59 |  | + | + | + | + |
| / | 745.8669 | 15.33 | 2 | - | + | + | - |
| / | 748.3914 | 12.40 | 1 | + | + | + | + |
| / | 749.0318 | 14.89 | 3 | + | + | + | + |
| / | 753.8639 | 14.89 | 2 | + | + | + | + |
| / | 755.7079 | 15.33 | 3 | + | + | + | + |
| / | 757.4285 | 24.97 | 1 | + | + | + | - |
| / | 761.0394 | 14.46 | 3 | + | + | + | + |
| / | 765.9196 | 20.10 | 2 | + | + | + | - |
| / | 766.7067 | 13.88 | 3 | + | + | + | + |
| 3 | 766.8957 | 18.34 | 2 | - | - | + | - |
| / | 767.4245 | 8.27 | 1 | + | + | + | - |

FIG. 12 (Continued)

| / | 767.7089 | 14.89 | 3 | + | + | + | - |
|---|---|---|---|---|---|---|---|
| / | 771.3333 | 10.39 | 1 | + | + | + | + |
| / | 773.3523 | 12.10 |   | + | + | + | + |
| / | 778.3712 | 14.88 | 2 | + | + | + | + |
| / | 780.9306 | 20.10 | 2 | - | + | + | + |
| / | 781.9127 | 22.43 | 2 | + | + | + | + |
| / | 781.9374 | 21.52 | 2 | + | + | + | + |
| / | 783.4554 | 13.03 | 1 | + | + | + | + |
| / | 784.8969 | 20.13 | 2 | + | + | + | + |
| / | 785.4468 | 10.98 | 1 | + | + | + | - |
| / | 785.8968 | 19.81 | 2 | + | + | + | + |
| / | 790.9093 | 15.95 | 2 | - | + | + | - |
| / | 792.8801 | 18.34 | 2 | + | + | + | + |
| / | 793.8986 | 19.40 | 2 | + | + | + | + |
| / | 795.9306 | 19.61 | 2 | + | + | + | + |
| / | 800.3909 | 11.86 | 2 | + | + | + | - |
| / | 804.8810 | 13.59 | 2 | + | + | + | + |
| / | 811.4610 | 12.30 | 1 | + | + | + | + |
| / | 811.4614 | 13.13 | 1 | + | + | + | - |
| / | 811.4615 | 13.20 | 1 | + | + | + | - |
| / | 811.4623 | 12.27 | 1 | + | + | + | + |

FIG. 12 (Continued)

| / | 811.4634 | 12.10 | 1 | + | + | + | + |
|---|---|---|---|---|---|---|---|
| / | 811.7179 | 18.34 | 3 | + | + | + | + |
| / | 813.4302 | 15.75 | 1 | + | + | + | + |
| / | 816.4244 | 16.24 | 2 | + | + | + | + |
| / | 821.3904 | 21.20 | 1 | + | + | + | + |
| / | 823.5000 | 15.75 | 1 | + | + | + | - |
| / | 824.4354 | 19.63 | 2 | + | + | + | + |
| / | 834.7436 | 17.43 | 3 | + | + | + | + |
| / | 841.4766 | 20.13 | 1 | + | + | + | + |
| / | 842.9218 | 18.95 | 2 | - | + | + | - |
| / | 844.4641 | 23.36 | 1 | + | + | + | - |
| / | 845.4240 | 22.27 | 3 | + | + | + | + |
| / | 845.9125 | 15.33 | 2 | + | + | + | + |
| / | 850.4249 | 21.02 | 3 | + | + | + | + |
| / | 852.4311 | 17.04 | 1 | + | + | + | + |
| / | 854.4121 | 14.46 | 2 | + | + | + | + |
| / | 868.4834 | 10.62 | 1 | + | + | + | + |
| / | 874.5250 | 31.78 | 1 | + | + | + | + |
| / | 874.7801 | 17.92 | 3 | + | + | + | + |
| / | 892.5215 | 14.62 | 1 | + | + | + | + |
| / | 898.5327 | 16.42 | 1 | + | + | + | + |

FIG. 12 (Continued)

| / | 926.5504 | 23.66 | 1 | + | + | + | + |
|---|---|---|---|---|---|---|---|
| / | 928.4948 | 12.27 | 1 | + | + | + | + |
| / | 934.4512 | 17.75 | 1 | + | + | + | + |
| / | 1008.4980 | 12.55 | 1 | + | + | + | - |
| / | 1014.4776 | 19.81 | 1 | + | + | + | + |
| / | 1018.5114 | 19.19 | 1 | + | + | + | + |
| / | 1021.5555 | 23.66 | | + | + | + | + |
| / | 1029.4871 | 19.50 | 1 | + | + | + | + |
| / | 1088.5613 | 17.34 | 1 | + | + | + | + |
| / | 1092.5548 | 16.04 | 1 | + | + | + | + |
| / | 1094.5447 | 27.08 | 1 | + | + | + | + |
| / | 1105.5997 | 13.59 | 1 | + | + | + | + |
| / | 1149.5944 | 14.46 | 1 | + | + | + | + |
| / | 1192.6607 | 15.00 | 1 | + | + | + | + |

FIG. 12 (Continued)

Table 4

| Pig marker No. | m/z | RT (min) | Charge | Donkey | Horse | Cattle | Pig |
|---|---|---|---|---|---|---|---|
| / | 189.1288 | 5.31 | 1 | + | + | + | + |
| / | 216.6198 | 8.26 | 2 | + | + | + | + |
| / | 219.1404 | 10.98 | 1 | + | + | + | + |
| / | 223.1141 | 8.27 | 1 | + | + | + | + |
| / | 224.1352 | 31.00 | 1 | + | + | + | + |
| / | 228.6384 | 5.31 | 2 | + | + | + | + |
| / | 229.6280 | 12.09 | 2 | + | + | + | + |
| / | 231.1762 | 10.44 | 1 | + | + | + | + |
| / | 231.1771 | 7.77 | | + | + | + | + |
| / | 233.1565 | 5.55 | 1 | + | + | + | + |
| / | 234.1024 | 22.27 | | + | + | + | + |
| / | 236.6544 | 9.34 | 2 | + | + | + | + |
| / | 237.6260 | 10.08 | 2 | + | + | + | + |
| / | 237.6447 | 5.31 | 2 | + | + | + | + |
| / | 242.1565 | 10.08 | 1 | + | + | + | + |
| / | 243.1408 | 15.75 | 1 | + | + | + | + |
| / | 245.1925 | 14.24 | 1 | + | + | + | + |
| / | 245.1925 | 15.38 | 1 | + | + | + | + |
| / | 249.6631 | 10.08 | 2 | + | + | + | + |

FIG. 13

| / | 250.1855 | 32.78 | 1 | + | + | + | + |
|---|---|---|---|---|---|---|---|
| / | 258.1766 | 10.10 | 2 | + | + | + | + |
| / | 260.1678 | 9.58 | 1 | + | + | + | + |
| / | 260.2043 | 6.27 | 1 | + | + | + | + |
| / | 265.1621 | 13.32 | 1 | + | + | + | + |
| / | 267.6266 | 6.27 | 2 | + | + | + | + |
| / | 270.2001 | 10.08 | 1 | + | + | + | + |
| / | 272.1795 | 9.40 | 1 | + | + | + | + |
| / | 272.6535 | 12.27 | 2 | + | + | + | + |
| / | 274.1954 | 10.08 | 1 | + | + | + | + |
| / | 276.1632 | 7.57 | 1 | + | + | + | + |
| / | 277.1257 | 9.74 | 1 | + | + | + | + |
| / | 278.6662 | 12.50 | 2 | + | + | + | + |
| / | 279.1418 | 17.53 | 1 | + | + | + | + |
| / | 279.1777 | 18.20 | 1 | + | + | + | + |
| / | 281.1213 | 10.08 | 1 | + | + | + | + |
| / | 281.1566 | 5.59 | 1 | + | + | + | + |
| / | 283.8095 | 12.27 | 2 | + | + | + | + |
| / | 288.2009 | 20.49 | | + | + | + | + |
| / | 288.2116 | 6.30 | | + | + | + | + |
| / | 290.1784 | 6.30 | | + | + | + | + |

FIG. 13 (Continued)

| | | | | | | | |
|---|---|---|---|---|---|---|---|
| / | 292.6630 | 12.27 | 2 | + | + | + | + |
| / | 295.1730 | 10.98 | 1 | + | + | + | + |
| / | 295.1740 | 10.08 | 1 | + | + | + | + |
| / | 297.6402 | 12.50 | 2 | + | + | + | + |
| / | 300.6175 | 12.78 | 2 | + | + | + | + |
| / | 301.1832 | 6.30 | 2 | + | + | + | + |
| / | 301.6758 | 8.27 | 2 | + | + | + | + |
| / | 301.6768 | 14.24 | 2 | + | + | + | + |
| / | 302.1801 | 10.08 | 1 | + | + | + | + |
| / | 302.2159 | 19.22 | 1 | + | + | + | + |
| / | 302.2166 | 18.21 | 1 | + | + | + | + |
| / | 303.6207 | 6.30 | 1 | + | + | + | + |
| / | 305.6956 | 11.52 | 2 | + | + | + | + |
| / | 306.1484 | 23.08 | 2 | + | + | + | + |
| / | 306.1739 | 6.30 | | + | + | + | + |
| / | 309.6738 | 12.35 | 2 | + | + | + | + |
| / | 312.8329 | 16.42 | 3 | + | + | + | + |
| / | 314.6831 | 12.07 | 2 | + | + | + | + |
| / | 316.2312 | 19.63 | 1 | + | + | + | + |
| / | 317.1910 | 6.30 | 3 | + | + | + | + |
| / | 320.1733 | 14.88 | 1 | + | + | + | + |

FIG. 13 (Continued)

| / | 320.2031 | 12.78 | 3 | + | + | + | + |
|---|---|---|---|---|---|---|---|
| / | 321.1817 | 5.59 | 1 | + | + | + | + |
| / | 322.6805 | 10.06 | 2 | + | + | + | + |
| / | 322.8205 | 12.27 | 3 | + | + | + | + |
| / | 323.1587 | 6.30 | | + | + | + | + |
| / | 323.4940 | 6.30 | | + | + | + | + |
| / | 324.1811 | 5.59 | 2 | + | + | + | + |
| / | 327.8098 | 12.27 | 3 | + | + | + | + |
| / | 329.1909 | 6.30 | 2 | + | + | + | + |
| / | 329.2007 | 5.31 | 1 | + | + | + | + |
| / | 329.2282 | 15.00 | 2 | + | + | + | + |
| / | 330.1635 | 19.95 | 1 | + | + | + | + |
| / | 330.2011 | 12.78 | 2 | + | + | + | + |
| / | 332.2266 | 14.24 | 1 | + | + | + | + |
| / | 332.2273 | 18.89 | 1 | + | + | + | + |
| / | 335.1611 | 21.76 | 3 | + | + | + | + |
| / | 339.1935 | 10.87 | 2 | + | + | + | + |
| / | 339.6729 | 11.52 | 2 | + | + | + | + |
| / | 343.2051 | 12.27 | | + | + | + | + |
| / | 344.2632 | 20.16 | 1 | + | + | + | + |
| / | 345.1529 | 9.63 | 1 | + | + | + | + |

FIG. 13 (Continued)

| | | | | | | |
|---|---|---|---|---|---|---|
| / | 345.2333 | 5.31 | 1 | + | + | + | + |
| / | 347.2014 | 7.77 | 1 | + | + | + | + |
| / | 347.7072 | 11.46 | 2 | + | + | + | + |
| / | 350.1806 | 9.63 | 1 | + | + | + | + |
| / | 350.6348 | 14.08 | 2 | + | + | + | + |
| / | 353.4912 | 14.88 | 3 | + | + | + | + |
| / | 359.2392 | 10.08 | 1 | + | + | + | + |
| / | 359.6404 | 14.08 | 2 | + | + | + | + |
| / | 366.2176 | 17.35 | 2 | + | + | + | + |
| / | 369.2061 | 13.59 | 3 | + | + | + | + |
| / | 369.7033 | 6.30 | 2 | + | + | + | + |
| / | 371.2385 | 10.98 | 1 | + | + | + | + |
| / | 371.7236 | 16.41 | 2 | + | + | + | + |
| / | 372.2159 | 10.36 | 2 | + | + | + | + |
| / | 372.6956 | 5.59 | 2 | + | + | + | + |
| / | 373.2899 | 6.30 | 1 | + | + | + | + |
| / | 374.2389 | 18.89 | 1 | + | + | + | + |
| / | 374.7011 | 12.41 | 2 | + | + | + | + |
| / | 374.8536 | 14.46 | 3 | + | + | + | + |
| / | 375.2342 | 7.77 | 1 | + | + | + | + |
| / | 377.1926 | 13.59 | 1 | + | + | + | + |

FIG. 13 (Continued)

| / | 377.1953 | 11.46 | 1 | + | + | + | + |
| --- | --- | --- | --- | --- | --- | --- | --- |
| / | 378.6137 | 14.08 | 2 | + | + | + | + |
| / | 379.2181 | 24.94 | 2 | + | + | + | + |
| / | 379.7035 | 10.98 | 2 | + | + | + | + |
| / | 379.8415 | 14.46 | 3 | + | + | + | + |
| / | 381.8550 | 13.59 | 3 | + | + | + | + |
| / | 382.5030 | 14.46 | 3 | + | + | + | + |
| / | 385.2063 | 8.27 | 2 | + | + | + | + |
| / | 385.2297 | 10.08 | 1 | + | + | + | + |
| / | 385.2661 | 9.40 | 1 | + | + | + | + |
| / | 386.8436 | 13.59 | 3 | + | + | + | + |
| / | 387.8462 | 19.63 | 3 | + | + | + | + |
| / | 388.2293 | 6.30 | | + | + | + | + |
| / | 388.2296 | 12.27 | | + | + | + | + |
| / | 389.2488 | 11.01 | 1 | + | + | + | + |
| / | 390.2222 | 10.60 | 2 | + | + | + | + |
| / | 391.1910 | 5.31 | 1 | + | + | + | + |
| / | 391.2092 | 18.32 | 1 | + | + | + | + |
| / | 392.2315 | 13.05 | 2 | + | + | + | + |
| / | 393.2091 | 9.40 | 2 | + | + | + | + |
| / | 395.6893 | 8.94 | 2 | + | + | + | + |

FIG. 13 (Continued)

| | | | | | | | |
|---|---|---|---|---|---|---|---|
| / | 396.2707 | 14.62 | 1 | + | + | + | + |
| / | 398.1658 | 6.30 | | + | + | - | + |
| / | 398.2272 | 15.00 | 3 | + | + | + | + |
| / | 398.2504 | 14.18 | 1 | + | + | + | + |
| / | 399.2711 | 17.34 | 1 | + | + | + | + |
| / | 400.2297 | 9.40 | 1 | + | + | + | + |
| / | 400.2298 | 12.78 | 2 | + | + | + | + |
| / | 402.2567 | 10.08 | 1 | + | + | + | + |
| / | 402.5164 | 22.63 | 3 | + | + | + | + |
| / | 403.2657 | 15.00 | 1 | + | + | + | + |
| / | 404.2236 | 9.40 | 1 | + | + | + | + |
| / | 404.4604 | 19.63 | 4 | + | + | + | + |
| / | 405.2186 | 9.63 | 2 | + | + | + | + |
| / | 406.2358 | 12.21 | 2 | + | + | + | + |
| / | 407.2195 | 15.76 | 2 | + | + | + | + |
| / | 407.9573 | 19.63 | 4 | + | + | + | + |
| / | 410.8747 | 15.00 | 3 | + | + | + | + |
| / | 411.2322 | 10.98 | 1 | + | + | + | + |
| / | 411.6992 | 19.63 | 4 | + | + | + | + |
| / | 412.2536 | 16.04 | 2 | + | + | + | + |
| / | 412.2540 | 15.75 | 2 | + | + | + | + |

FIG. 13 (Continued)

|   |          |       |   |   |   |   |   |
|---|----------|-------|---|---|---|---|---|
| / | 413.2410 | 14.18 | 2 | + | + | + | + |
| / | 413.2866 | 21.76 | 1 | + | + | + | + |
| / | 414.2413 | 14.88 | 3 | + | + | + | + |
| / | 414.2457 | 12.27 | 1 | + | + | + | + |
| / | 415.2447 | 22.63 | 1 | + | + | + | + |
| / | 415.8626 | 15.00 | 3 | + | + | + | + |
| / | 418.2195 | 17.95 | 1 | + | + | + | + |
| / | 418.7339 | 10.36 | 2 | + | + | + | + |
| 1 | 419.2446 | 14.04 | 2 | - | - | - | + |
| / | 420.1979 | 13.01 | 1 | + | + | + | + |
| / | 421.2412 | 12.45 | 2 | + | + | + | + |
| / | 421.2432 | 20.13 | 2 | + | + | + | + |
| / | 421.2612 | 15.00 | 2 | + | + | + | + |
| / | 421.7331 | 9.63  | 2 | + | + | + | + |
| / | 422.2127 | 5.31  | 1 | + | + | + | + |
| / | 426.7299 | 8.94  | 2 | + | + | + | + |
| / | 429.2457 | 22.30 | 1 | + | + | + | + |
| / | 429.2826 | 21.01 | 1 | + | + | + | + |
| / | 430.2411 | 12.78 | 1 | + | + | + | + |
| / | 430.2775 | 20.63 | 1 | + | + | + | + |
| / | 431.2253 | 13.59 | 2 | + | + | + | + |

FIG. 13 (Continued)

| | | | | | | | |
|---|---|---|---|---|---|---|---|
| / | 431.2478 | 6.30 | 1 | + | + | + | + |
| / | 431.5276 | 21.95 | 3 | + | + | + | + |
| / | 432.2315 | 8.27 | 1 | + | + | + | + |
| / | 434.2619 | 17.34 | 2 | + | + | + | + |
| / | 434.7471 | 10.81 | 2 | + | + | + | + |
| / | 437.7673 | 31.77 | 2 | + | + | + | + |
| / | 441.2521 | 20.49 | 2 | + | + | + | + |
| / | 441.7730 | 18.54 | 2 | + | + | + | + |
| / | 442.7441 | 12.27 | 2 | + | + | + | + |
| / | 443.2353 | 6.30 | 1 | + | + | + | + |
| / | 444.2303 | 10.08 | 2 | + | + | + | + |
| / | 444.2936 | 20.49 | 1 | + | + | + | + |
| / | 445.2527 | 7.80 | 1 | + | + | + | + |
| / | 446.2717 | 8.27 | 1 | + | + | + | + |
| / | 446.2722 | 16.69 | 1 | + | + | + | + |
| / | 446.7472 | 11.52 | 2 | + | + | + | + |
| / | 446.7659 | 14.62 | 2 | + | + | + | + |
| / | 447.2085 | 13.59 | 1 | + | + | + | + |
| / | 447.2105 | 6.30 | 1 | + | + | + | + |
| / | 447.2542 | 14.60 | 1 | + | + | + | + |
| / | 448.2467 | 10.36 | 2 | + | + | + | + |

FIG. 13 (Continued)

| | | | | | | | |
|---|---|---|---|---|---|---|---|
| / | 449.7704 | 16.48 | 2 | + | + | + | + |
| / | 451.2280 | 22.27 | 1 | + | + | + | + |
| / | 453.2203 | 12.27 | | + | + | + | + |
| / | 454.7644 | 13.80 | 2 | + | + | + | + |
| / | 455.2042 | 19.61 | 1 | + | + | + | + |
| / | 456.2434 | 8.94 | 2 | + | + | + | + |
| / | 456.2456 | 13.15 | 2 | + | + | + | + |
| / | 456.2925 | 23.26 | 1 | + | + | + | + |
| / | 457.2030 | 14.88 | 2 | + | + | + | + |
| / | 457.7509 | 12.27 | 2 | + | + | + | + |
| / | 458.2476 | 12.10 | 2 | + | + | + | + |
| / | 459.1892 | 12.27 | 2 | + | + | + | + |
| / | 459.2278 | 19.63 | 3 | + | + | + | + |
| / | 459.2678 | 10.98 | 1 | + | + | + | + |
| / | 459.2685 | 5.59 | 1 | + | + | + | + |
| / | 459.2935 | 21.96 | 1 | + | + | + | + |
| / | 462.2302 | 6.30 | 1 | + | + | + | + |
| / | 462.2472 | 19.19 | 1 | + | + | + | + |
| / | 464.2263 | 13.90 | 1 | + | + | + | + |
| / | 464.7522 | 12.26 | 2 | + | + | + | + |
| / | 465.2464 | 14.88 | 1 | + | + | + | + |

FIG. 13 (Continued)

| | | | | | | | |
|---|---|---|---|---|---|---|---|
| / | 467.7294 | 17.95 | 2 | + | + | + | + |
| / | 467.7517 | 11.01 | 2 | + | + | + | + |
| / | 468.2369 | 11.52 | 1 | + | + | + | + |
| / | 471.7388 | 12.84 | 2 | + | + | + | + |
| / | 472.2880 | 13.31 | 1 | + | + | + | + |
| / | 472.2893 | 21.02 | 1 | + | + | + | + |
| / | 472.2992 | 9.40 | 1 | + | + | + | + |
| / | 472.5596 | 18.89 | 3 | + | + | + | + |
| / | 473.2079 | 18.21 | 2 | + | + | + | + |
| / | 474.2428 | 11.52 | 1 | + | + | + | + |
| / | 474.2429 | 10.08 | 1 | + | + | + | + |
| / | 474.2679 | 12.27 | 2 | + | + | + | + |
| / | 474.2682 | 12.27 | 1 | + | + | + | + |
| / | 474.2799 | 5.31 | 1 | + | + | + | + |
| / | 475.7502 | 10.57 | 2 | + | + | + | + |
| / | 476.2273 | 18.89 | 1 | + | + | + | + |
| / | 476.2476 | 12.35 | 2 | + | + | + | + |
| / | 478.2575 | 16.50 | 2 | + | + | - | + |
| / | 478.7565 | 13.59 | 2 | + | + | + | + |
| / | 479.2622 | 17.50 | 1 | + | + | + | + |
| / | 479.7979 | 12.78 | 2 | + | + | + | + |

FIG. 13 (Continued)

|   |          |       |   |   |   |   |   |
|---|----------|-------|---|---|---|---|---|
| / | 480.2565 | 21.76 | 1 | + | + | + | + |
| / | 484.2314 | 6.30  | 2 | + | + | + | + |
| / | 486.3042 | 14.60 | 1 | + | + | + | + |
| / | 486.3052 | 14.62 | 1 | + | + | + | + |
| / | 490.2600 | 5.59  |   | + | + | + | + |
| / | 493.2424 | 19.19 | 1 | + | + | + | + |
| / | 498.7538 | 9.63  | 2 | + | + | + | + |
| / | 499.2625 | 7.80  | 1 | + | + | + | + |
| 2 | 490.5942 | 14.40 | 3 | - | - | - | + |
| / | 499.7645 | 21.01 | 2 | + | + | + | + |
| / | 501.2429 | 6.30  | 1 | + | + | + | + |
| / | 501.7630 | 24.02 | 2 | + | + | + | + |
| / | 507.7421 | 19.80 | 2 | + | + | + | + |
| / | 508.2906 | 15.50 | 1 | + | + | + | + |
| / | 509.7630 | 19.19 | 2 | + | + | + | + |
| / | 510.2391 | 16.77 | 2 | + | + | + | + |
| / | 511.2845 | 23.66 | 2 | + | + | + | + |
| / | 511.7312 | 19.81 | 2 | + | + | + | + |
| / | 512.2539 | 16.68 | 2 | + | + | + | + |
| / | 512.5736 | 19.63 | 3 | + | + | + | + |
| / | 512.7552 | 24.02 | 2 | + | + | + | + |

FIG. 13 (Continued)

| / | 513.7482 | 20.49 | 2 | + | + | + | + |
|---|---|---|---|---|---|---|---|
| / | 514.2510 | 13.59 | 2 | + | + | - | + |
| / | 515.2510 | 19.50 | 2 | + | + | + | + |
| / | 515.3429 | 10.06 | 1 | + | + | + | + |
| / | 517.6038 | 16.04 | 3 | + | + | - | + |
| / | 518.7344 | 19.81 | 2 | + | + | + | + |
| / | 520.7371 | 24.02 | 2 | + | + | + | + |
| / | 525.7364 | 25.65 | 2 | - | - | + | + |
| / | 526.2750 | 5.31 | 1 | + | + | + | + |
| / | 526.7177 | 19.81 | 2 | + | + | + | + |
| / | 527.2957 | 12.10 | 1 | + | + | + | + |
| / | 529.6020 | 19.40 | 3 | + | + | + | + |
| / | 530.7887 | 18.89 | 2 | + | + | + | + |
| / | 530.9570 | 19.63 | 3 | + | + | + | + |
| / | 531.2907 | 12.27 | 1 | + | + | + | + |
| / | 531.7855 | 12.78 | 2 | + | + | + | + |
| / | 534.1999 | 19.81 | 2 | + | + | + | + |
| / | 534.2432 | 6.30 | 1 | + | + | + | + |
| / | 535.2696 | 14.08 | 1 | + | + | + | + |
| / | 535.8036 | 17.75 | 2 | + | + | + | + |
| / | 538.2274 | 12.65 | 2 | + | + | + | + |

FIG. 13 (Continued)

| | | | | | | | |
|---|---|---|---|---|---|---|---|
| / | 538.2836 | 19.63 | 3 | + | + | + | + |
| / | 538.7866 | 17.27 | 2 | + | + | + | + |
| / | 539.7781 | 28.50 | 2 | + | + | + | + |
| / | 542.7990 | 14.46 | 2 | + | + | + | + |
| / | 543.6046 | 19.63 | 3 | + | + | + | + |
| / | 544.2973 | 12.40 | 1 | + | + | + | + |
| / | 544.3862 | 26.81 | 1 | + | + | + | + |
| / | 544.7864 | 16.68 | 2 | + | + | + | + |
| / | 544.7866 | 17.43 | 2 | + | + | + | + |
| / | 545.3081 | 14.46 | 2 | + | + | + | + |
| / | 546.7834 | 16.04 | 2 | + | + | + | + |
| / | 547.7753 | 27.08 | 2 | + | + | + | + |
| / | 548.9296 | 19.63 | 3 | + | + | + | + |
| / | 550.7959 | 14.24 | 2 | + | + | + | + |
| / | 552.6142 | 12.58 | 3 | + | + | + | + |
| / | 553.3052 | 13.59 | 2 | + | + | + | + |
| / | 553.7987 | 13.56 | 2 | + | + | + | + |
| / | 556.3212 | 12.55 | 1 | + | + | + | + |
| / | 556.7927 | 17.20 | 2 | + | + | + | + |
| / | 558.3128 | 5.59 | | + | + | + | + |
| / | 558.7653 | 27.09 | 2 | + | + | + | + |

FIG. 13 (Continued)

| | | | | | | | |
|---|---|---|---|---|---|---|---|
| / | 560.3174 | 13.31 | 1 | + | + | + | + |
| / | 561.3171 | 24.91 | 1 | + | + | + | + |
| / | 562.2794 | 12.78 | 1 | + | + | + | + |
| / | 563.8012 | 17.94 | 2 | + | + | + | + |
| / | 564.2834 | 15.75 | 1 | + | + | + | + |
| / | 564.2942 | 13.60 | 2 | + | + | + | + |
| / | 568.2868 | 6.30 | 1 | + | + | + | + |
| / | 569.6130 | 14.46 | 3 | + | + | + | + |
| / | 569.7932 | 10.06 | 2 | + | + | + | + |
| / | 570.3125 | 12.10 | 1 | + | + | + | + |
| / | 571.2687 | 13.00 | 1 | - | + | + | + |
| / | 571.2819 | 12.27 | 1 | + | + | + | + |
| / | 572.2779 | 13.60 | 2 | + | + | + | + |
| / | 572.3803 | 25.69 | 1 | + | + | + | + |
| / | 573.2504 | 14.46 | 2 | + | + | + | + |
| / | 573.2644 | 5.31 | 1 | + | + | + | + |
| / | 573.3398 | 23.14 | 1 | + | + | + | + |
| / | 574.2337 | 27.09 | 2 | + | + | + | + |
| / | 575.3018 | 14.46 | 2 | + | + | + | + |
| / | 578.2752 | 5.31 | 1 | + | + | + | + |
| / | 578.3000 | 12.27 | 2 | + | + | + | + |
| / | 578.3056 | 12.53 | 1 | + | + | + | + |

FIG. 13 (Continued)

| / | 579.7647 | 13.59 | 2 | + | + | + | + |
|---|----------|-------|---|---|---|---|---|
| / | 581.2635 | 19.63 | 2 | + | + | + | + |
| / | 581.3193 | 11.52 | 1 | + | + | + | + |
| / | 581.8293 | 17.50 | 2 | + | + | + | + |
| / | 583.6149 | 14.46 | 3 | + | + | - | + |
| / | 583.8135 | 12.10 | 2 | + | + | + | + |
| / | 584.3129 | 6.30  |   | + | + | + | + |
| / | 586.3359 | 16.42 | 1 | + | + | + | + |
| / | 587.1737 | 14.08 | 1 | + | + | + | + |
| / | 588.8368 | 16.04 | 2 | + | + | + | + |
| / | 589.2899 | 12.40 | 3 | + | + | - | + |
| / | 589.3338 | 15.44 | 1 | + | + | + | + |
| / | 594.2725 | 14.46 | 2 | + | + | + | + |
| / | 596.3298 | 12.10 | 1 | + | + | + | + |
| / | 596.8323 | 14.97 | 2 | + | + | + | + |
| / | 599.3923 | 22.27 | 1 | + | + | + | + |
| / | 600.2304 | 12.78 |   | + | + | + | + |
| / | 600.3867 | 20.13 | 1 | + | + | + | + |
| / | 601.3122 | 18.39 | 2 | + | + | + | + |
| / | 602.2936 | 14.24 | 1 | + | + | + | + |
| / | 602.3176 | 17.10 | 3 | + | + | - | + |

FIG. 13 (Continued)

| | | | | | | |
|---|---|---|---|---|---|---|
| / | 602.3390 | 8.27 | 1 | + | + | + | + |
| / | 603.2689 | 22.63 | 2 | + | + | + | + |
| / | 604.2905 | 12.35 | 1 | + | + | + | + |
| / | 604.3075 | 9.40 | 1 | + | + | + | + |
| / | 607.2546 | 15.50 | 1 | + | + | + | + |
| / | 607.2905 | 19.63 | 1 | + | + | + | + |
| / | 607.8255 | 14.80 | 2 | + | + | + | + |
| / | 608.3549 | 16.74 | 1 | + | + | + | + |
| / | 609.8244 | 17.75 | 2 | + | + | + | + |
| / | 618.3392 | 12.35 | 1 | + | + | + | + |
| / | 621.3747 | 21.95 | 1 | + | + | + | + |
| / | 624.3507 | 15.75 | 1 | + | + | + | + |
| / | 628.3564 | 12.10 | 2 | + | + | + | + |
| / | 629.8132 | 12.78 | 2 | + | + | + | + |
| / | 641.3310 | 23.36 | 2 | + | + | + | + |
| / | 643.3687 | 16.42 | 1 | + | + | + | + |
| / | 644.3510 | 10.06 | 1 | + | + | + | + |
| / | 646.7862 | 21.95 | 2 | + | + | + | + |
| / | 647.3307 | 17.75 | 1 | + | + | + | + |
| / | 648.3511 | 20.10 | 2 | + | + | + | + |
| / | 648.8497 | 23.36 | 2 | + | + | + | + |

FIG. 13 (Continued)

| | | | | | | | |
|---|---|---|---|---|---|---|---|
| / | 649.3000 | 19.82 | 1 | + | + | + | + |
| / | 649.3232 | 22.63 | 2 | + | + | + | + |
| / | 654.3328 | 17.94 | 2 | + | + | + | + |
| / | 655.3567 | 15.28 | 1 | + | + | - | + |
| / | 655.3930 | 13.03 | 1 | + | + | + | + |
| / | 656.8466 | 21.95 | 2 | + | + | + | + |
| / | 660.3497 | 15.00 | 2 | + | + | + | + |
| / | 662.3516 | 17.34 | 2 | + | + | + | + |
| / | 664.8443 | 20.70 | 2 | + | + | + | + |
| / | 666.8469 | 13.20 | 2 | + | + | + | + |
| / | 670.3497 | 15.50 | 2 | + | + | + | + |
| / | 670.4318 | 23.36 | 1 | + | + | + | + |
| / | 672.3542 | 18.90 | 2 | + | + | + | + |
| / | 672.8430 | 20.00 | 2 | + | + | + | + |
| / | 677.3781 | 10.98 | 1 | + | + | + | + |
| / | 683.8020 | 20.49 | 2 | + | + | + | + |
| / | 688.4038 | 20.13 | 1 | + | + | + | + |
| 3 | 693.8432 | 26.70 | 2 | - | - | - | + |
| / | 694.4061 | 11.52 | 1 | + | + | + | + |
| / | 703.3402 | 14.46 | 2 | + | + | + | + |
| / | 708.3562 | 18.89 | 2 | + | + | + | + |

FIG. 13 (Continued)

| | | | | | | | |
|---|---|---|---|---|---|---|---|
| / | 708.6879 | 14.08 | 3 | + | + | + | + |
| / | 710.8729 | 15.35 | 2 | + | + | + | + |
| 4 | 713.6902 | 17.79 | 3 | - | - | - | + |
| / | 718.2710 | 14.08 | 1 | + | + | + | + |
| / | 723.3107 | 13.49 | 1 | + | + | + | + |
| / | 724.3671 | 13.88 | 2 | + | + | - | + |
| / | 726.3114 | 20.13 | 2 | + | + | + | + |
| / | 726.3605 | 11.86 | 1 | + | + | + | + |
| / | 730.3692 | 16.42 | 2 | + | + | + | + |
| / | 731.8613 | 12.90 | 2 | + | + | - | + |
| / | 732.3417 | 17.04 | 1 | + | + | + | + |
| / | 745.3828 | 5.59 | | + | + | + | + |
| / | 745.8657 | 15.95 | 2 | + | + | - | + |
| / | 748.3914 | 12.40 | 1 | + | + | + | + |
| / | 749.0318 | 14.89 | 3 | + | + | + | + |
| / | 753.8639 | 14.89 | 2 | + | + | + | + |
| / | 755.7079 | 15.33 | 3 | + | + | + | + |
| / | 761.0394 | 14.46 | 3 | + | + | + | + |
| / | 762.3766 | 22.94 | 3 | - | + | - | + |
| / | 762.8742 | 13.03 | 2 | + | + | - | + |
| / | 766.7067 | 13.88 | 3 | + | + | + | + |

FIG. 13 (Continued)

| | | | | | | | |
|---|---|---|---|---|---|---|---|
| / | 771.3333 | 10.39 | 1 | + | + | + | + |
| / | 773.3523 | 12.10 | | + | + | + | + |
| 5 | 773.9237 | 18.51 | 2 | - | - | - | + |
| 6 | 774.9121 | 17.79 | 2 | - | - | - | + |
| / | 775.9012 | 16.04 | 2 | + | + | - | + |
| / | 778.3712 | 14.88 | 2 | + | + | + | + |
| / | 780.9306 | 20.10 | 2 | - | + | + | + |
| / | 781.9127 | 22.43 | 2 | + | + | + | + |
| / | 781.9374 | 21.52 | 2 | + | + | + | + |
| / | 783.4554 | 13.03 | 1 | + | + | + | + |
| / | 784.8969 | 20.13 | 2 | + | + | + | + |
| / | 785.8968 | 19.81 | 2 | + | + | + | + |
| / | 792.8801 | 18.34 | 2 | + | + | + | + |
| / | 793.8986 | 19.40 | 2 | + | + | + | + |
| / | 795.9306 | 19.61 | 2 | + | + | + | + |
| / | 798.9020 | 16.04 | 2 | + | + | - | + |
| / | 804.3942 | 18.11 | 2 | + | + | - | + |
| / | 804.8810 | 13.59 | 2 | + | + | + | + |
| / | 811.4610 | 12.30 | 1 | + | + | + | + |
| / | 811.4623 | 12.27 | 1 | + | + | + | + |
| / | 811.4634 | 12.10 | 1 | + | + | + | + |

FIG. 13 (Continued)

| / | 811.7179 | 18.34 | 3 | + | + | + | + |
|---|---|---|---|---|---|---|---|
| / | 813.4302 | 15.75 | 1 | + | + | + | + |
| / | 816.4244 | 16.24 | 2 | + | + | + | + |
| / | 821.3904 | 21.20 | 1 | + | + | + | + |
| / | 824.4354 | 19.63 | 2 | + | + | + | + |
| / | 834.7436 | 17.43 | 3 | + | + | + | + |
| / | 841.4766 | 20.13 | 1 | + | + | + | + |
| / | 845.4240 | 22.27 | 3 | + | + | + | + |
| / | 845.9125 | 15.33 | 2 | + | + | + | + |
| / | 849.7429 | 26.80 | 3 | - | + | - | + |
| / | 850.4249 | 21.02 | 3 | + | + | + | + |
| / | 852.4311 | 17.04 | 1 | + | + | + | + |
| / | 854.4121 | 14.46 | 2 | + | + | + | + |
| / | 868.4834 | 10.62 | 1 | + | + | + | + |
| / | 874.5250 | 31.78 | 1 | + | + | + | + |
| / | 874.7801 | 17.92 | 3 | + | + | + | + |
| / | 874.9170 | 14.46 | 2 | + | + | - | + |
| / | 883.4320 | 12.40 | 2 | + | + | - | + |
| / | 892.5215 | 14.62 | 1 | + | + | + | + |
| / | 898.5327 | 16.42 | 1 | + | + | + | + |
| / | 926.5504 | 23.66 | 1 | + | + | + | + |

FIG. 13 (Continued)

| / | 928.4948 | 12.27 | 1 | + | + | + | + |
|---|---|---|---|---|---|---|---|
| / | 934.4512 | 17.75 | 1 | + | + | + | + |
| / | 1014.4776 | 19.81 | 1 | + | + | + | + |
| / | 1018.5114 | 19.19 | 1 | + | + | + | + |
| / | 1021.5555 | 23.66 | | + | + | + | + |
| / | 1027.4908 | 13.59 | 1 | + | + | - | + |
| / | 1029.4871 | 19.50 | 1 | + | + | + | + |
| / | 1088.5613 | 17.34 | 1 | + | + | + | + |
| / | 1092.5548 | 16.04 | 1 | + | + | + | + |
| / | 1094.5447 | 27.08 | 1 | + | + | + | + |
| / | 1105.5997 | 13.59 | 1 | + | + | + | + |
| / | 1149.5944 | 14.46 | 1 | + | + | + | + |
| / | 1192.6607 | 15.00 | 1 | + | + | + | + |

FIG. 13 (Continued)

Table 5

|  | Marker ID | m/z | Retention time (min) | Charge | Donkey | Horse | Cattle | Pig |
|---|---|---|---|---|---|---|---|---|
| Donkey | DM1 | 518.2695±0.1 | 18.92 | 4 | + | - | - | - |
|  | DM2 | 675.6632±0.1 | 23.36 | 3 | + | - | - | - |
|  | DM3 | 761.3672±0.1 | 24.24 | 3 | + | - | - | - |
|  | DM4 | 766.6952±0.1 | 23.36 | 3 | + | - | - | - |
|  | DM5 | 774.0218±0.1 | 23.36 | 3 | + | - | - | - |
|  | DM6 | 784.3392±0.1 | 23.36 | 3 | + | - | - | - |
|  | DM7 | 854.0603±0.1 | 27.08 | 3 | + | - | - | - |
| Horse | HM1 | 386.2108±0.1 | 10.36 | 2 | - | + | - | - |
| Cattle | CM1 | 596.8454±0.1 | 18.90 | 2 | - | - | + | - |
|  | CM2 | 604.8556±0.1 | 17.84 | 2 | - | - | + | - |
|  | CM3 | 766.8957±0.1 | 18.34 | 2 | - | - | + | - |
| Pig | PM1 | 419.2446±0.1 | 14.04 | 2 | - | - | - | + |
|  | PM2 | 490.5942±0.1 | 14.40 | 3 | - | - | - | + |
|  | PM3 | 693.8432±0.1 | 26.70 | 2 | - | - | - | + |
|  | PM4 | 713.6902±0.1 | 17.79 | 3 | - | - | - | + |
|  | PM5 | 773.9237±0.1 | 18.51 | 2 | - | - | - | + |
|  | PM6 | 774.9121±0.2 | 17.79 | 2 | - | - | - | + |

FIG. 14

Table 6

| No. | m/z | RT (min) | Charge | Donkey | Horse | Cattle | Pig |
|---|---|---|---|---|---|---|---|
| 1 | 427.7377±0.1 | 10.96 | 2 | + | + | - | - |
| 2 | 434.7462±0.1 | 10.56 | 2 | + | + | - | - |
| 3 | 469.2702±0.1 | 13.12 | 2 | + | + | - | - |
| 4 | 492.5830±0.1 | 12.15 | 3 | + | + | - | - |
| 5 | 552.6176±0.1 | 12.69 | 3 | + | + | - | - |
| 6 | 746.8774±0.1 | 13.75 | 3 | + | + | - | - |

FIG. 15

Table 7

| Sample No. | The inventor method | | | | Standard method | | | |
|---|---|---|---|---|---|---|---|---|
| | Donkey | Horse | Cattle | Pig | Donkey | Horse | Cattle | Pig |
| 1 | + | - | - | - | + | - | - | - |
| 2 | + | - | - | - | + | - | - | - |
| 3 | + | - | - | - | + | - | - | - |
| 4 | + | - | - | - | + | - | - | - |
| 5 | + | - | - | - | + | - | - | - |
| 6 | + | - | - | - | + | - | - | - |
| 7 | + | - | - | - | + | - | - | - |
| 8 | + | - | - | - | + | - | - | - |
| 9 | + | - | - | - | + | - | - | - |
| 10 | + | - | - | - | + | - | - | - |
| 11 | + | - | - | - | + | - | - | - |
| 12 | + | - | - | - | + | - | - | - |
| 13 | + | - | - | - | + | - | - | - |
| 14 | + | - | - | - | + | - | - | - |
| 15 | + | - | - | - | + | - | - | - |
| 16 | + | - | - | - | + | - | - | - |
| 17 | + | - | - | - | + | - | - | - |
| 18 | + | - | - | - | + | - | - | - |
| 19 | + | - | - | - | + | - | - | - |
| 20 | + | - | - | - | + | - | - | - |

FIG. 16

| | | | | | | | | |
|---|---|---|---|---|---|---|---|---|
| 21 | + | - | - | - | + | - | - | - |
| 22 | + | - | - | - | + | - | - | - |
| 23 | + | - | - | - | + | - | - | - |
| 24 | + | - | - | - | + | - | - | - |
| 25 | + | - | - | - | + | - | - | - |
| 26 | + | - | - | - | + | - | - | - |
| 27 | + | - | - | - | + | - | - | - |
| 28 | + | - | - | - | + | - | - | - |
| 29 | + | - | - | - | + | - | - | - |
| 30 | + | - | - | - | + | - | - | - |
| 31 | + | - | - | - | + | - | - | - |
| 32 | + | - | - | - | + | - | - | - |
| 33 | + | - | - | - | + | - | - | - |
| 34 | + | - | - | - | + | - | - | - |
| 35 | + | - | - | - | + | - | - | - |
| 36 | + | - | - | - | + | - | - | - |
| 37 | + | - | - | - | + | - | - | - |
| 38 | + | - | - | - | + | - | - | - |
| 39 | + | - | - | - | + | - | - | - |
| 40 | + | - | - | - | + | - | - | - |
| 41 | + | - | - | - | + | - | - | - |

FIG. 16 (Continued)

| | | | | | | | | |
|---|---|---|---|---|---|---|---|---|
| 42 | + | - | - | - | + | - | - | - |
| 43 | + | - | - | - | + | - | - | - |
| 44 | + | - | - | - | + | - | - | - |
| 45 | + | - | - | - | + | - | - | - |
| 46 | + | - | - | - | + | - | - | - |
| 47 | + | - | - | - | + | - | - | - |
| 48 | + | - | - | - | + | - | - | - |
| 49 | + | - | - | - | + | - | - | - |
| 50 | + | - | - | - | + | - | - | - |
| 51 | + | - | - | - | + | - | - | - |
| 52 | + | - | - | - | + | - | - | - |
| 53 | + | - | - | - | + | - | - | - |
| 54 | + | + | - | - | + | + | - | - |
| 55 | + | + | - | - | - | + | - | - |
| 56 | - | + | - | - | - | + | - | - |
| 57 | - | + | - | - | - | + | - | - |
| 58 | - | + | - | - | - | + | - | - |
| 59 | - | + | - | - | - | + | - | - |
| 60 | - | + | - | - | - | + | - | - |
| 61 | - | + | - | + | - | + | - | + |
| 62 | - | + | - | + | - | + | - | + |

FIG. 16 (Continued)

|  |  |  |  |  |  |  |  |  |
|---|---|---|---|---|---|---|---|---|
| 63 | - | + | - | + | - | + | - | + |
| 64 | - | + | + | - | - | + | + | - |
| 65 | - | - | + | - | - | - | - | - |
| 66 | - | - | + | - | - | - | + | - |
| 67 | - | - | + | - | - | - | + | - |
| 68 | - | - | + | - | - | - | + | - |
| 69 | - | - | + | - | - | - | + | - |
| 70 | - | - | + | - | - | - | + | - |
| 71 | - | - | + | - | - | - | + | - |
| 72 | - | - | + | - | - | - | + | - |
| 73 | - | - | + | - | - | - | + | - |
| 74 | - | - | + | - | - | - | + | - |
| 75 | - | - | + | - | - | - | + | - |
| 76 | - | - | + | - | - | - | + | - |
| 77 | - | - | + | - | - | - | + | - |
| 78 | - | - | + | - | - | - | + | - |
| 79 | - | - | + | - | - | - | + | - |
| 80 | - | - | + | - | - | - | + | - |
| 81 | - | - | + | - | - | - | + | - |
| 82 | - | - | + | - | - | - | + | - |
| 83 | - | - | + | - | - | - | + | - |

FIG. 16 (Continued)

| | | | | | | | | |
|---|---|---|---|---|---|---|---|---|
| 84 | - | - | + | - | - | - | + | - |
| 85 | - | - | + | - | - | - | + | - |
| 86 | - | - | + | - | - | - | + | - |
| 87 | - | - | + | - | - | - | + | - |
| 88 | - | - | + | - | - | - | + | - |
| 89 | - | - | + | - | - | - | + | - |
| 90 | - | - | + | - | - | - | + | - |
| 91 | - | - | + | - | - | - | + | - |
| 92 | - | - | + | - | - | - | + | - |
| 93 | - | - | + | - | - | - | + | - |
| 94 | - | - | + | - | - | - | + | - |
| 95 | - | - | + | - | - | - | + | - |
| 96 | - | - | + | - | - | - | + | - |
| 97 | - | - | + | - | - | - | + | - |
| 98 | - | - | + | - | - | - | + | - |
| 99 | - | - | + | - | - | - | + | - |
| 100 | - | - | + | - | - | - | + | - |
| 101 | - | - | + | - | - | - | + | - |
| 102 | - | - | + | - | - | - | + | - |
| 103 | - | - | + | - | - | - | + | - |
| 104 | - | - | + | - | - | - | + | - |

FIG. 16 (Continued)

| | | | | | | | | |
|---|---|---|---|---|---|---|---|---|
| 105 | - | - | + | - | - | - | + | - |
| 106 | - | - | + | - | - | - | + | - |
| 107 | - | - | + | - | - | - | + | - |
| 108 | - | - | + | - | - | - | + | - |
| 109 | - | - | + | - | - | - | + | - |
| 110 | - | - | - | - | - | - | - | - |

FIG. 16 (Continued)

Table 8

| No. | m/z | Charge | Donkey | Horse | Cattle | Pig |
|---|---|---|---|---|---|---|
| 1 | 393.2 | 2 | + | + | + | - |
| 2 | 469.244 | 2 | + | + | - | - |
| 3 | 469.25 [a] | 2 | + | + | - | - |
| 4 | 523.2746 | 2 | + | + | + | + |
| 5 | 539.774 | 2 | + | + | - | - |
| 6 | 539.8 [a] | 2 | + | + | - | - |
| 7 | 570.2882 | 2 | + | + | + | + |
| 8 | 570.28915 | 2 | + | + | + | + |
| 9 | 618.35 [a] | 2 | + | + | - | - |
| 10 | 618.795 | 2 | + | + | - | - |
| 11 | 631.8045 | 2 | - | - | - | - |
| 12 | 649.3408 | 3 | + | + | - | - |
| 13 | 660.3151 | 2 | - | - | - | - |
| 14 | 661.5864 | 4 | - | - | - | - |
| 15 | 664.8349 | 2 | + | + | + | + |
| 16 | 680.3351 | 2 | - | - | - | - |
| 17 | 690.6957 | 3 | - | - | - | - |
| 18 | 724.8451 | 2 | - | - | - | - |
| 19 | 733.3581 | 2 | + | + | - | - |
| 20 | 751.3628 | 2 | - | - | - | - |
| 21 | 765.8 | 2 | - | - | - | - |
| 22 | 765.8556 | 2 | + | + | - | - |
| 23 | 765.867 | 2 | + | + | - | - |
| 24 | 765.9142 | 2 | + | + | - | - |

FIG. 17

| 25 | 766.4 | 2 | + | + | - | - |
| 26 | 767.7234[b] | 3 | - | - | - | - |
| 27 | 802.9325 | 2 | + | + | - | - |
| 28 | 806.1683 | 4 | - | - | - | - |
| 29 | 902.4576 | 2 | + | + | - | - |
| 30 | 910.4554 | 2 | - | - | - | - |
| 31 | 921.4649 | 2 | + | + | - | - |
| 32 | 1073.08 | 2 | - | - | - | - |

FIG. 17 (Continued)

Table 9

| Peptide Marker | Observed mass-charge ratio m/z | Retention time (min) |
| --- | --- | --- |
| DM1 | 518.2695±0.1 | 18.92 |
| DM2 | 675.6632±0.1 | 23.36 |
| DM3 | 761.3672±0.1 | 24.24 |
| DM4 | 766.6952±0.1 | 23.36 |
| DM5 | 774.0218±0.1 | 23.36 |
| DM6 | 784.3392±0.1 | 23.36 |
| DM7 | 854.0603±0.1 | 27.08 |

FIG. 18

Table 10

| Peptide Marker | Observed mass-charge ratio m/z | Retention time (min) |
| --- | --- | --- |
| HM1 | 386.2108±0.1 | 10.36 |

FIG. 19

Table 11

| Peptide Marker | Observed mass-charge ratio m/z | Retention time (min) |
|---|---|---|
| CM1 | 596.8454±0.1 | 18.90 |
| CM2 | 604.8556±0.1 | 17.84 |
| CM3 | 766.8957±0.1 | 18.34 |

FIG. 20

Table 12

| Peptide Marker | Observed mass-charge ratio m/z | Retention time (min) |
|---|---|---|
| PM1 | 419.2446±0.1 | 14.04 |
| PM2 | 490.5942±0.1 | 14.40 |
| PM3 | 693.8432±0.1 | 26.70 |
| PM4 | 713.6902±0.1 | 17.79 |
| PM5 | 773.9237±0.1 | 18.51 |
| PM6 | 774.9121±0.2 | 17.79 |

FIG. 21

PEPTIDE MARKERS FOR AUTHENTICATING EJIAO AND RELATED GELATINS

CROSS-REFERENCE TO RELATED APPLICATIONS

The present application claims priority to U.S. provisional patent application Ser. No. 63/061,165, filed on Aug. 4, 2020, and the disclosure of which is incorporated herein by reference in its entirety.

TECHNICAL FIELD

The present disclosure generally relates to peptide markers useful in the identification and/or authentication of animal hides, such as those from donkeys, horses, pigs, and cattle, and methods of use thereof.

BACKGROUND

Ejiao (Chinese materia medica: *Colla Corii Asini*) is a gelatin made from donkey (*Equus asinus*) hide. It is popularly used as a food health supplement in China. Ejiao exerts diverse beneficial effects, such as improving immune response, nourishing the blood, and delaying senescence. Ejiao market sales reached more than US$6 billion dollars in 2020 worldwide. However, because the demand is increasing faster than the supply, fake products, particularly gelatin made from cattle, pig, and horse hides, are frequently found in the market. Unlike Ejiao, which has been used by the Chinese for more than 2,000 years, the safety and efficacy of these fake products is unknown and therefore a matter of significant concern.

Differentiating fake Ejiao from authentic Ejiao is normally done on the basis of peptide markers. However, the currently used authentication peptide makers are not specific enough since they all were found by database-based proteomics. Problematically, many protein makers are shared by donkey (*Equus asinus*) and horse (*Equus caballus*). The myoglobin peptide HPGDFGADAQGAMTK (SEQ ID NO: 1) is considered as horse-specific in the Uniprot database; however, it also exists in donkey hide gelatin. The peptide GPPGAAGPPGPR (SEQ ID NO: 2) specified for authentication of Ejiao in the Chinese Pharmacopoeia is also found in horse hide gelatin. More importantly, many peptides are not recorded in any of these protein databases. For example, information on pig COL1A1 is lacking. As a result, there is no donkey-specific peptide marker. Reliable, specific peptide marker(s) for differentiating donkey hide gelatin from all others should be sought, perhaps in another way aside from proteomics.

There thus exists a need for an improved method for identifying Ejiao and related animal hide gelatins.

SUMMARY

Accordingly, it is an objective of the present disclosure to provide an improved method of identifying animal hide gelatins.

In a first aspect, provided herein is a method of identifying an animal hide gelatin in a sample suspected of comprising the animal hide gelatin, the method comprising: providing a hydrolysate of the sample; analyzing the hydrolysate of the sample using a mass spectroscopy method; determining whether the hydrolysate of the sample comprises one or more peptide markers, wherein the one or more peptide markers have an observed mass to charge ratio (m/z) selected from the group consisting of: 518.2695±0.1 (DM1), 675.6632±0.1 (DM2), 761.3672±0.1 (DM3), 766.6952±0.1 (DM4), 774.0218±0.1 (DM5), 784.3392±0.1 (DM6), 854.0603±0.1 (DM7), 386.2108±0.1 (HM1), 596.8454±0.1 (CM1), 604.8556±0.1 (CM2), 766.8957±0.1 (CM3), 419.2446±0.1 (PM1), 490.5942±0.1 (PM2), 693.8432±0.1 (PM3), 713.6902±0.1 (PM4), 773.9237±0.1 (PM5), and 774.9121±0.2 (PM6); and identifying based on the whether the hydrolysate of the sample comprises the one or more peptide markers if the sample comprises the animal hide gelatin, wherein the animal hide gelatin comprises donkey hide gelatin, horse hide gelatin, cattle hide gelatin, pig hide gelatin, or a mixture thereof.

In certain embodiments, the method further comprises hydrolyzing the sample thereby forming the hydrolysate of the sample.

In certain embodiments, the method further comprises hydrolyzing the sample using a protease thereby forming the hydrolysate of the sample.

In certain embodiments, the method further comprises hydrolyzing the sample using a protease selected from the group consisting of trypsin, chymotrypsin, lysine protease, aspartic protease, pepsin, papain, proteinase K, calpain, and subtilisin thereby forming the hydrolysate of the sample.

In certain embodiments, the method further comprises hydrolyzing the sample using trypsin thereby forming the hydrolysate of the sample.

In certain embodiments, the mass spectrometry method is tandem mass spectroscopy (MS/MS) and further comprises liquid chromatography.

In certain embodiments, the mass spectrometry method comprises high-performance liquid chromatography (HPLC-MS/MS) or ultra-performance liquid chromatography (UPLC-MS/MS).

In certain embodiments, the step of determining whether the hydrolysate of the sample comprises one or more peptide markers further comprises determining whether each of the one or more peptide markers has a predicted liquid chromatography retention time, wherein the predicted liquid chromatography retention time is determined by measuring the retention time of standard samples, wherein each of the standard samples comprises one of the one or more peptide markers.

In certain embodiments, the one or more peptide markers having an observed m/z are selected from the group consisting of DM1, DM2, DM3, DM4, DM5, DM6, and DM7.

In certain embodiments, the step of determining whether the hydrolysate of the sample comprises one or more peptide markers comprises determining whether the hydrolysate of the sample comprises 2 or more, 3 or more, 4 or more, 5 or more, 6 or more, or 7 peptide markers selected from the group consisting of DM1, DM2, DM3, DM4, DM5, DM6, and DM7.

In certain embodiments, the one or more peptide markers having an observed m/z comprises HM1.

In certain embodiments, the one or more peptide markers having an observed m/z are selected from the group consisting of CM1, CM2, and CM3.

In certain embodiments, the step of determining whether the hydrolysate of the sample comprises one or more peptide markers comprises determining whether the hydrolysate of the sample comprises 2 or more or 3 peptide markers selected from the group consisting of CM1, CM2, and CM3.

In certain embodiments, the one or more peptide markers having an observed m/z are selected from the group consisting of PM1, PM2, PM3, PM4, PM5, and PM6.

In certain embodiments, the step of determining whether the hydrolysate of the sample comprises one or more peptide markers comprises determining whether the hydrolysate of the sample comprises 2 or more, 3 or more, 4 or more, or 5 or more, or 6 peptide markers selected from the group consisting of PM1, PM2, PM3, PM4, PM5, and PM6.

In certain embodiments, the step of determining whether the hydrolysate of the sample comprises one or more peptide markers comprises determining whether the hydrolysate of the sample comprises one or more peptide markers selected from the group consisting of donkey peptide markers, a horse peptide marker, cattle peptide markers, and pig peptide markers, wherein the donkey peptide markers are selected from the group consisting of DM1, DM2, DM3, DM4, DM5, DM6, and DM7; the horse peptide marker is HM1; wherein the cattle peptide markers are selected from the group consisting of CM1, CM2, and CM3; and the pig peptide markers are selected from the group consisting of PM1, PM2, PM3, PM4, PM5, and PM6; and the step of identifying based on the whether the hydrolysate of the sample comprises the one or more peptide markers if the sample comprises the animal hide gelatin comprises determining whether the sample comprises donkey hide gelatin if the sample comprises one or more donkey peptide markers, determining whether the sample comprises horse hide gelatin if the sample comprises the horse hide peptide marker, determining whether the sample comprises cattle hide gelatin if the sample comprises one or more cattle peptide markers, or determining whether the sample comprises pig hide gelatin if the sample comprises one or more pig peptide markers.

In certain embodiments, the mass spectrometry method is MS/MS and further comprises an ultra-performance liquid chromatography method; and the step of determining whether the hydrolysate of the sample comprises one or more peptide markers further comprises determining whether each of the one or more peptide markers has a predicted ultra-performance liquid chromatography retention time, wherein the ultra-performance predicted liquid chromatography retention time is determined by measuring the retention time of standard samples, wherein each of the standard samples comprises one of the one or more peptide markers.

In certain embodiments, the one or more peptide markers having an observed m/z is selected from the group consisting of DM1, DM2, DM3, DM4, DM5, DM6, and DM7; and the step of identifying based on the whether the hydrolysate of the sample comprises the one or more peptide markers if the sample comprises the animal hide gelatin comprises determining whether the sample comprises donkey hide gelatin.

In certain embodiments, one or more peptide markers having an observed m/z are DM1, DM2, DM3, DM4, DM5, DM6, and DM7.

In certain embodiments, the method further comprises: hydrolyzing the sample using trypsin thereby forming the hydrolysate of the sample; the mass spectrometry method is MS/MS and further comprises ultra-performance liquid chromatography; and the step of determining whether the hydrolysate of the sample comprises one or more peptide markers further comprises determining whether each of the one or more peptide markers has a predicted ultra-performance liquid chromatography retention time, wherein the ultra-performance predicted liquid chromatography retention time is determined by measuring the retention time of standard samples, wherein each of the standard samples comprises one of the one or more peptide markers.

BRIEF DESCRIPTION OF THE DRAWINGS

The above and other objects and features of the present invention will become apparent from the following description of the invention, when taken in conjunction with the accompanying drawings, in which.

Figure 7:
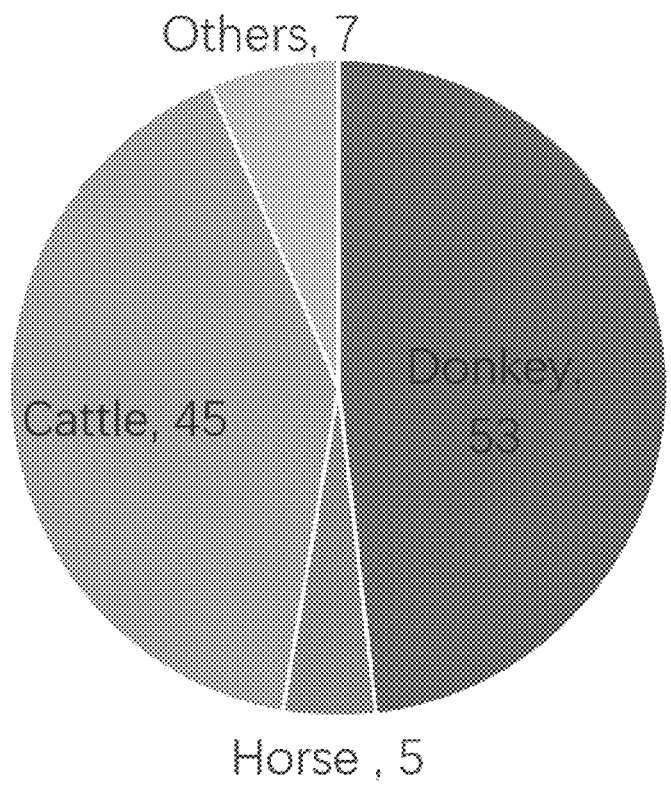

FIG. 7 shows the authentication results of 110 commercial Ejiao samples. Note: "Others" includes 3 pig/horse-gelatin, 2 donkey/horse-gelatin, 1 cattle/horse-gelatin and 1 fake product which did not contain any gelatins.

Figure 8:
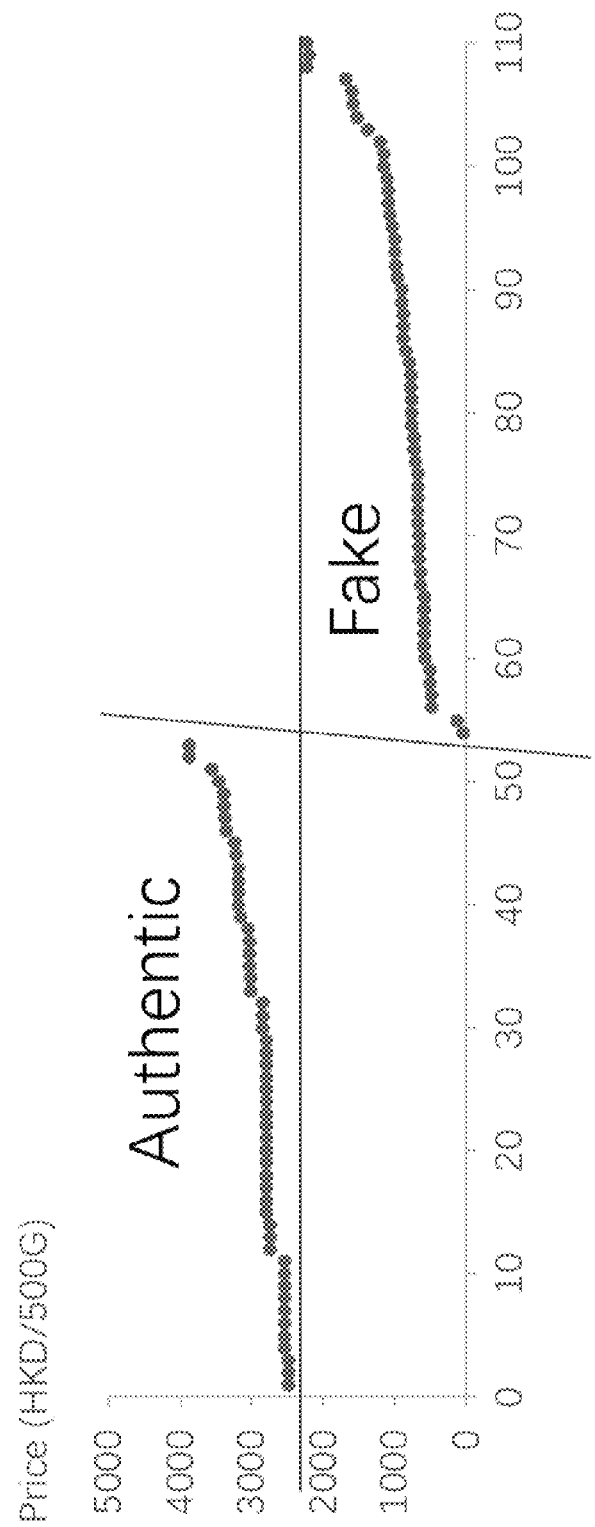

FIG. 8 shows the relationships between authenticity and price. Note: 53 samples on the upper left are authentic products, and 57 samples on the lower right are fake products.

Figure 9:
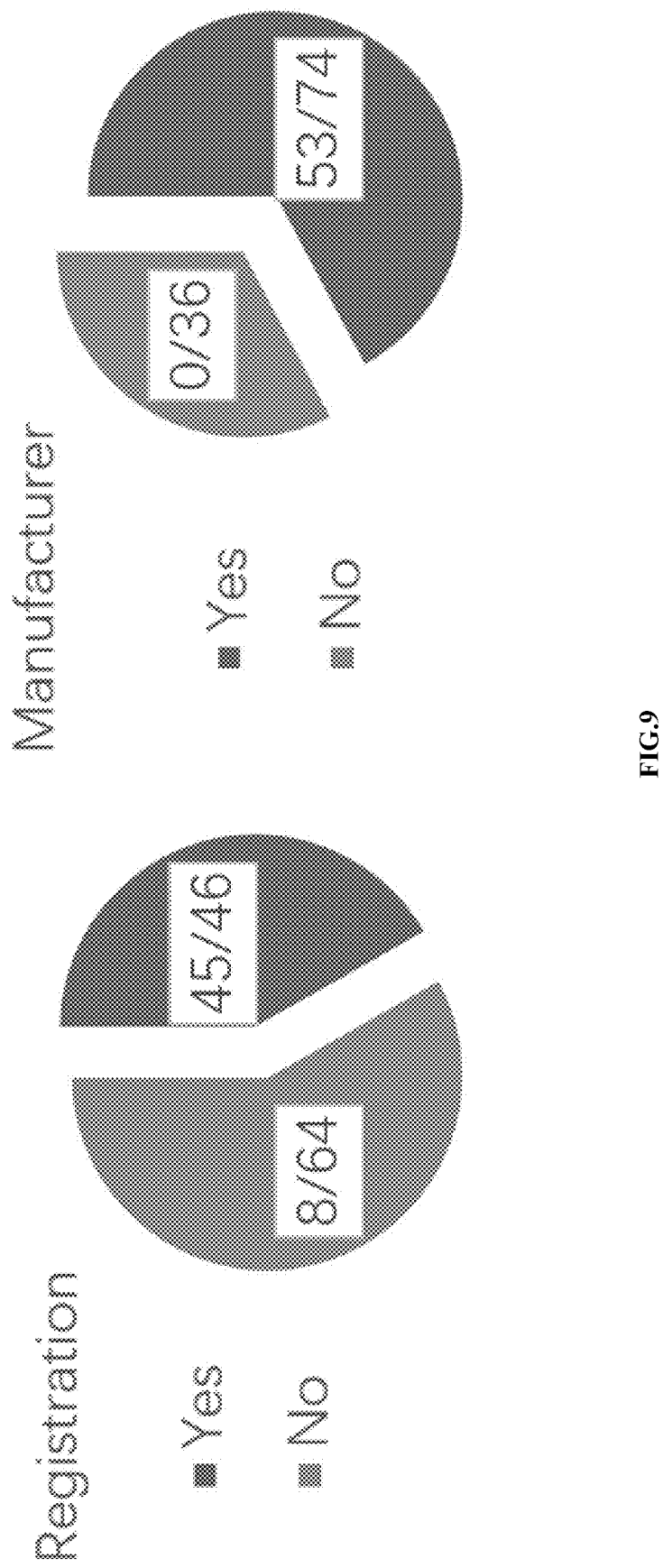

FIG. 9 shows the relationships between authenticity and registration (left) or manufacturers (right). Note: Registration represents having State Food and Drug Administration (SFDA) approval number.

FIG. 10 shows Table 1, which depicts peptide markers selection for donkey hide gelatin (Ejiao) from peptide fragments based on trypsin digestion followed by LC-Q-TOF-MS analysis. Notes: The number in the first column is the same as FIG. 1. Candidates, which are ions, were firstly screened from BPC of standard substance of donkey hide. Subsequently, they further confirmed by comparing EIC of four animal species. "+" indicates that the peptide marker candidate was detected by UPLC-Q-TOF-MS. "–" indicates that the peptide marker candidate was not detected. These peptide marker candidates showed two/three/four charges and were deduced to be peptides.

FIG. 11 shows Table 2, which depicts peptide markers selection for horse hide gelatin from peptide fragments based on trypsin digestion followed by LC-Q-TOF-MS analysis. Notes: Candidates were firstly screened from BPC of home-made horse hide gelatin. Subsequently, they further confirmed by comparing EIC of four animal species. "+" indicates that the peptide marker candidate was detected by UPLC-Q-TOF-MS. "–" indicates that the peptide marker candidate was not detected. These peptide marker candidates showed two/three/four charges and were deduced to be peptides.

FIG. 12 shows Table 3, which depicts peptide markers selection for cattle hide gelatin from peptide fragments based on trypsin digestion followed by LC-Q-TOF-MS analysis. Notes: Candidates were firstly screened from BPC of standard substance of cattle hide gelatin. Subsequently, they further confirmed by comparing EIC of four animal species. "+" indicates that the peptide marker candidate was detected by UPLC-Q-TOF-MS. "–" indicates that the peptide marker candidate was not detected. These peptide marker candidates showed two/three/four charges and were deduced to be peptides.

FIG. 13 shows Table 4, which depicts peptide markers selection for pig hide gelatin from peptide fragments based on trypsin digestion followed by LC-Q-TOF-MS analysis. Notes: Candidates were firstly screened from BPC of standard substance of pig hide gelatin. Subsequently, they further confirmed by comparing EIC of four animal species. "+" indicates that the peptide marker candidate was detected by UPLC-Q-TOF-MS. "–" indicates that the peptide marker candidate was not detected. These peptide marker candidates showed two/three/four charges and were deduced to be peptides.

FIG. 14 shows Table 5, which depicts authentication peptide markers found in the peptide fragments produced from trypsin-digestion of different animal skin gelatins by LC-Q-TOF-MS analysis. Notes: These peptide markers showed two/three/four charges and were deduced to be peptides. The mass accuracy is 0.1 Da, which means that the range of m/z to the peptide markers is ±0.1 Da.

FIG. 15 shows Table 6, which depicts donkey-specific peptide markers found by searching protein databases from peptide fragments based on trypsin digestion followed by LC-Q-TOF-MS analysis. Notes: After LC-Q-TOF-MS/MS analysis, the corresponding origin data were searched against *Bos taurus* (cattle), *Sus scrofa* (Pig) *Equus caballus* (horse) and *Equus asinus* (donkey) protein databases downloaded from UniProt KB (Jun. 29, 2020). By searching protein databases, peptides with 99% confidence, which means that 99 correct peptides and 1 incorrect, were selected. Then, by comparing these high-confidence peptides from four animal skins, donkey-specific peptide markers were screened, which are shown on the high-confidence peptide list of donkey skin, but not in that of horse, cattle or pig skin.

Figure 3:
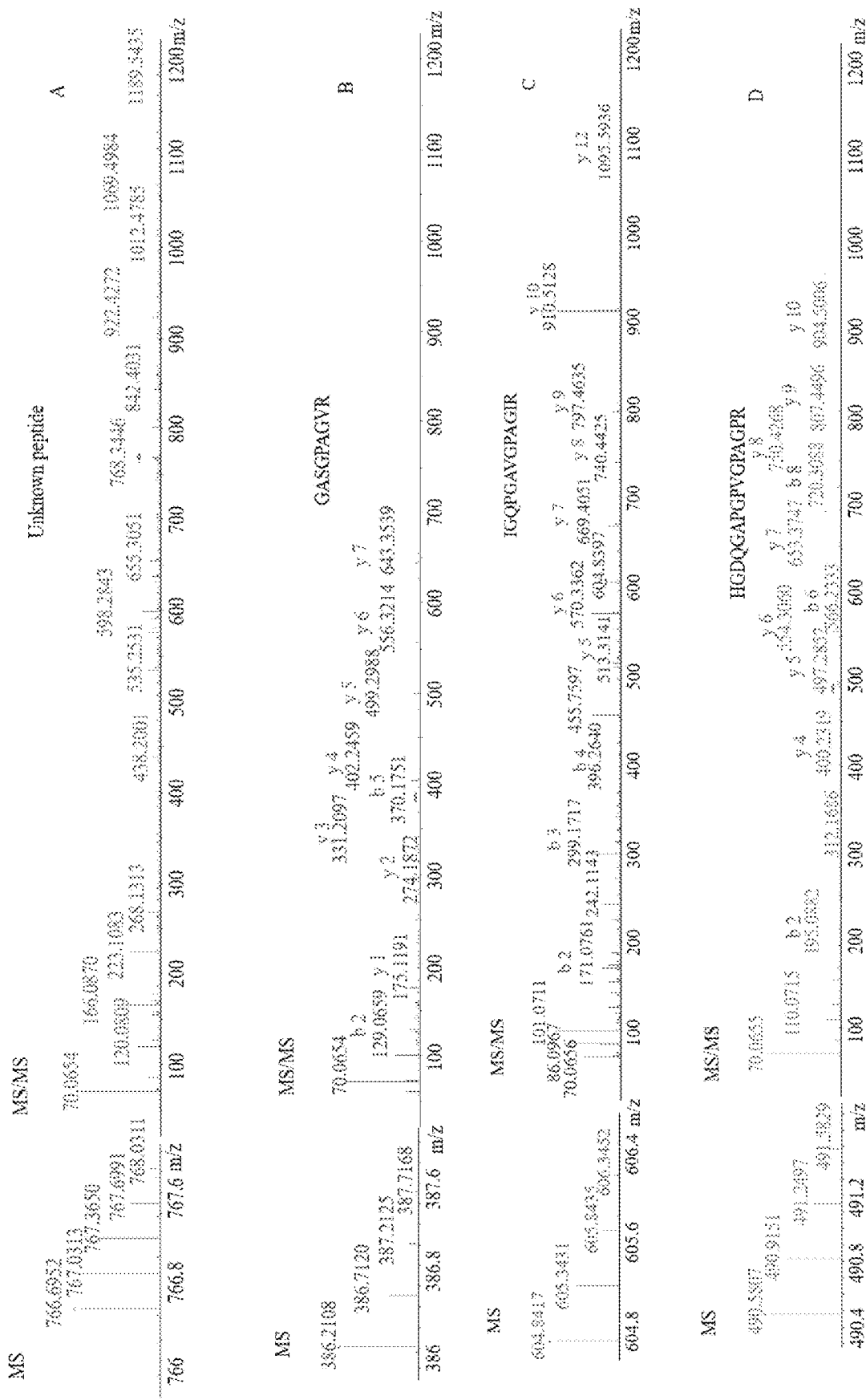
FIG. 3 shows MS and MS/MS spectra of one high-sensitivity peptide marker for each animal species including (A) DM4 (unknown peptide), (B) HM1 (peptide sequence: GASGPAGVR, SEQ ID NO: 3), (C) CM2 (peptide sequence: IGQPGAVGPAGIR, SEQ ID NO: 4) and (D) PM2 (peptide sequence: HGDQGAPGPVGPAGPR, SEQ ID NO: 5). (A) is donkey-specific peptide marker 4 (DM4), m/z 766.6952±0.1, 23.36 min; (B) is horse-specific peptide marker 1 (HM1), m/z 386.2108±0.1, 10.36 min; (C) is cattle-specific peptide marker 2 (CM2), m/z 604.8556±0.1, 17.84 min; (D) is pig-specific peptide marker 2 (PM2), m/z 490.5942±0.1, 14.40 min. Peptide sequences of (B)-(D) (SEQ ID NO: 3-5) are obtained by searching protein databases. By comparing with Skyline software, their matched b and y ions are indicated.
Figure 4:
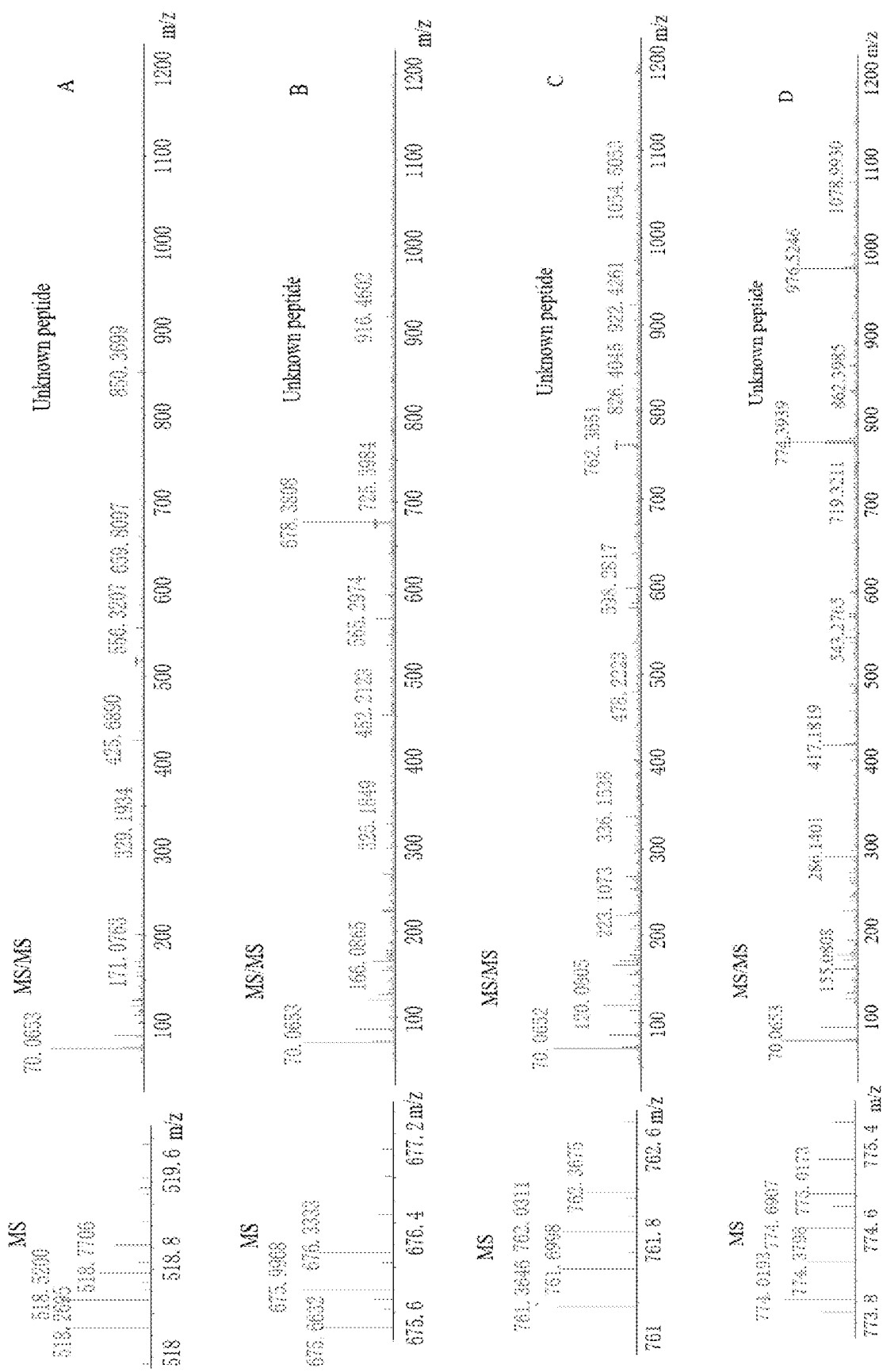
FIG. 4 shows (A) MS and MS/MS spectra of donkey-specific peptide marker 1. Note: DM1 is donkey-specific peptide marker 1, m/z 518.2695±0.1, 18.92 min (unknown peptide); (B) MS and MS/MS spectra of donkey-specific peptide marker 2. DM2 is donkey-specific peptide marker 2, m/z 675.6632±0.1, 23.36 min (unknown peptide); (C) MS and MS/MS spectra of donkey-specific peptide marker 3. DM3 is donkey-specific peptide marker 3, m/z 761.3672±0.1, 24.24 min (unknown peptide); (D) MS and MS/MS spectra of donkey-specific peptide marker 5. DM5 is donkey-specific peptide marker 5, m/z 774.0218±0.1, 23.36 min (unknown peptide); (E) MS and MS/MS spectra of donkey-specific peptide marker 6. DM6 is donkey-specific peptide marker 6, m/z 784.3392±0.1, 23.36 min (unknown peptide); (F) MS and MS/MS spectra of donkey-specific peptide marker 7 (unknown peptide). DM7 is donkey-specific peptide marker 7, m/z 854.0603±0.1, 27.08 min (unknown peptide).
Figure 4:
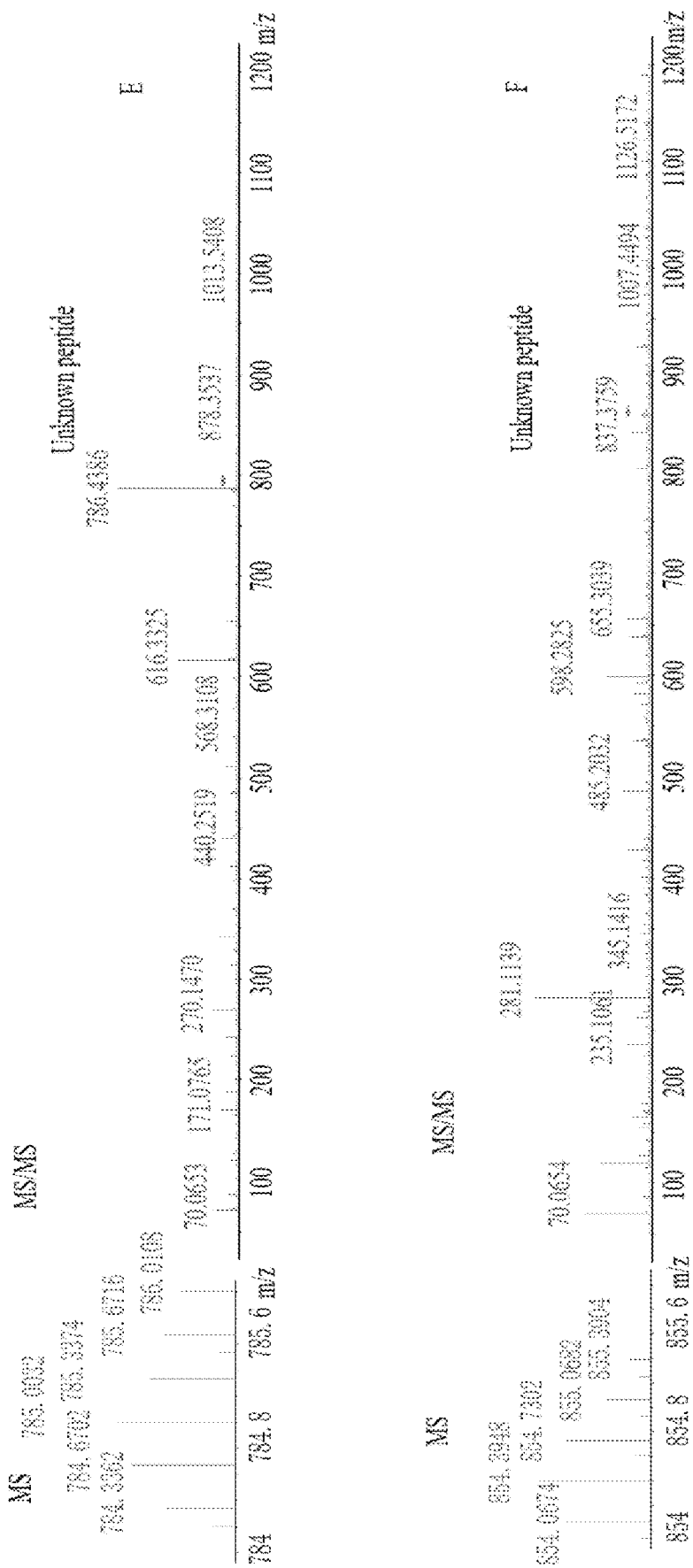
Figure 5:
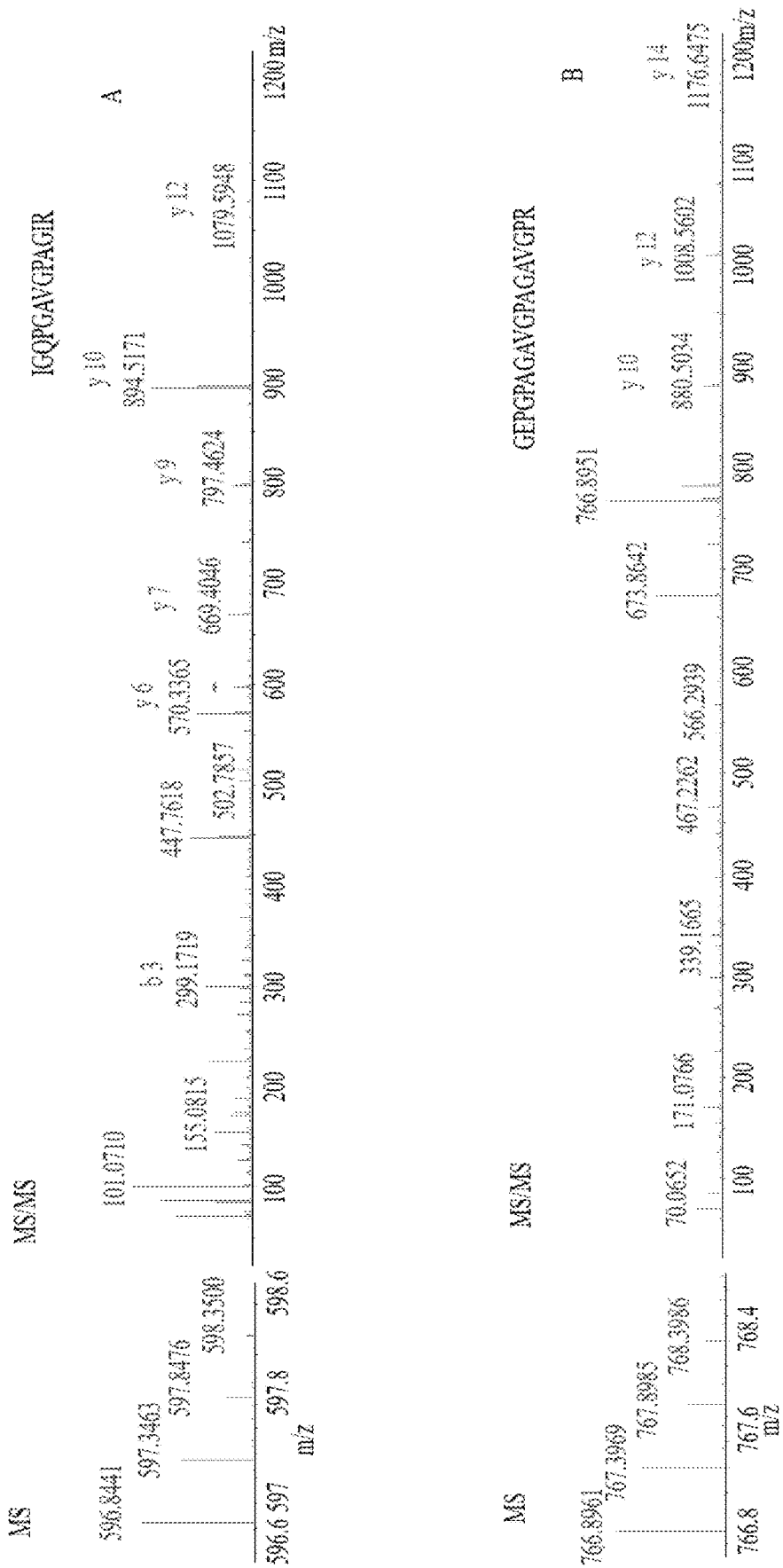
FIG. 5 shows (A) MS and MS/MS spectra of cattle-specific peptide marker 1. Note: CM1 is cattle-specific peptide marker 1, m/z 596.8454±0.1, 18.90 min (peptide sequence: IGQPGAVGPAGIR, SEQ ID NO: 4); (B) MS and MS/MS spectra of cattle-specific peptide marker 3. CM3 is cattle-specific peptide marker 3, m/z 766.8957±0.1, 18.34 min (peptide sequence: GEPGPAGAVGPAGAVGPR, SEQ ID NO: 6). Peptide sequences are obtained by searching protein databases. By comparing with Skyline software, their matched b and y ions are indicated.
Figure 6:
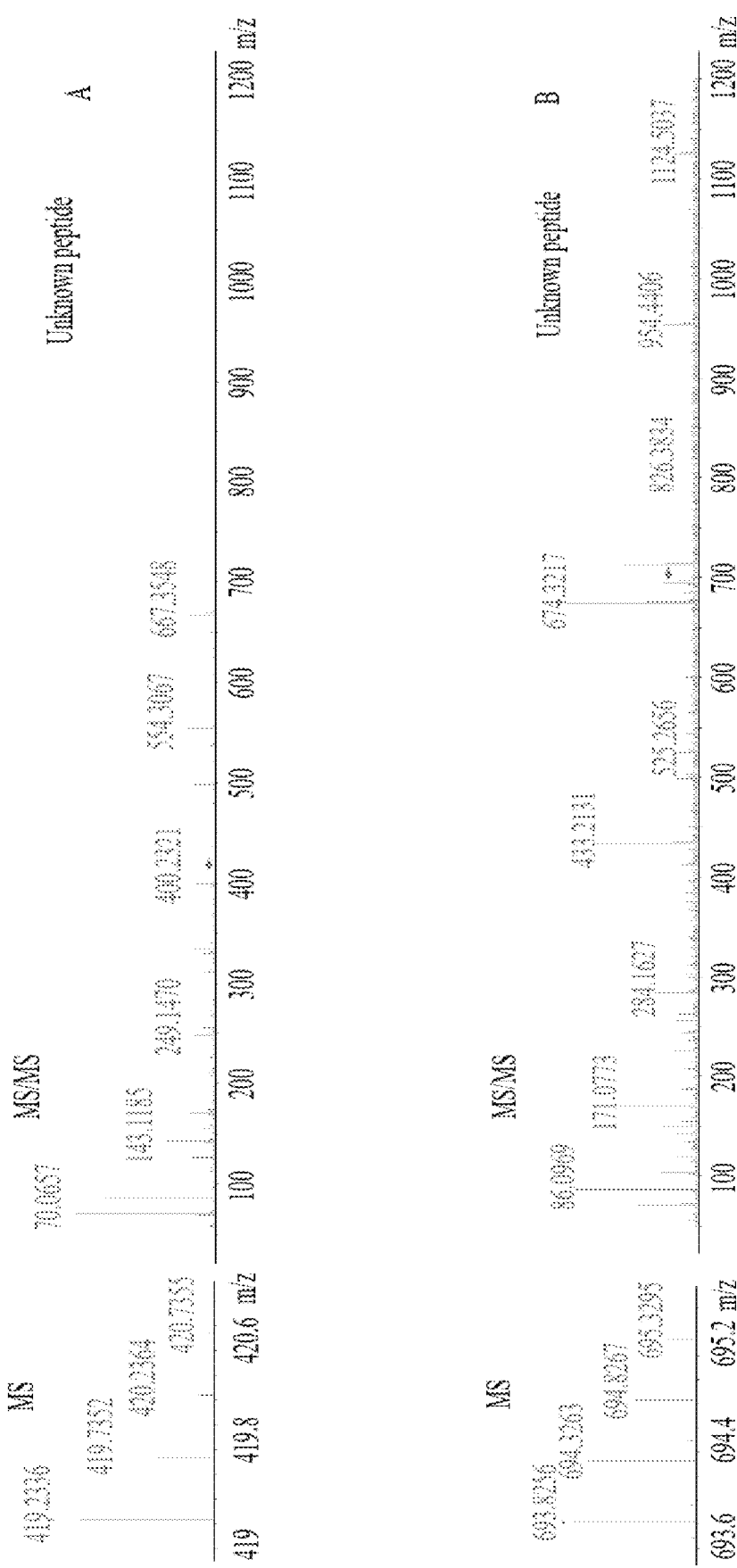
FIG. 6 shows (A) MS and MS/MS spectra of pig-specific peptide marker 1. Note: PM1 is pig-specific peptide marker 1, m/z 419.2446±0.1, 14.04 min (unknown peptide); (B) MS and MS/MS spectra of pig-specific peptide marker 3. PM3 is pig-specific peptide marker 3, m/z 693.8432±0.1, 26.7 min (unknown peptide); (C) MS and MS/MS spectra of pig-specific peptide marker 4. PM4 is pig-specific peptide marker 4, m/z 713.6902±0.1, 17.79 min (peptide sequence: GESGPAGPPGAPGAPGAPGPVGPAGK, SEQ ID NO: 7); (D) MS and MS/MS spectra of pig-specific peptide marker 5. PM5 is pig-specific peptide marker 5, m/z 773.9237±0.1, 18.51 min (peptide sequence: GETGPAGPAGPVGPVGAR, SEQ ID NO: 8); (E) MS and MS/MS spectra of and pig-specific peptide marker 6. PM6 is pig-specific peptide marker 6, m/z 774.9121±0.2, 17.79 min (peptide sequence: GEPGPAGSVGPAGAVGPR, SEQ ID NO: 6). Peptide sequences are obtained by searching protein databases. By comparing with Skyline software, their matched b and y ions are indicated.
Figure 6:
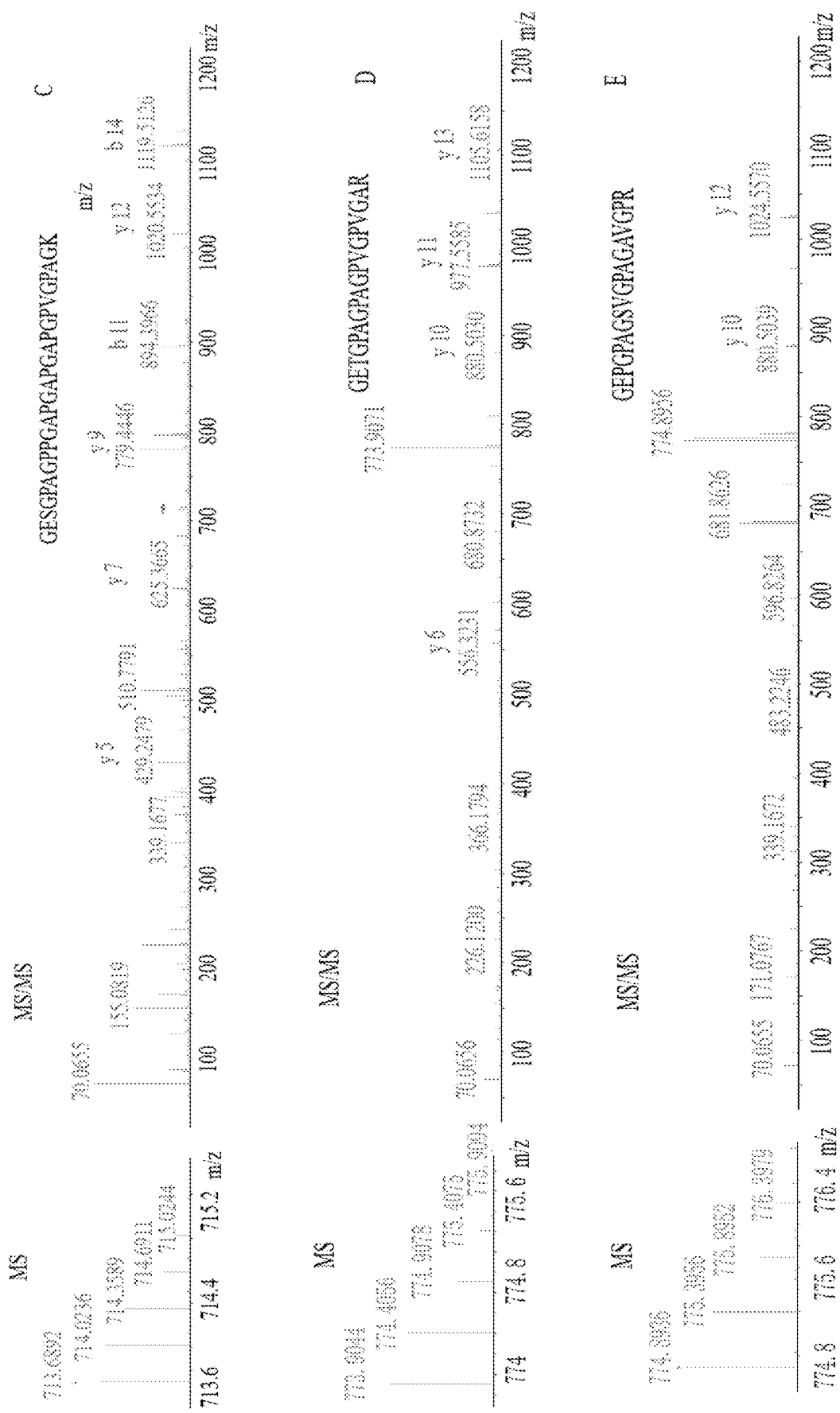
Figure 16:
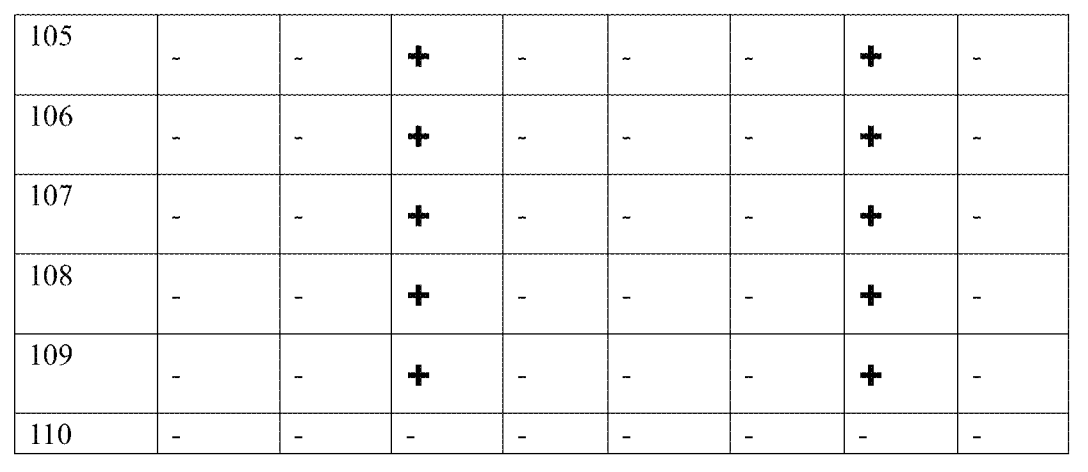

FIG. 16 shows Table 7, which depicts authentication results of commercial donkey hide gelatin samples in comparison with the standard method. Notes: The method is based on the corresponding high-sensitivity peptide markers. Owing to high intensity, four peptide markers from each species, as shown in FIG. 3, are used for specificity confirmation of various samples. "+" indicates that the peptide marker from the animal was detected by UPLC-Q-TOF-MS. "–" indicates that the specific peptide marker was not detected. Standard method is based on Chinese Pharmacopoeia. If the content is not more than 5%, it indicates that the peptide marker in the species was not detected.

FIG. 17 shows Table 8, which depicts specificity investigation of published peptide markers of donkey hide gelatin determined after trypsin digestion by LC-Q-TOF-MS analysis. Notes: "+" indicates that the peptide marker from the animal was detected by UPLC-Q-TOF-MS. "–" indicates that the specific peptide marker was not detected. The mass accuracy was set as 0.1 Da. To confirm a peptide marker was detected in an animal gelatin, it must satisfy the following criteria: 1) the specific peak was found; 2) the specific peak has a high intensity ($\geq 10^4$) "a" indicates that the peptide marker is from Chinese pharmacopeia (2020 edition). "b" indicates that the peptide marker (m/z 767.7234) has a low intensity in donkey hide gelatin ($10^3$). Besides, it failed to be distinguished from the isotope (m/z=767.6991, FIG. 3A) of the peptide marker (m/z=766.6952, DM4, FIG. 2) due to mass accuracy.

FIG. 18 shows Table 9, which depicts the observed m/z and retention time for donkey-specific peptide markers DM1, DM2, DM3, DM4, DM5, DM6, and DM7.

FIG. 19 shows Table 10, which depicts the observed m/z and retention time for horse-specific peptide marker HM1.

FIG. 20 shows Table 11, which depicts the observed m/z and retention time for cattle-specific peptide markers CM1, CM2, and CM3.

FIG. 21 shows Table 12, which depicts the observed m/z and retention time for pig-specific peptide markers PM1, PM2, PM3, PM4, PM5, and PM6.

DETAILED DESCRIPTION

Throughout the present disclosure, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the present invention.

Furthermore, throughout the present disclosure and claims, unless the context requires otherwise, the word "include" or variations such as "includes" or "including", will be understood to imply the inclusion of a stated integer or group of integers but not the exclusion of any other integer or group of integers.

The term "sample" as used herein relates to a material or mixture of materials, typically, although not necessarily, in fluid form, but can also be in solid form, suspected of containing or containing an animal hide gelatin derived from donkey hide, horse hide, pig hide, cattle hide, or a mixture thereof.

Provided herein is a method of method of identifying an animal hide gelatin in a sample suspected of comprising the animal hide gelatin, the method comprising: providing a hydrolysate of the sample; analyzing the hydrolysate of the sample using a mass spectroscopy method; determining whether the hydrolysate of the sample comprises one or more peptide markers, wherein the one or more peptide markers have an observed mass to charge ratio (m/z) selected from the group consisting of: 518.2695±0.1 (DM1), 675.6632±0.1 (DM2), 761.3672±0.1 (DM3), 766.6952±0.1 (DM4), 774.0218±0.1 (DM5), 784.3392±0.1 (DM6), 854.0603±0.1 (DM7), 386.2108±0.1 (HM1), 596.8454±0.1 (CM1), 604.8556±0.1 (CM2), 766.8957±0.1 (CM3), 419.2446±0.1 (PM1), 490.5942±0.1 (PM2), 693.8432±0.1 (PM3), 713.6902±0.1 (PM4), 773.9237±0.1 (PM5), and 774.9121±0.2 (PM6); and identifying based on the whether the hydrolysate of the sample comprises the one or more peptide markers if the sample comprises the animal hide gelatin, wherein the animal hide gelatin comprises donkey hide gelatin, horse hide gelatin, cattle hide gelatin, pig hide gelatin, or a mixture thereof.

The sample can be derived from a variety of sources, such as from processed or unprocessed animal hide gelatins, food stuffs, herbal medicine, and extracts thereof containing or suspected of containing animal hide gelatins derived from donkey hide, horse hide, pig hide, cattle hide, or a mixture thereof. In certain embodiments, the sample is derived from Ejiao.

The sample can optionally be treated before and/or after the hydrolysis step in order to, e.g., improve sample handling, sample properties and/or simplify mass spectroscopy analysis. The sample or the hydrolysate of the sample can be optionally treated by reduction, alkylation, and the like. Advantageously, however, the methods described herein do not require pre-treatment in order to achieve animal hide gelatin authentication with high specificity and sensitivity. Thus, in certain embodiments, the method described herein does not further comprise a pretreatment step.

The method can further comprise the step of hydrolysing the sample thereby forming the hydrolysate of the sample. Hydrolysis refers to the breakdown of proteins or polypeptides into shorter polypeptides, and oligopeptides and possibly, to some extent, individual amino acids by cleavage of one or more peptide bonds joining the constituent amino acids.

The method for hydrolysing the sample is not particularly limited. Any method for hydrolysing proteins or polypeptides known to those of ordinary skill in the art can be employed in the methods described herein. In certain embodiments, the hydrolysis of the sample is accomplished using a Brønsted acid, Brønsted base, or a Lewis acid catalysed aqueous hydrolysis or using an enzyme, such as a protease.

The protease can have broad specificity, so that all proteins and/or polypeptides in the sample are hydrolysed. Alternatively a mixture of specific or non-specific proteases may be used, to provide broader specificity.

In certain embodiments, the protease is selected from the group consisting of trypsin, chymotrypsin, lysine protease, aspartic protease, pepsin, papain, proteinase K, calpain, subtilisin, and mixtures thereof. In certain embodiments, the protease is trypsin.

The appropriate conditions for the hydrolysis of the sample will vary with the protease used. The optimal pH, temperature, and digestion time can be a function of the protease utilized for the hydrolysis of the sample and changing the protease will change these and potentially other parameters. The selection of the appropriate protease and the hydrolysis conditions is well within the skill of a person of ordinary skill in the art.

The hydrolysate of the sample can comprise a mixture of intact proteins or polypeptides, shorter polypeptides, and oligopeptides and component amino acids, which are produced by hydrolysis. Such mixture can be analysed using a mass spectrometry method to determine whether the sample comprises one or more peptide markers useful for identifying the animal hide gelatin in the sample.

Mass spectrometry is performed using a mass spectrometer comprising an ion source for ionizing the hydrolysate of the sample and creating charged molecules and/or charged fragments for further analysis. The ionization of the hydrolysate of the sample can be performed by electron ionization, chemical ionization, electrospray ionization (ESI), photon ionization, atmospheric pressure chemical ionization (APCI), photoionization, atmospheric pressure photoionization (APPI), fast atom bombardment (FAB), liquid secondary ionization (LSI), matrix assisted laser desorption ionization (MALDI), field ionization, field desorption, thermospray/plasmaspray ionization, surface enhanced laser desorption ionization (SELDI), inductively coupled plasma (ICP) and particle beam ionization. A person of ordinary skill in the art will understand that the choice of ionization method can be determined based on the properties of the analyte(s) being measured, type of sample, detector type, the choice of positive versus negative mode, etc. The ionizer can operate in positive or negative ion mode. In certain embodiments, the ionization of the sample is accomplished using ESI.

Once the hydrolysate of the sample has been ionized, the positively charged or negatively charged ions thereby created may be analysed to determine an m/z ratio. Exemplary analysers for determining m/z ratios include, but are not limited to, quadrupole analysers, ion traps analysers, and time-of-flight (TOF) analysers. In certain embodiments, the analyser is a tandem mass spectrometers (MS) selected from a triple quadrupole MS and 2 dual-focusing; and hybrid MS selected from the group consisting of quadrupole TOF (Q-TOF), ion trap TOF (IT-TOF), quadrupole ion trap (Q-IT), quadrupole-cyclotron-resonance (Q-ICR), ion trap ion-cyclotron-resonance (IT-ICR), ion trap orbitrap (IT-orbitrap), 2 TOF (TOF-TOF), and multistage MS ($MS^n$). The ions may be detected using several detection modes. For example, selected ions may be detected, i.e. using a selective ion monitoring mode (SIM), or alternatively, ions may be detected using a scanning mode, e.g., multiple reaction monitoring (MRM) or selected reaction monitoring (SRM). In certain embodiments, the m/z ratio is determined using a Q-TOF analyser.

In certain embodiments, the mass spectrometry method further comprises liquid chromatograph prior to the step of analysing the hydrolysate of the sample by mass spectrometry. Liquid chromatography is a process of selective at least partial obstruction of one or more components of a fluid solution (mobile phase) as the mobile phase passes through a column of a substance, through capillary passageways, or through a single contiguous column of solid support, such as monolithic column. The at least partial obstruction results from the distribution of the components of the mixture between the stationary phase and mobile phase, as this mobile phase moves relative to the stationary phase(s). Examples of liquid chromatography include, but are not limited to, HPLC, UPLC [also known as ultrahigh performance liquid chromatograph (UHPLC)], and reverse phase liquid chromatography (RPLC). In certain embodiments, the mass spectrometry method further comprises HPLC or UPLC, such as HPLC-MS, UPLC-MS, HPLC-MS/MS or UPLC-MS/MS. In the examples below the mass spectrometry method comprises reverse phase UPLC-ESI-qTOF-MS/MS using a C18 column.

The m/z data generated as a result of the mass spectrometry analysis of the hydrolysate sample can be then be examined to determine whether the hydrolysate of the sample comprises ions that correspond with one or more peptide markers having an observed m/z that are useful for identifying animal hide gelatins derived from donkey hide gelatin, horse hide gelatin, cattle hide gelatin, pig hide gelatin, or a mixture thereof. In certain embodiments, the one or more peptide markers have an observed m/z selected from the group consisting of DM1, DM2, DM3, DM4, DM5, DM6, DM7, HM1, CM1, CM2, CM3, PM1, PM2, PM3, PM4, PM5, and PM6.

In certain embodiments, the step of determining whether the hydrolysate comprises one or more peptide markers comprises determining whether the hydrolysate comprises 2 or more peptide markers, 3 or more peptide markers, 4 or more peptide markers, 5 or more peptide markers, 6 or more peptide markers, 7 or more peptide markers, 8 or more peptide markers, 9 or more peptide markers, 10 or more peptide markers, 11 or more peptide markers, 12 or more peptide markers, 13 or more peptide markers, 14 or more peptide markers, 15 or more peptide markers, 16 or more peptide markers, or 17 peptide markers.

In certain embodiments, the method is used to identify a sample containing or suspected of containing donkey hide gelatin, wherein the step of determining whether the hydrolysate of the sample comprises one or more peptide markers comprises whether the hydrolysate of the sample comprises 1 or more peptide markers, 2 or more peptide markers, 3 or more peptide markers, 4 or more peptide markers, 5 or more peptide markers, 6 or more peptide markers, or 7 peptide markers having an observed m/z selected from the group consisting of DM1, DM2, DM3, DM4, DM5, DM6, and DM7.

In certain embodiments, the method is used to identify a sample containing or suspected of containing horse hide gelatin, wherein the step of determining whether the hydrolysate of the sample comprises one or more peptide markers comprises whether the hydrolysate of the sample comprises a peptide marker have an observed m/z of HM1.

In certain embodiments, the method is used to identify a sample containing or suspected of containing cattle hide gelatin, wherein the step of determining whether the hydrolysate of the sample comprises one or more peptide markers comprises whether the hydrolysate of the sample comprises 1 or more peptide markers, 2 or more peptide markers, or 3 peptide markers having an observed m/z selected from the group consisting of CM1, CM2, and CM3.

In certain embodiments, the method is used to identify a sample containing or suspected of containing pig hide gelatin, wherein the step of determining whether the hydrolysate of the sample comprises one or more peptide markers comprises whether the hydrolysate of the sample comprises 1 or more peptide markers, 2 or more peptide markers, 3 or more peptide markers, 4 or more peptide markers, 5 or more peptide markers, or 6 peptide markers having an observed m/z selected from the group consisting of PM1, PM2, PM3, PM4, PM5, and PM6.

The methods described herein can be used to determine if a sample suspected of comprising donkey hide gelatin comprises one or more adulterants selected from the group consisting of horse hide gelatin, cattle hide gelatin, pig hide gelatin, and mixtures thereof. The step of identifying whether the sample contains an animal hide gelatin may comprise also authenticating that a specific type of animal hide gelatin and/or distinguishing between different types of animal hide gelatins. The step of identifying whether the sample contains an animal hide gelatin may further comprise determining the value of the animal hide gelatin based on the identity of the animal hide gelatin and taking in to consideration the market rate of the identified animal hide gelatin and its purity.

Figure 2:
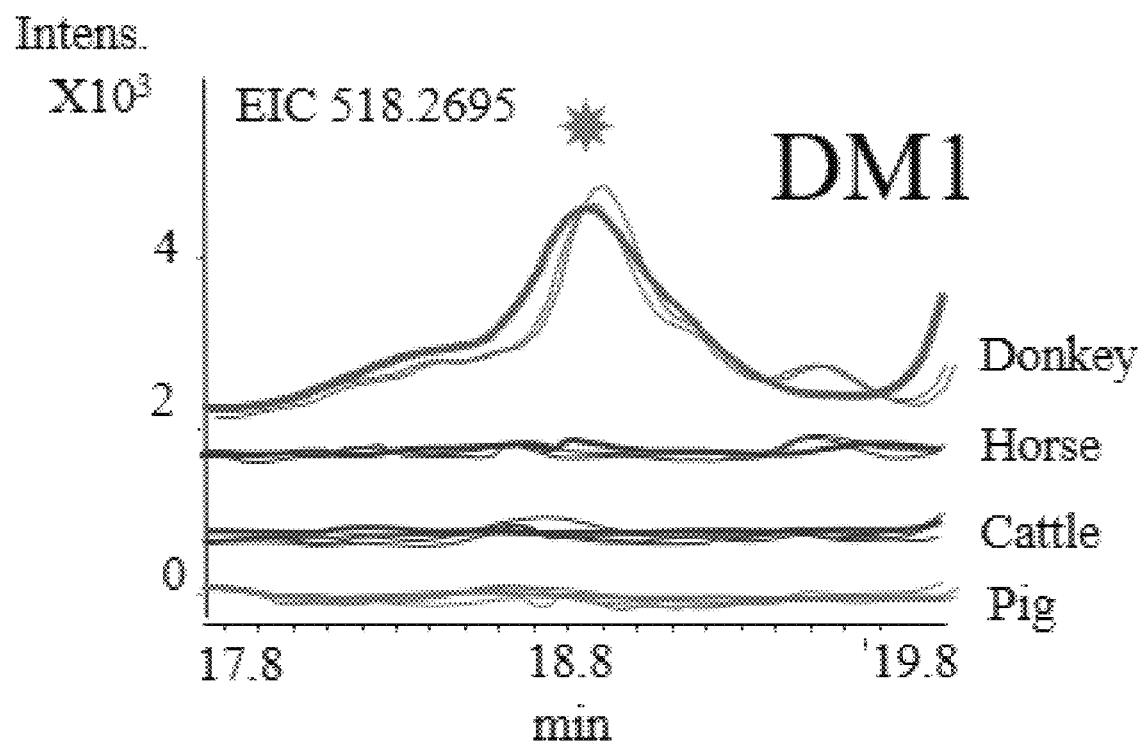
FIG. 2 shows extracted ion chromatograms of specific peptide markers for donkey (DM1-DM7, HM1-HM4, CM1-CM3, and PM1-PM6) Note: The mass accuracy is 0.1 Da, which means that the range of m/z to the peptide markers is ±0.1 Da. DM is short for donkey-specific peptide marker; HM is short for horse-specific peptide marker; CM is short for cattle-specific peptide marker, and PM is short for pig-specific peptide marker.
Figure 2:
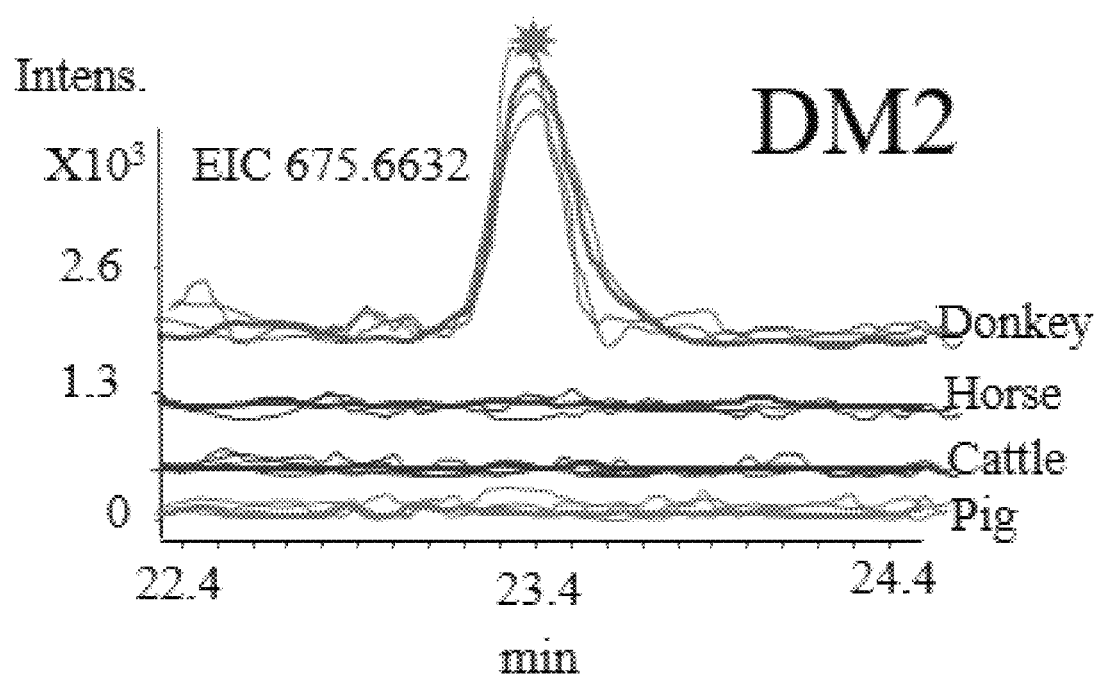
Figure 2:
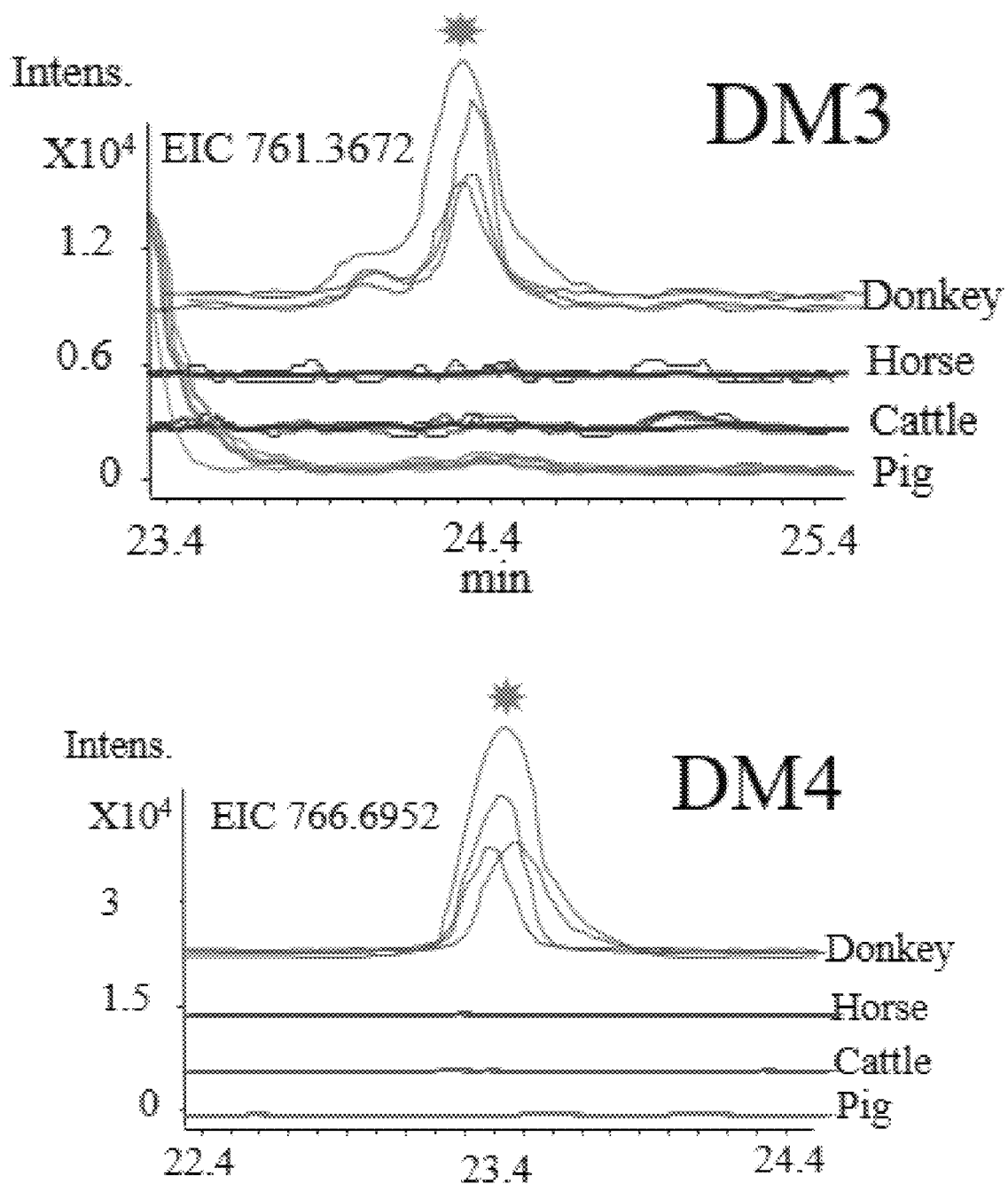
Figure 2:
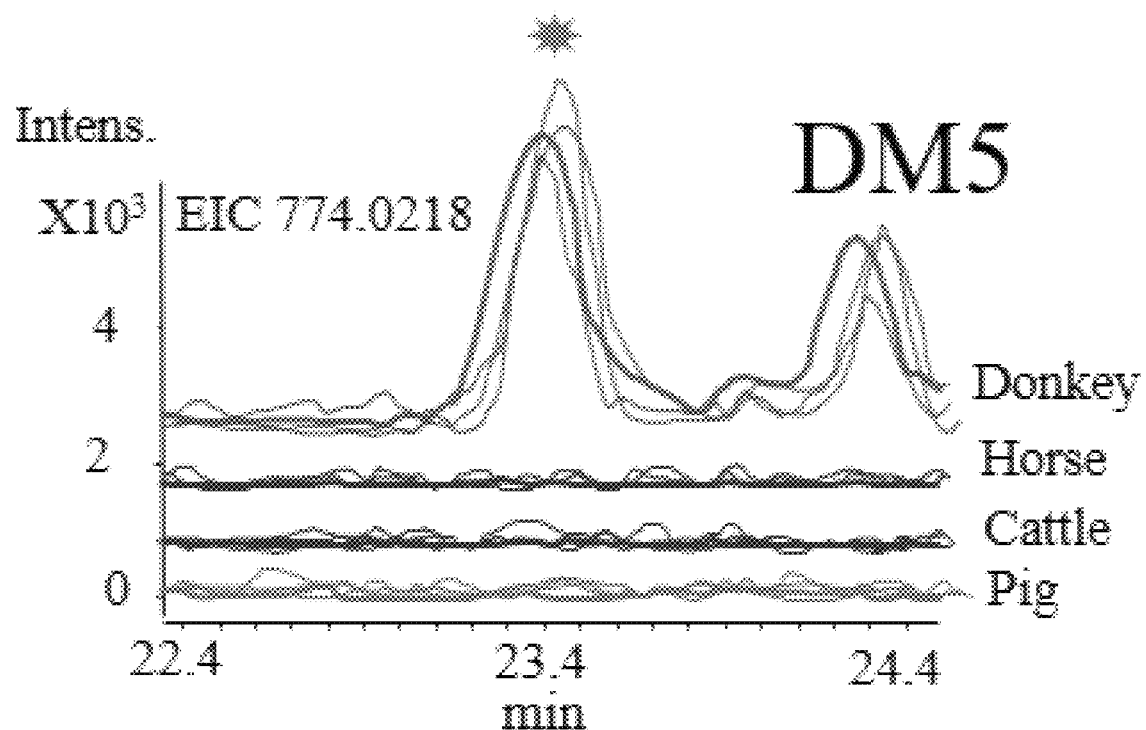
Figure 2:
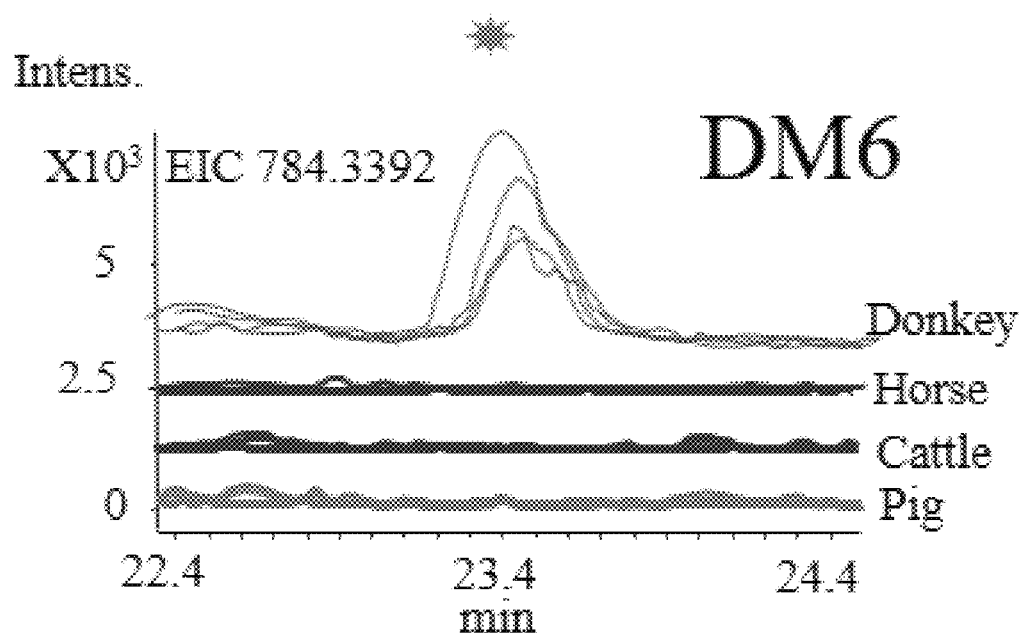
Figure 2:
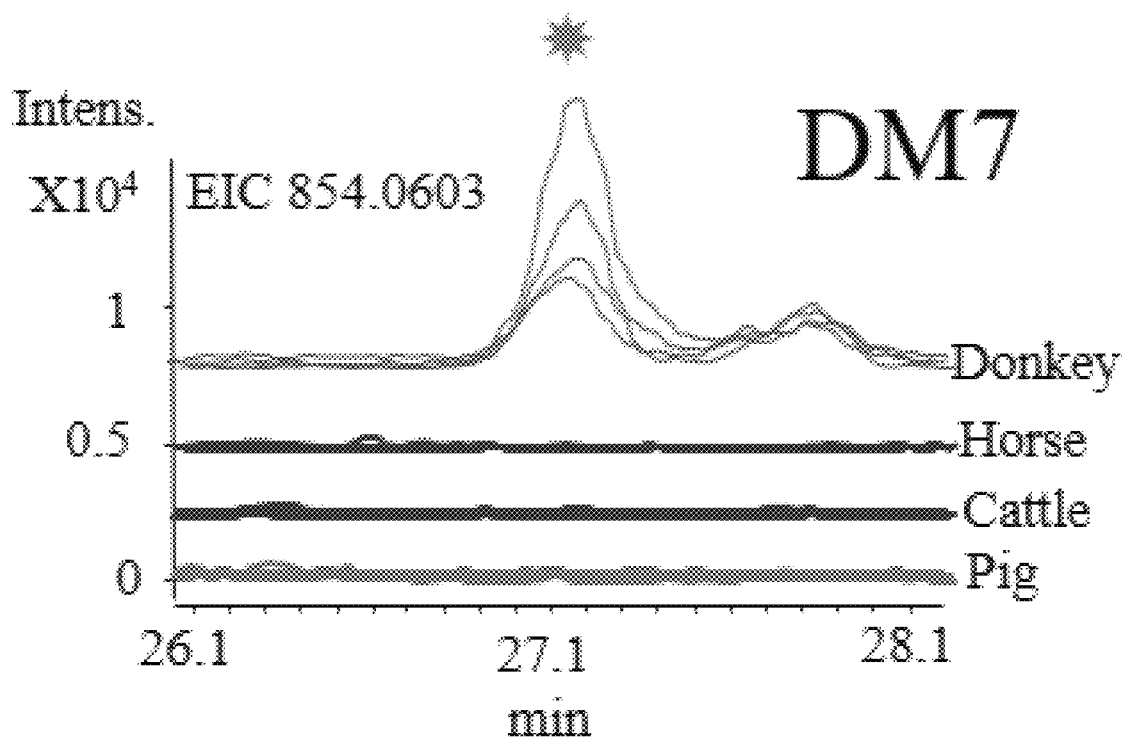
Figure 2:
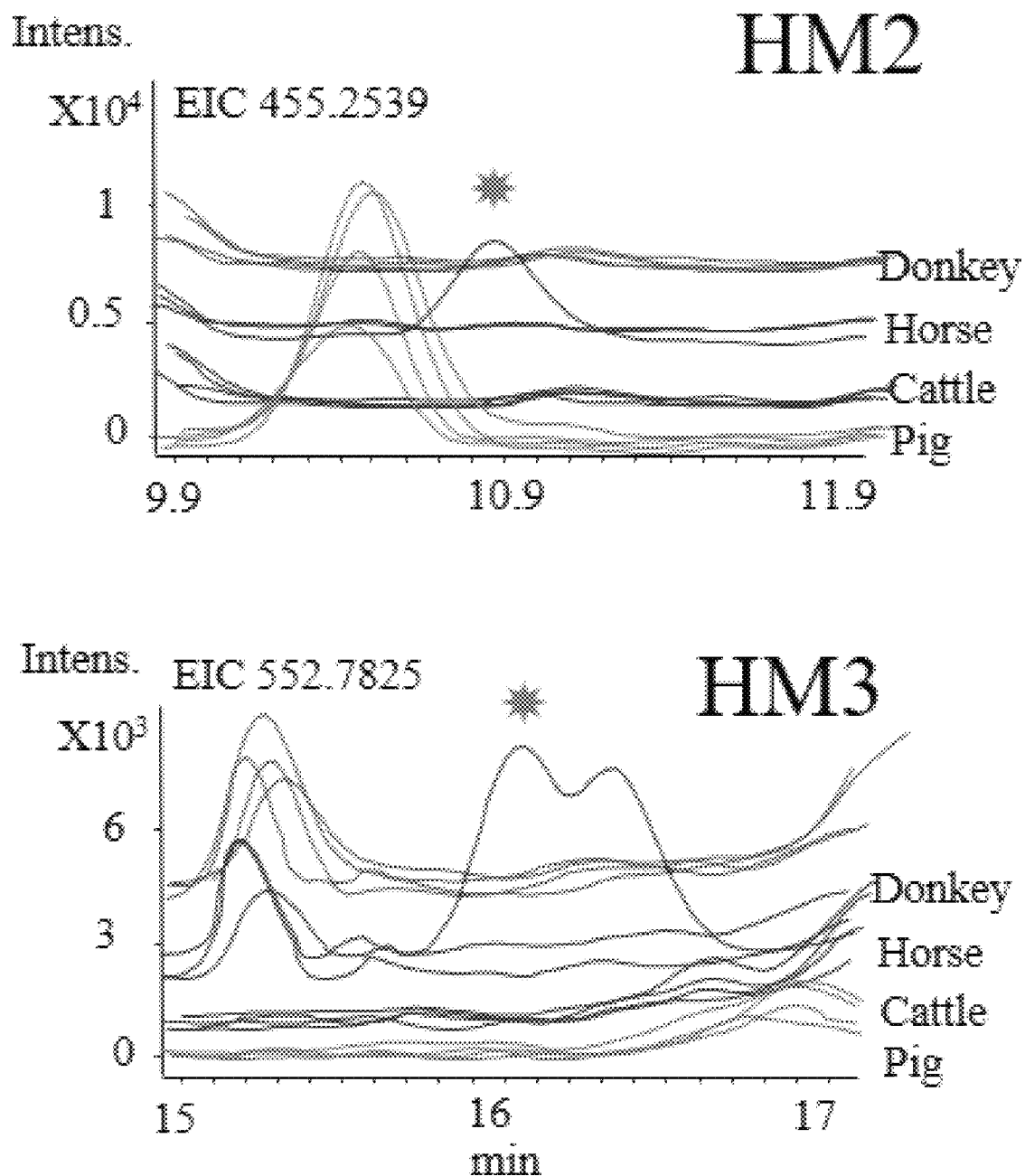
Figure 2:
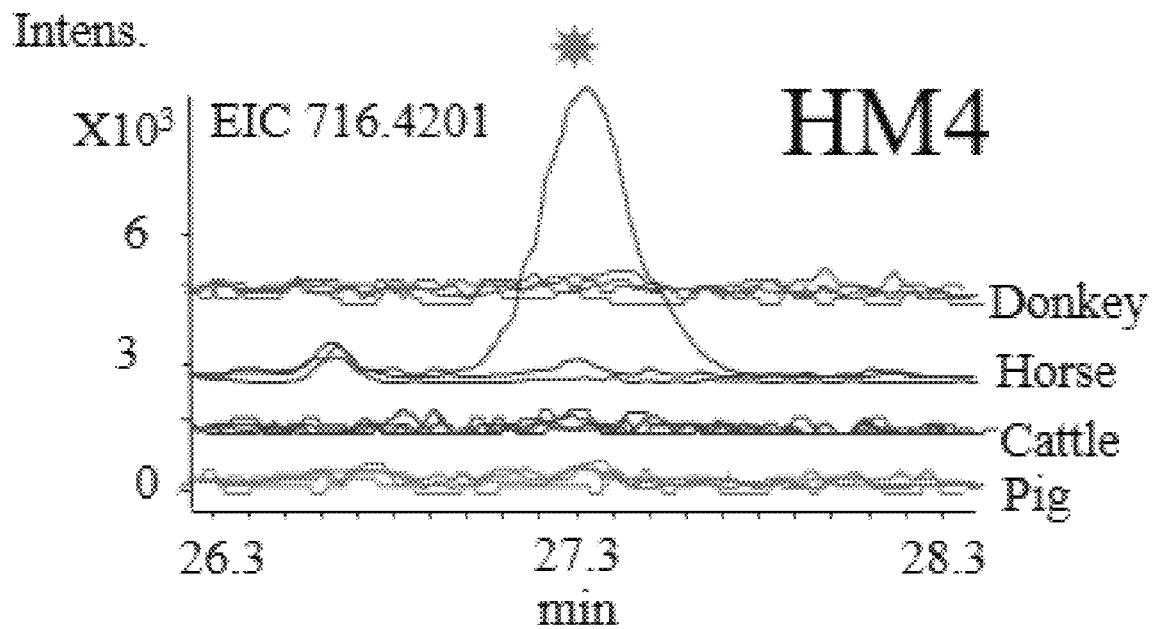
Figure 2:
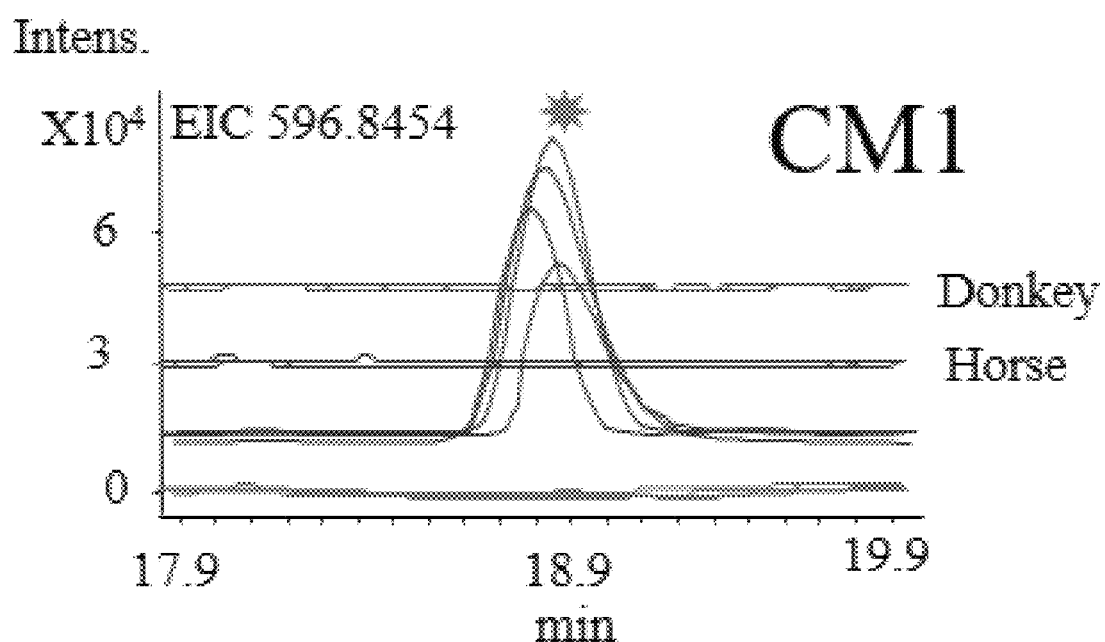
Figure 2:
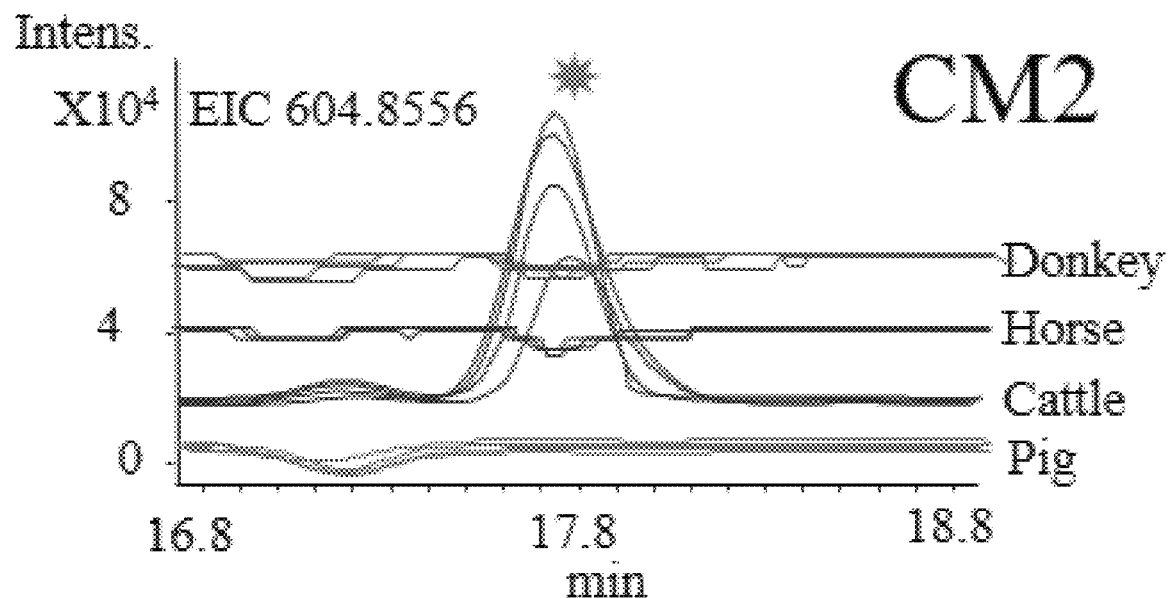
Figure 2:
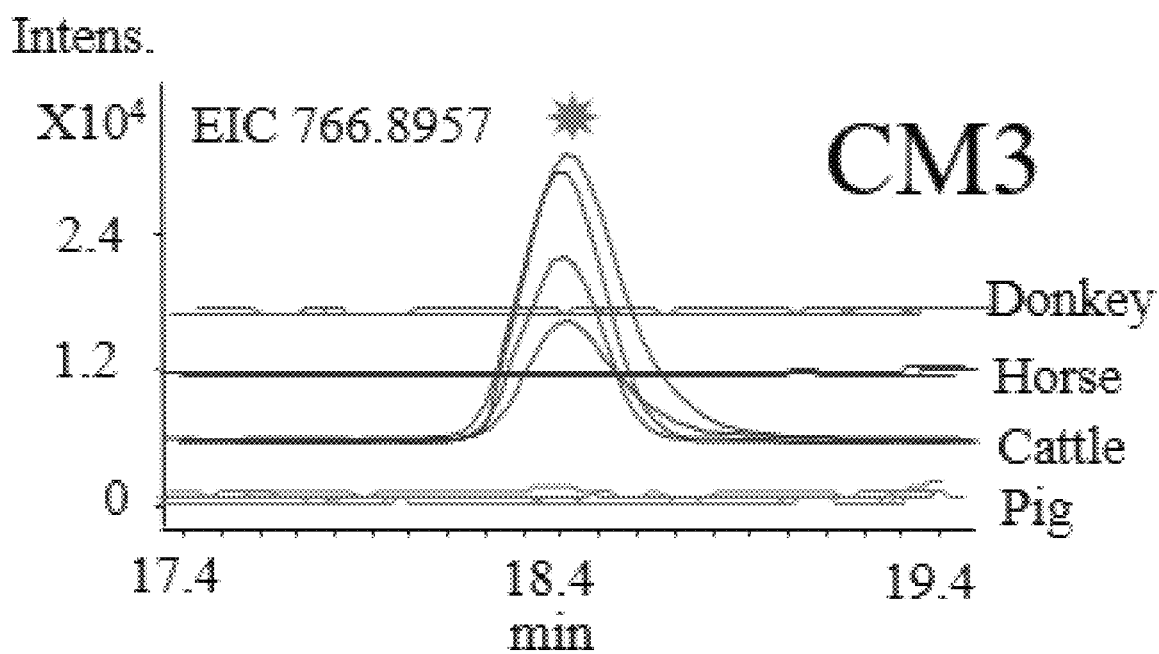
Figure 2:
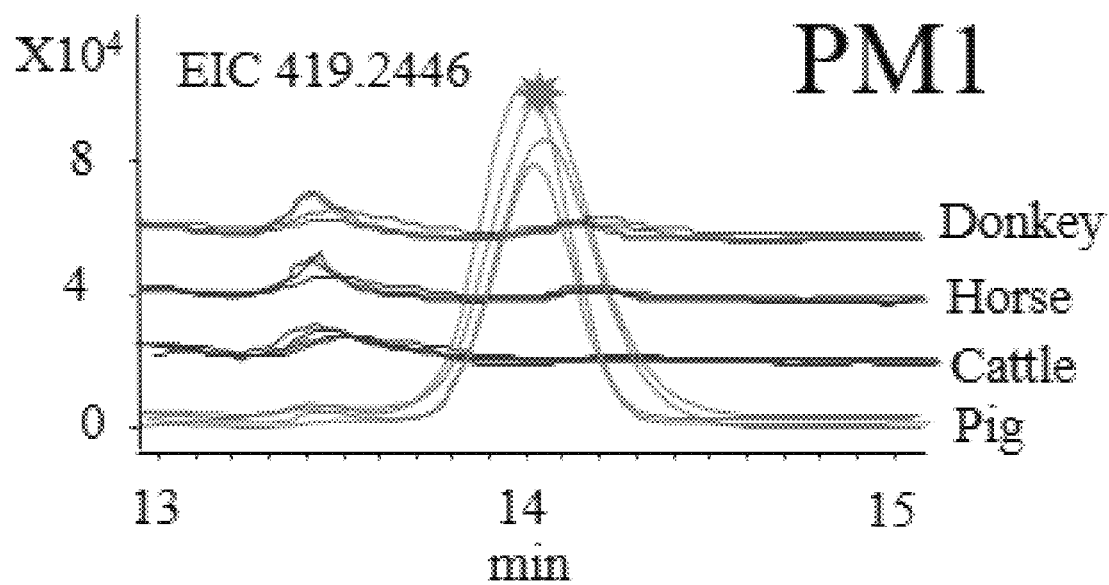
Figure 2:
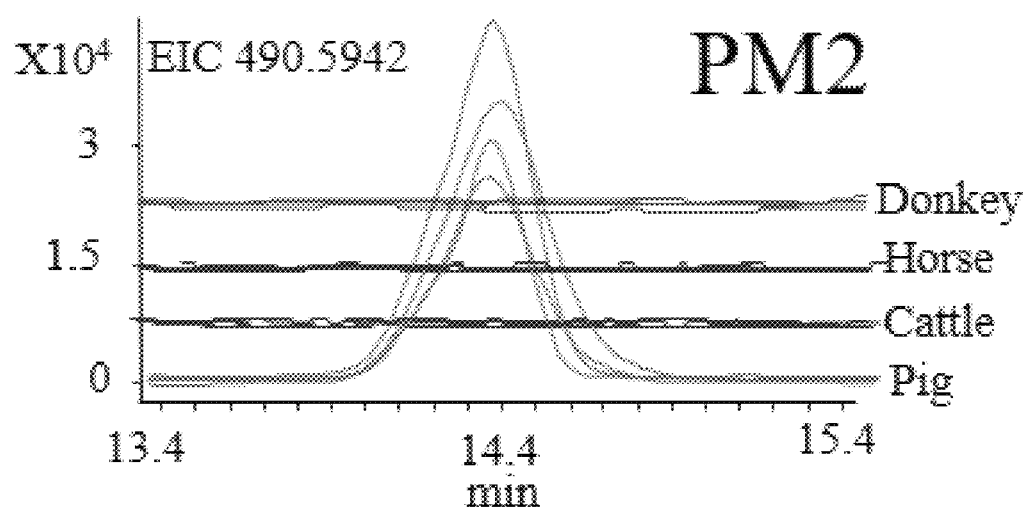
Figure 2:
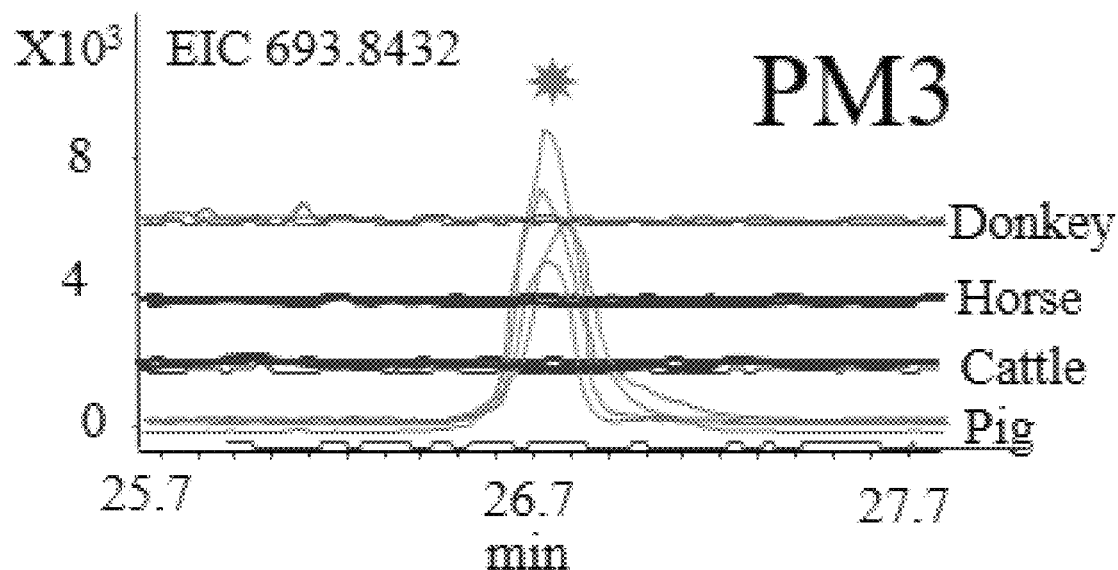
Figure 2:
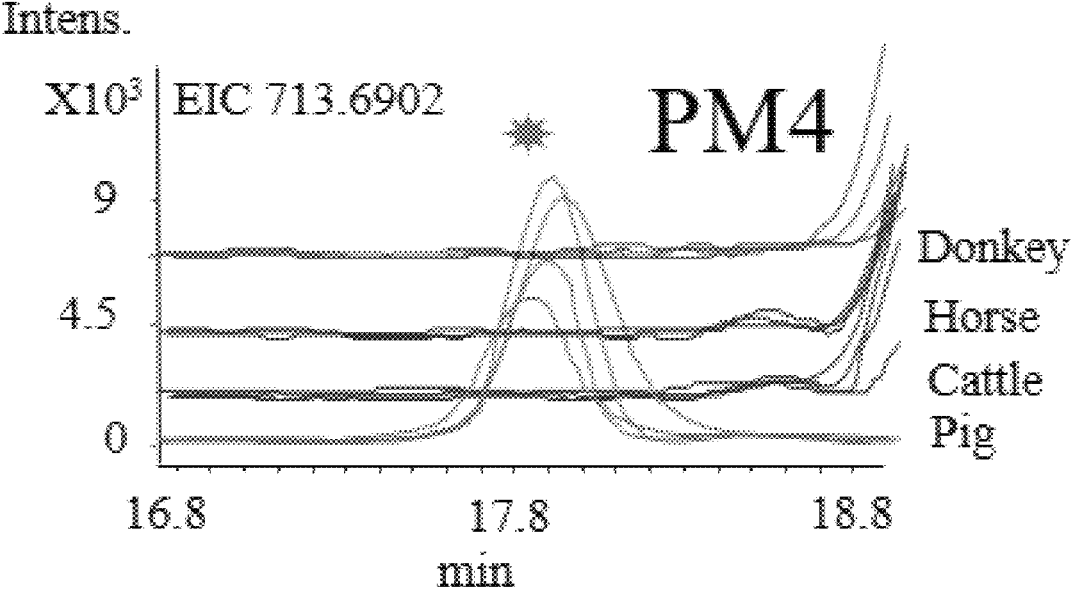
Figure 2:
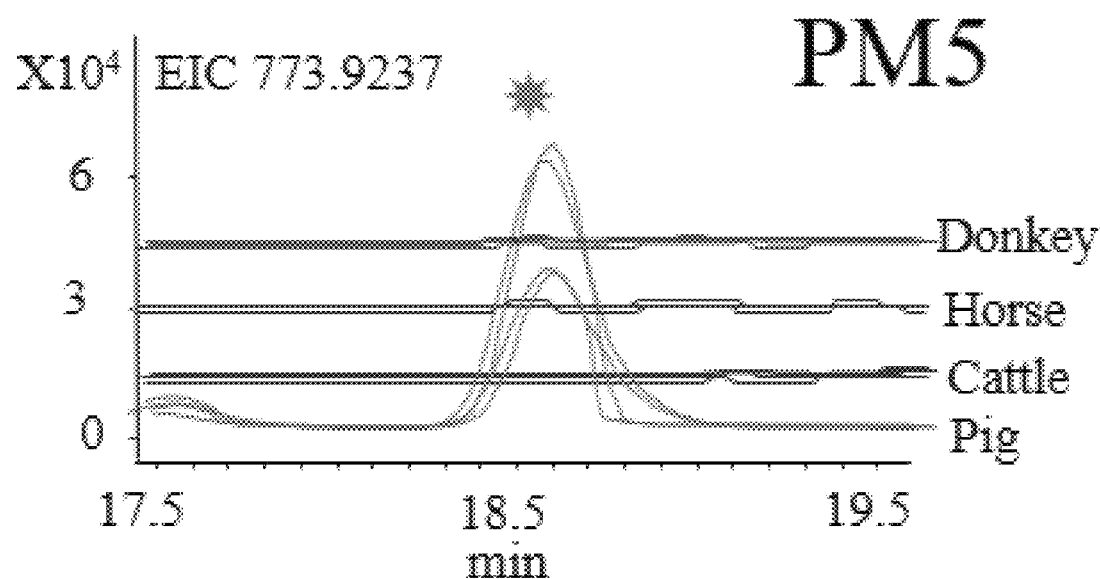
Figure 2:
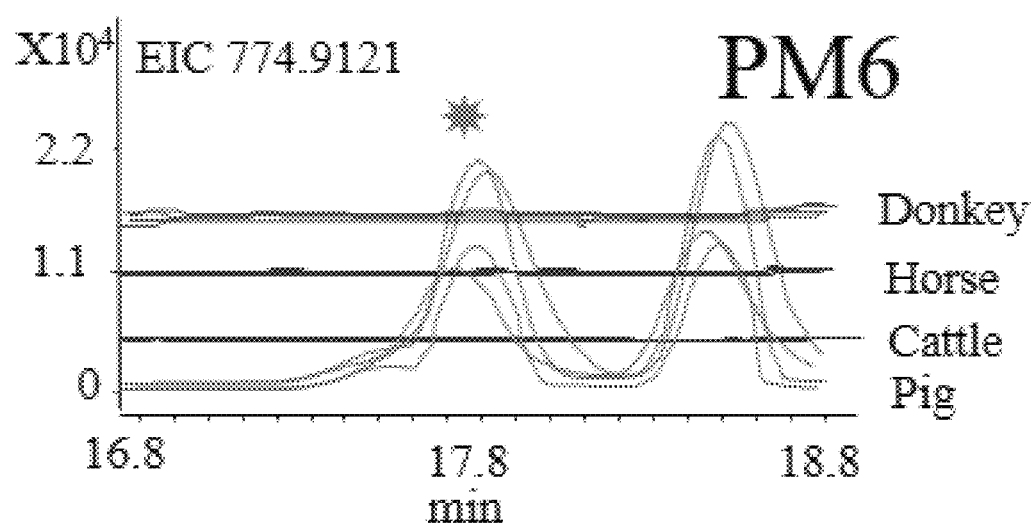

As shown in FIG. 2, the specificity of the peptide markers used in the methods described herein was confirmed by 11 animal hide gelatin samples (2 donkey, 3 horse, 3 pig, and 3 cattle), and collected standard substances of 2 donkey hide gelatins, 1 pig hide gelatin, and 1 cattle hide gelatin. The specificity of these markers was further confirmed by 110 commercial Ejiao samples as demonstrated by the data presented in FIG. 16. These results demonstrate the peptide markers described herein are highly specific for donkey, horse, pig, and cattle hide gelatin samples.

The sensitivity of the methods described herein was assessed by determining the minimum detectable additive amount of each peptide marker present in a sample. Four authentic donkey hide, pig hide, cattle hide, and cattle hide gelatins were mixed in equal amounts, then diluted to samples containing 9.9, 19.8, 49.6 and 99.2 µg/mL of the gelatins, respectively. The method using high-sensitivity peptide markers (as mentioned in FIG. 3) was able to detect these gelatins at 9.9 µg/mL with a high signal-noise ratio (S/N>3), thereby showing high sensitivity of the method.

In instances in which the mass spectrometry method further comprises liquid chromatography, the step of determining whether the hydrolysate comprises one or more peptide markers can further comprise determining whether each of the one or more peptide markers has a predicted liquid chromatography retention time, wherein the predicted liquid chromatography retention time is determined by measuring the retention time of standard samples, wherein each of the standard samples comprises one of the one or more peptide markers. The retention time of standard samples is preferably measured under substantially similar parameters as the hydrolysate sample. Such parameters can include, but are not limited to, column/solid media type, mobile phase solvent(s), mobile phase flow rate, pressure, temperature, and the like. The selection of liquid chromatography parameters is well within the skill of a person of ordinary skill in the art. In certain embodiments, the retention time of the standard samples are those described in Tables 9-12, wherein the chromatography parameters are those described in the LC-QTOF-MS/MS analysis section.

Experimental

The differences between hydrolysate proteins collected from donkey hide gelatin and other animal hide gelatins were examined; differentiating peptide markers were identified and there use as authenticating peptide markers was evaluated. 11 animal hide gelatin samples (2 donkey, 3 horse, 3 pig, and 3 cattle) were prepared, and standard substances of 2 donkey hide gelatins, 1 pig hide gelatin, and 1 cattle hide gelatin were collected, together with 110 commercial Ejiao samples. Species-specific peptide markers were found using LC-QTOF-MS, after comparing base peak chromatographs (BPC) and extracted ion chromatograms (EIC) of these samples. These peptide markers demonstrated to be specific and reliable for authentication purposes.

Chemicals and Materials

Trypsin (sequencing grade) was bought from Shang-hai Yuanye Bio-Technology Co., Ltd. (Shanghai, China). Ammonium bicarbonate ($NH_4HCO_3$) and formic acid (FA) were purchased from Sigma Aldrich (USA). LC-MS-grade acetonitrile and methanol were provided by RCI Labscan Limited (Thailand). Water used was purified with a Millipore Milli-Q water purification system. Shandong Dong-E E-Jiao Co., LTD provided two batches of donkey hide gelatin, three batches of horse hide gelatin, three batches of pig hide gelatin and three batches of cattle hide gelatin. Standard substances of two donkey hide gelatins, one pig hide gelatin and one cattle hide gelatin were obtained from the National Institutes for Food and Drug Control (Beijing, China). 110 commercial Ejiao samples were bought in the Hong Kong market.

Sample Preparation

The powder (5 mg) of four animal gelatins was dissolved in 500 µL 1% ammonium bicarbonate (ABC) and sonicated for 30 min. Then 200 µL of trypsin (5 mg/mL) was added (trypsin:sample=1:5). The mixture was allowed to digest at 37° C. for 18 h. After digestion, 20 µL of formic acid was added to terminate digestion with the final pH less than 4. After that, 400 µL of the solution was mixed with 1 mL of methanol in a 1.5 mL EP-tube to make a 70% MeOH solution. Subsequently, the solution was centrifuged at 15,000 rpm for 15 min. The supernatant was collected for further analysis.

LC-QTOF-MS/MS Analysis

The separation was performed on an Agilent 1290 UHPLC system (Agilent Technologies, Santa Clara, USA) equipped with a binary pump, a thermostatic column, an auto-sampler, a degasser and a diode-array detector. The system was controlled by Mass Hunter B.06 software. An ACQUITY UPLC BEH C18 (2.1 mm×100 mm, 1.7 µm, Waters, Milford, USA) chromatographic column was used and eluted with a linear gradient of 0.1% formic acid in water (A) and 0.1% formic acid in acetonitrile (B) at a flow rate of 0.35 mL/min and at a temperature of 40° C. The solvent gradient programming was as follows: 0-5 min, 1% B; 5-30 min, 1-25% B; 30-32 min, 25-75% B; 32-33 min, 75-100% B; 33-34.1 min, 100-1% B; 34.1-38 min, 1% B. The injection volume was 2 µL.

MS data were collected from an Agilent 6540 Q-TOF mass spectrometer (Agilent Technologies, Santa Clara, USA) equipped with a quadrupole-time-of-flight (Q-TOF) mass spectrometer and a JetStream electrospray ion (ESI) source. Data acquisition was controlled by MassHunter B.06 software (Agilent Technologies). The optimized operating parameters in the negative ion mode were as follows: nebulizing gas ($N_2$) flow rate, 7.0 L/min; nebulizing gas temperature, 300° C.; JetStream gas flow, 8 L/min; sheath gas temperature, 350° C.; nebulizer, 40 psi; capillary, 3000 V; skimmer, 65 V; Oct RFV, 600 V; and fragmenter voltage, 150 V. The mass scan range was set as mass to charge (m/z) 100-2000. MS/MS produces parallel alternating scans that provide precursor ion information at low collision energy, while MS/MS produces full scans that provide information about fragment masses, precursor ions and neutral loss at high collision energy. The collision energies for Auto MS/MS analysis were 20 V and 40 V.

Results and Discussion

Selection of Species-Specific Peptide Markers

Figure 1:
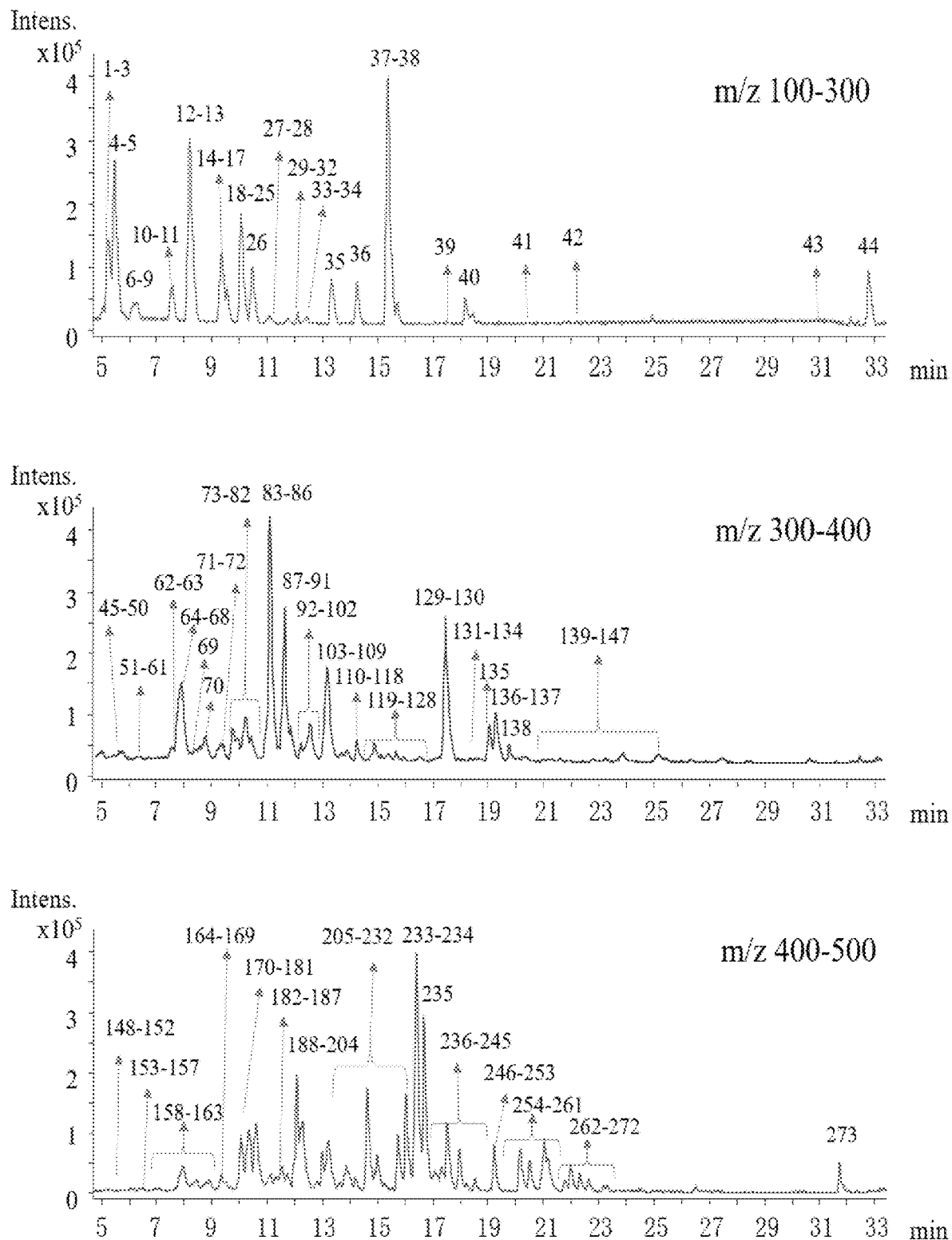
FIG. 1 shows selected ions from LC-Q-TOF-MS base peak chromatograms (BPC) in the scan range of m/z 100-1200 of trypsin hydrolysates of donkey skin gelatin. Note: The chromatograms are from standard substance of donkey skin gelatin.
Figure 1:
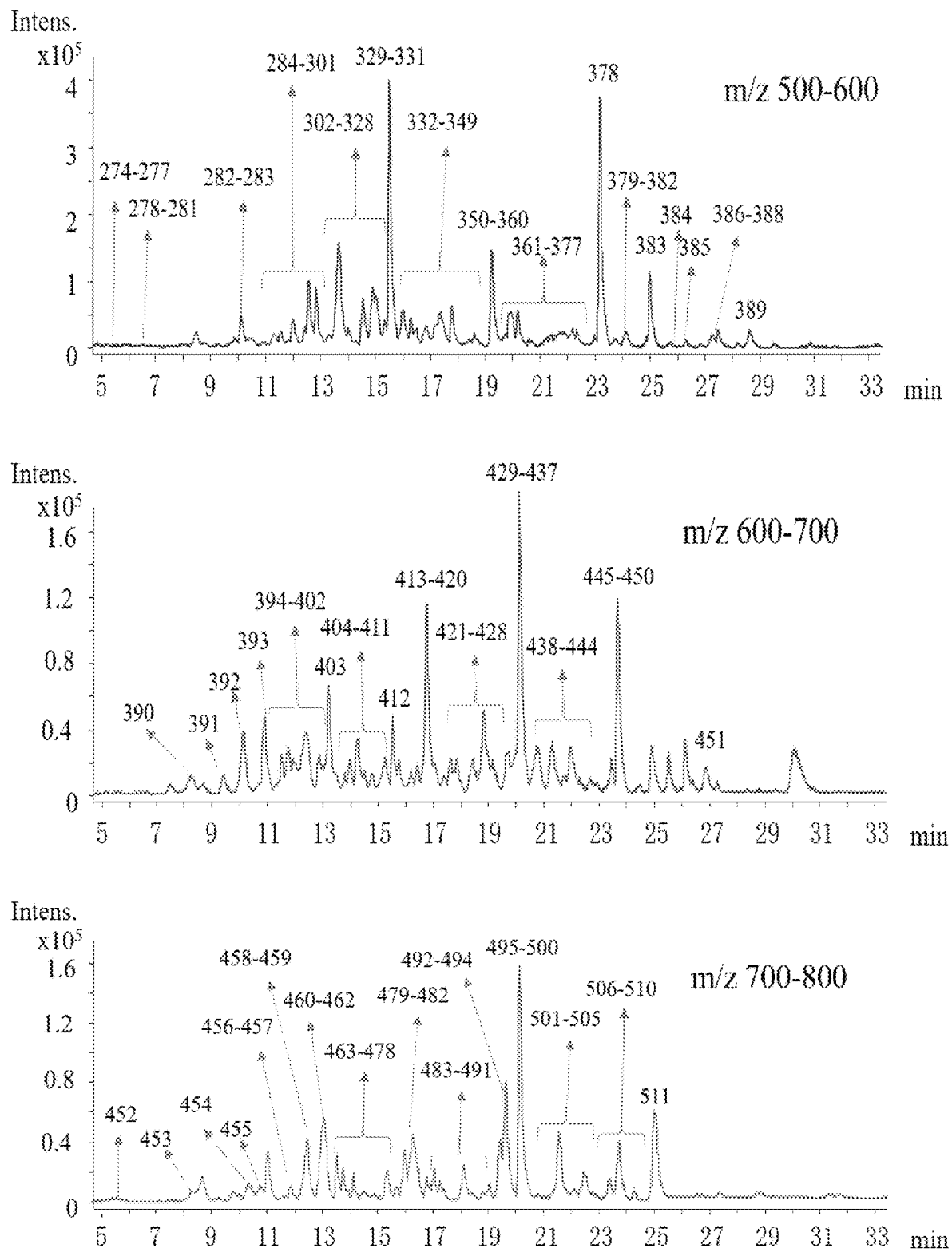
Figure 1:
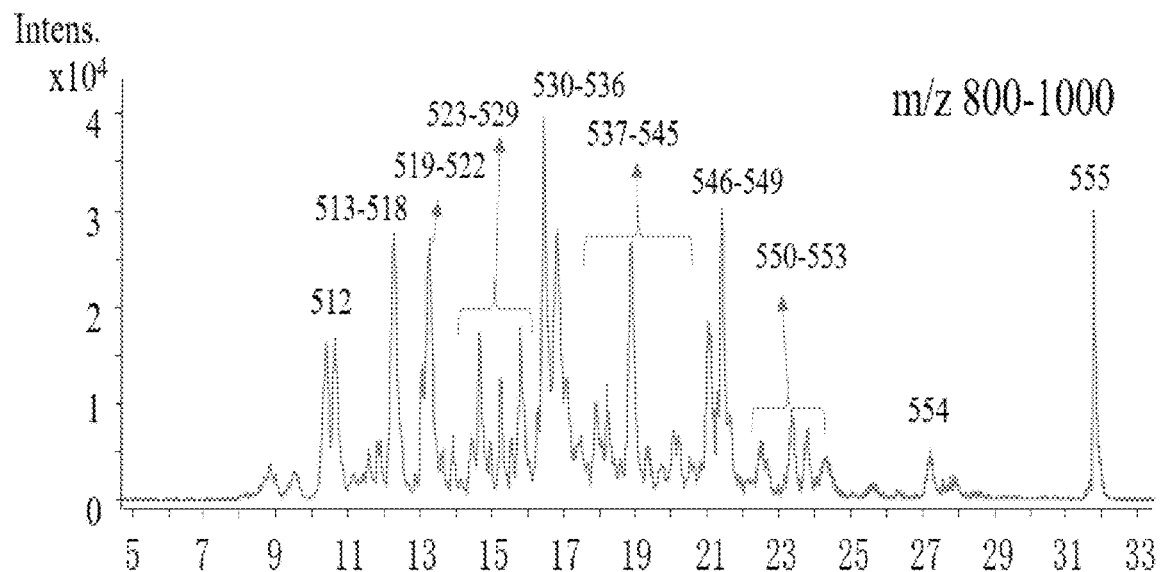
Figure 1:
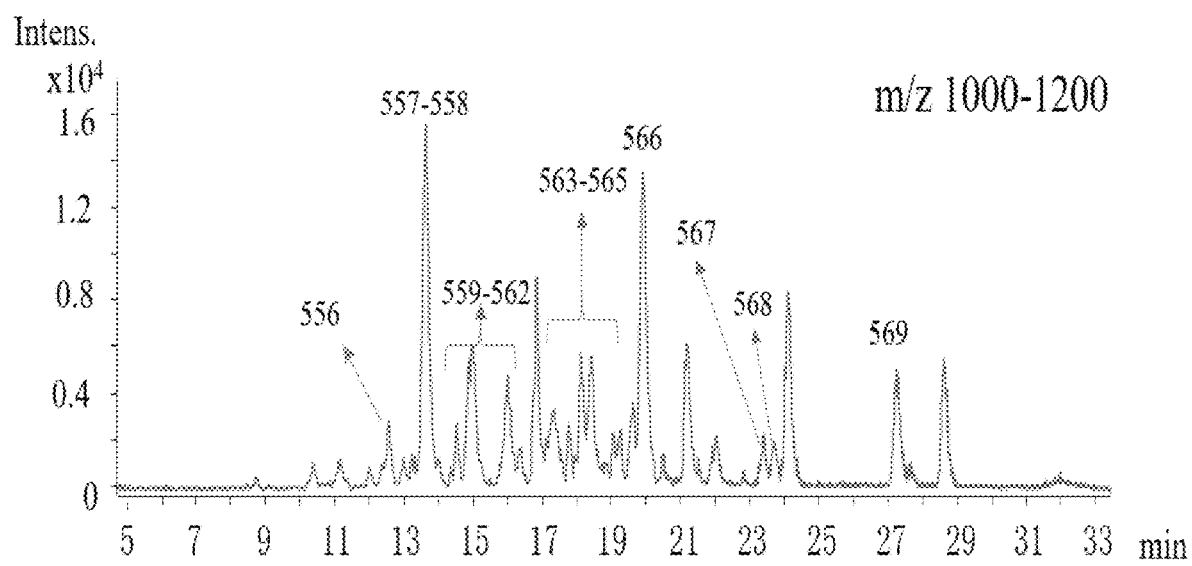

There were several steps to finding authentication peptide markers. Firstly, as shown in FIG. 1, the inventors screened every ion by scanning in the range of m/z 100-1200 and found 569 ions in standard donkey hide gelatin (Table 1). In a similar way, every ion in standard horse gelatin, cattle gelatin and pig gelatin was screened, and found 575, 474, and 453 ions, respectively (Table 2-4). Secondly, the inventors further screened all these 569 donkey ions in other gelatin samples using the extracted ion chromatogram (EIC) mode (FIG. 2). In nature, due to the presence of $^{13}C$ and $^{2}H$, the molar mass of the most abundant isotope is increased by 1 Da. So, its corresponding m/z is increased by 1/z, thereby confirming the charge number. Ions can be largely confirmed as peptides if they are doubly, triply, or quadruply charged peaks. Because the isotope with m/z=1150.0366±0.1 (two charges, Table 1) is another form (m/z=767.0313±0.1, FIG. 3A) of the peptide marker (m/z=766.6952±0.1, DM4, FIG. 2), it was not regarded as new. The results showed 421 ions in all four gelatins, 80 ions in both donkey and horse gelatins but not in cattle or pig gelatin (Table 1), and only 7 donkey-specific ions (Table 5).

All the other gelatins were screened for the 575 ions from horse gelatin, 474 ions from cattle gelatin and 453 ions from pig gelatin, and 4 horse-specific, 3 cattle-specific, and 6 pig-specific ions were found (Table 2-4). These findings were verified in multiple batches of reference samples (FIG. 2). Three horse-specific peptide marker candidates (m/z 455.2539±0.1, 552.7825±0.1 and 716.4201±0.1) were found in only one batch of horse hide, suggesting low consistency; therefore, they were not considered as peptide markers (FIG. 2).

In summary, 17 specific peptide markers (Table 5), namely 7 donkey-specific (DM1-DM7), 1 horse-specific (HM1), 3 cattle-specific (CM1-CM3), and 6 pig-specific peptide markers (PM1-PM6) were identified.

Comparison with Reported Peptide Markers

The specificity of reported donkey-specific peptide markers (Table 6) were also evaluated. There are 32 reported donkey-specific peptide markers in total. The inventors found twenty of them in both donkey and horse gelatins, and 3 of these were present in all four animal gelatins. The intensities of another 12 peptide markers were too low to detect in any animal gelatins. Three Ejiao peptide marker provided in the Chinese Pharmacopeia (peptide sequence: GPAGPTGPVGK (SEQ ID NO: 9), m/z 469.25±0.1; peptide sequence: GPPGAAGPGPR (SEQ ID NO: 2), m/z 539.8±0.1; peptide sequence: GEAGAAGPAGPAGPR (SEQ ID NO: 10), m/z 618.35±0.1) were all found in horse hide gelatin. It is because protein databases under the name of *Equus asinus* are shared by horse and donkey, and there is not a donkey-specific protein database. Therefore, these reported Ejiao authentication peptide markers are not in fact specific.

Donkey-specific peptide markers found in this study showed some advantages, compared to reported peptide markers. The first advantage is that they show excellent specificity. The reported peptide markers were screened by the existing database first, and those not recorded in the database would be missed. So, the specificity of these peptide markers depended on the database. The precondition of these peptide markers' specificity is that the database is powerful enough. While the fact is that these databases are growing and keep being updated. If the database fails to provide sufficient/updated information, the specificity of selected peptide markers will be greatly weakened. Conventional authentication strategies were also employed, e.g., search data against *Bos taurus* (cattle), *Sus scrofa* (pig), *Equus caballus* (horse) and *Equus asinus* (donkey) protein databases downloaded from UniProt KB (Jun. 29, 2020), and select those matched peptides having 99% confidence. Then, the obtained six so-called donkey-specific peptide markers; however, they all existed in horse gelatin samples (Table 6).

The second advantage is that these specific peptide markers are beyond the database. The peptide markers described herein were searched against the *Equus asinus* (horse and donkey) protein database downloaded from UniProt KB (Jun. 29, 2020), and none of the 7 donkey-specific peptide markers described herein matched any peptides in the database. This failure highlights the limitation of existing databases.

Authentication of Commercial Ejiao Products

In order to demonstrate the authentication results simply, one high-sensitivity peptide marker was selected for each species (DM4 for donkey, HM1 for the horse, CM2 for cattle and PM2 for pig) and used to screen 110 commercial Ejiao samples (FIG. 2). MS/MS information of these peptide markers was provided to confirm the ions (FIG. 3-6). The authentication results were highly consistent with those by the recommended peptide markers in Chinese Pharmacopoeia. As summarized in Table 7 and FIG. 7, 57 out of the 110 samples (51.8%) were fake, including 45 cattle-gelatin, 5 horse-gelatin, 3 pig/horse-gelatin, and 1 cattle/horse-gelatin products. Donkey gelatin and horse gelatin were simultaneously found in 2 products, and another did not contain any gelatins. These results suggest the peptide markers described herein provide a reliable method for authenticating animal hide gelatins.

The method described herein provides a more sensitive method than methods based on peptide markers in Chinese Pharmacopoeia. As shown in Table 3 and Table 7, there are inconclusive results for samples No. 55 and No. 65. In sample No. 55, donkey hide gelatin was detected by using the method described herein, but not detected by using the standard method. It is because the standard method needs the help of a horse-specific peptide marker, and the authentication is a kind of indirect result. The sample needs to be authenticated as donkey/horse hide gelatin by the shared peptide marker first, and then only the difference of the gelatin contents calculated by donkey-horse shared peptide markers and horse-specific peptide markers is attributed to donkey-gelatin. However, sometimes the difference is a negative value, which may cover up the existence of donkey hide gelatin. By contrast, the peptide markers described herein directly indicate the presence of donkey hide gelatin without the need for any other test or calculation. As for sample 65, cattle hide gelatin was detected by the method described herein, but not by the standard method. The result was confirmed using all cattle-specific peptide markers in the method (m/z 596.8454±0.1, 604.8556±0.1, 766.8957±0.1). Considering there was only one peptide marker in the standard method (m/z 641.3±0.1, two charges), and it might be destroyed during high-temperature processing, this peptide marker may not be reliable.

Interestingly, the authentication results showed that there are close relationships between authenticity and price, registration, and manufacturers. Among these tested 110 samples, the price of all the authentic samples was above HK$2,450/500 g, while the fake samples were all priced below HK$2,250/500 g (FIG. 8). 74 samples showed the manufacturer's name of them, 53 (72%) were authentic, while the other 36 samples, without manufacturer's name, were proved to be fake. 46 samples were labeled with State Food and Drug Administration (SFDA) License No. and 64 samples lacked this label. It is impressive that 45 out of 46 licensed products were authentic, while of 64 non-licensed products only 8 were authentic (FIG. 9). This data suggests that there is considerable confusion in the Ejiao market. The data also suggests that high price and the presence of an SFDA license number tend to be predictors of authenticity. More accurate and reliable authentication methods are greatly desired.

In summary, seventeen specific peptide markers were found for authentication of different animal hide gelatins, after comparing their peptide profiles generated by trypsin digestion. Among them, seven donkey-specific peptide markers were reported for the first time. Compared with published donkey-specific peptide markers, these new peptide markers showed higher specificity and reliability, and revealed 57 fakes out of 110 commercial Ejiao samples.

INDUSTRIAL APPLICABILITY

The present disclosure relates to method of identifying gelatin derived from animal hides, specifically those from donkeys, horses, pigs, and cattle using one or more of seventeen specific peptide markers: seven donkey-specific, one horse-specific, three cattle-specific, and six pig-specific.

What is claimed is:

1. A method of identifying an animal hide gelatin in a sample, the method comprising:
   providing a hydrolysate of the sample;
   analyzing the hydrolysate of the sample using a mass spectroscopy method; and
   detecting one or more peptide markers, wherein a donkey hide gelatin is identified when the one or more peptide markers have an observed mass to charge ratio (m/z) selected from the group consisting of: $518.2695\pm0.1$ (DM1), $675.6632\pm0.1$ (DM2), $761.3672\pm0.1$ (DM3), $766.6952\pm0.1$ (DM4), $774.0218\pm0.1$ (DM5), $784.3392\pm0.1$ (DM6), and $854.0603\pm0.1$ (DM7);
   or a pig hide gelatin is present when two or more peptide markers have an observed mass to charge ratio (m/z) selected from the group consisting of: $419.2446\pm0.1$ (PM1), $490.5942\pm0.1$ (PM2), $693.8432\pm0.1$ (PM3), $713.6902\pm0.1$ (PM4), $773.9237\pm0.1$ (PM5), and $774.9121\pm0.2$ (PM6).

2. The method of claim 1 further comprising hydrolyzing the sample thereby forming the hydrolysate of the sample.

3. The method of claim 1 further comprising hydrolyzing the sample using a protease thereby forming the hydrolysate of the sample.

4. The method of claim 1 further comprising hydrolyzing the sample using a protease selected from the group consisting of trypsin, chymotrypsin, lysine protease, aspartic protease, pepsin, papain, proteinase K, calpain, and subtilisin thereby forming the hydrolysate of the sample.

5. The method of claim 1 further comprising hydrolyzing the sample using trypsin thereby forming the hydrolysate of the sample.

6. The method of claim 1, wherein the mass spectrometry method is tandem mass spectroscopy (MS/MS) and further comprises liquid chromatography.

7. The method of claim 1, wherein the mass spectrometry method comprises high-performance liquid chromatography (HPLC-MS/MS) or ultra-performance liquid chromatography (UPLC-MS/MS).

8. The method of claim 6, wherein the step of detecting the one or more peptide markers further comprises detecting that each of the one or more peptide markers has a predicted liquid chromatography retention time, wherein the predicted liquid chromatography retention time of each of the one or more peptide markers is determined by measuring a retention time of one or more standard samples, wherein each of the one or more standard samples comprises a standard specific to one of the one or more peptide markers.

9. The method of claim 1, wherein the step of detecting the one or more peptide markers comprises detecting 2 to 7 peptide markers selected from the group consisting of DM1, DM2, DM3, DM4, DM5, DM6, and DM7.

10. The method of claim 1, wherein the mass spectrometry method is MS/MS and further comprises an ultra-performance liquid chromatography method; and the step of detecting the one or more peptide markers further comprises detecting that each of the one or more peptide markers has a predicted ultra-performance liquid chromatography retention time, wherein the ultra-performance predicted liquid chromatography retention time of each of the one or more peptide markers is determined by measuring as retention time of one or more standard samples, wherein each of the one or more standard samples comprises a standard specific to one of the one or more peptide markers.

11. The method of claim 1, wherein the step of detecting comprises detecting the one or more peptide markers having an observed m/z are DM1, DM2, DM3, DM4, DM5, DM6, and DM7.

12. The method of claim 11 further comprising:
   hydrolyzing the sample using trypsin thereby forming the hydrolysate of the sample; and the mass spectrometry method is MS/MS and further comprises ultra-performance liquid chromatography.

13. The method of claim 1 further comprising detecting one or more additional peptide markers, wherein the one or more additional peptide markers have an observed mass to charge ratio (m/z) selected from the group consisting of: 386.2108±0.1 (HM1) indicating the presence of horse hide gelatin and 766.8957±0.1 (CM3) indicating the presence of cattle hide gelatin.

* * * * *

SEQUENCE LISTING

<160> NUMBER OF SEQ ID NOS: 10

<210> SEQ ID NO 1
<211> LENGTH: 15
<212> TYPE: PRT
<213> ORGANISM: Equus asinus

<400> SEQUENCE: 1

His Pro Gly Asp Phe Gly Ala Asp Ala Gln Gly Ala Met Thr Lys
1               5                   10                  15

<210> SEQ ID NO 2
<211> LENGTH: 12
<212> TYPE: PRT
<213> ORGANISM: Equus asinus

<400> SEQUENCE: 2

Gly Pro Pro Gly Ala Ala Gly Pro Pro Gly Pro Arg
1               5                   10

<210> SEQ ID NO 3
<211> LENGTH: 9
<212> TYPE: PRT
<213> ORGANISM: Equus caballus

<400> SEQUENCE: 3

Gly Ala Ser Gly Pro Ala Gly Val Arg
1               5

<210> SEQ ID NO 4
<211> LENGTH: 13
<212> TYPE: PRT
<213> ORGANISM: Bos taurus

<400> SEQUENCE: 4

Ile Gly Gln Pro Gly Ala Val Gly Pro Ala Gly Ile Arg
1               5                   10

<210> SEQ ID NO 5
<211> LENGTH: 16
<212> TYPE: PRT
<213> ORGANISM: Sus scrofa

<400> SEQUENCE: 5

His Gly Asp Gln Gly Ala Pro Gly Pro Val Gly Pro Ala Gly Pro Arg
1               5                   10                  15

<210> SEQ ID NO 6
<211> LENGTH: 18
<212> TYPE: PRT
<213> ORGANISM: Bos taurus

<400> SEQUENCE: 6

Gly Glu Pro Gly Pro Ala Gly Ala Val Gly Pro Ala Gly Ala Val Gly
1               5                   10                  15

Pro Arg

<210> SEQ ID NO 7
<211> LENGTH: 26
<212> TYPE: PRT
<213> ORGANISM: Sus scrofa

<400> SEQUENCE: 7

Gly Glu Ser Gly Pro Ala Gly Pro Gly Ala Pro Gly Ala Pro Gly
1               5                   10                  15

Ala Pro Gly Pro Val Gly Pro Ala Gly Lys
            20                  25

<210> SEQ ID NO 8

```
<211> LENGTH: 18
<212> TYPE: PRT
<213> ORGANISM: Sus scrofa

<400> SEQUENCE: 8

Gly Glu Thr Gly Pro Ala Gly Pro Ala Gly Pro Val Gly Pro Val Gly
1               5                   10                  15

Ala Arg

<210> SEQ ID NO 9
<211> LENGTH: 11
<212> TYPE: PRT
<213> ORGANISM: Equus asinus

<400> SEQUENCE: 9

Gly Pro Ala Gly Pro Thr Gly Pro Val Gly Lys
1               5                   10

<210> SEQ ID NO 10
<211> LENGTH: 15
<212> TYPE: PRT
<213> ORGANISM: Equus asinus

<400> SEQUENCE: 10

Gly Glu Ala Gly Ala Ala Gly Pro Ala Gly Pro Ala Gly Pro Arg
1               5                   10                  15
```